(12) United States Patent
Abdul-Manan et al.

(10) Patent No.: US 12,031,150 B2
(45) Date of Patent: *Jul. 9, 2024

(54) METHODS, COMPOSITIONS AND KITS FOR INCREASING GENOME EDITING EFFICIENCY

(71) Applicant: Vertex Pharmaceuticals Incorporated, Boston, MA (US)

(72) Inventors: Norzehan Abdul-Manan, Boston, MA (US); David A. Newsome, Boston, MA (US); Jacque Zwahlen, Boston, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/407,421

(22) Filed: Aug. 20, 2021

(65) Prior Publication Data

US 2022/0106615 A1 Apr. 7, 2022

Related U.S. Application Data

(62) Division of application No. 16/317,314, filed as application No. PCT/US2017/041979 on Jul. 13, 2017, now Pat. No. 11,124,805.

(60) Provisional application No. 62/361,781, filed on Jul. 13, 2016, provisional application No. 62/361,961, filed on Jul. 13, 2016.

(51) Int. Cl.
| | | |
|---|---|---|
| C12N 15/90 | (2006.01) |
| A61P 35/00 | (2006.01) |
| A61P 35/02 | (2006.01) |
| A61P 43/00 | (2006.01) |
| C07D 401/14 | (2006.01) |
| C12N 9/22 | (2006.01) |
| C12N 15/11 | (2006.01) |

(52) U.S. Cl.
CPC ......... *C12N 15/907* (2013.01); *C07D 401/14* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,008,336 A | 12/1999 | Hanson et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |

(Continued)

FOREIGN PATENT DOCUMENTS

| | | |
|---|---|---|
| AU | 2017295720 B2 | 1/2018 |
| AU | 2021232813 B2 | 10/2021 |

(Continued)

OTHER PUBLICATIONS

International Search Report and Written Opinion for PCT/US17/41979, dated Sep. 22, 2017. 10 pages.

(Continued)

*Primary Examiner* — Suzanne M Noakes
*Assistant Examiner* — Jae W Lee
(74) *Attorney, Agent, or Firm* — Barnes & Thornburg LLP

(57) ABSTRACT

Methods of editing a target genomic region(s), methods of repairing of a DNA break via a HDR pathway, methods of inhibiting or suppressing repair of a DNA break via a NHEJ pathway, and methods of modifying expression of a gene(s) or protein(s) comprise administering to one or more cells that include one or more target genomic regions, a genome editing system and a DNA protein-kinase (DNA-PK) inhibitor disclosed herein. Kits and compositions for editing a target gene comprise a genome editing system and a DNA-PK inhibitor disclosed herein.

18 Claims, 9 Drawing Sheets

Specification includes a Sequence Listing.

(56) References Cited

U.S. PATENT DOCUMENTS

| | | |
|---|---|---|
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,253,273 B2 | 8/2007 | Collingwood |
| 7,262,054 B2 | 8/2007 | Jamieson et al. |
| 7,361,635 B2 | 4/2008 | Miller et al. |
| 8,153,773 B2 | 4/2012 | Jemielity et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,145,565 B2 | 9/2015 | Carroll et al. |
| 9,181,535 B2 | 11/2015 | Liu et al. |
| 9,365,964 B2 | 6/2016 | Kim |
| 2005/0064474 A1 | 3/2005 | Urnov et al. |
| 2005/0267061 A1 | 12/2005 | Martin |
| 2006/0188987 A1 | 8/2006 | Guschin et al. |
| 2007/0218528 A1 | 9/2007 | Miller |
| 2008/0131962 A1 | 6/2008 | Miller |
| 2011/0201055 A1 | 8/2011 | Doyon et al. |
| 2013/0281431 A1 | 10/2013 | Charifson et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2019/0225990 A1 | 7/2019 | Abdul-Manan et al. |
| 2022/0106615 A1 | 4/2022 | Abdul-Manan et al. |

FOREIGN PATENT DOCUMENTS

| | | |
|---|---|---|
| CA | 3030783 A1 | 1/2018 |
| CN | 105408497 | 3/2016 |
| CN | 104640852 B | 4/2017 |
| CN | 109863143 B | 10/2021 |
| EP | 2771468 B1 | 2/2015 |
| EP | 2784162 B1 | 4/2015 |
| EP | 2764103 B1 | 8/2015 |
| EP | 3484870 B1 | 11/2022 |
| EP | 4219462 A1 | 8/2023 |
| ES | 2938210 | 4/2023 |
| GB | 2338237 B | 12/1999 |
| JP | 2015514804 | 5/2015 |
| JP | 2015534817 | 12/2015 |
| JP | 2019521139 | 7/2019 |
| WO | WO 1991016024 | 10/1991 |
| WO | WO 1991017424 | 11/1991 |
| WO | WO 1993024641 | 12/1993 |
| WO | WO 1995019431 | 7/1995 |
| WO | WO 1996006166 | 2/1996 |
| WO | WO 1998037186 | 8/1998 |
| WO | WO 1998053057 | 11/1998 |
| WO | WO 1998053058 | 11/1998 |
| WO | WO 1998053059 | 11/1998 |
| WO | WO 1998053060 | 11/1998 |
| WO | WO 1998054311 | 12/1998 |
| WO | WO 2000027878 | 5/2000 |
| WO | WO 2001060970 | 8/2001 |
| WO | WO 2001088197 | 11/2001 |
| WO | WO 2002016536 | 2/2002 |
| WO | WO 2002077227 | 10/2002 |
| WO | WO 2002099084 | 12/2002 |
| WO | WO 2003016496 | 2/2003 |
| WO | WO 2007014275 | 2/2007 |
| WO | WO 2010017562 | 2/2010 |
| WO | WO 2013130824 | 9/2013 |
| WO | WO 2013/163190 A1 | 10/2013 |
| WO | WO 2014018423 | 1/2014 |
| WO | 2014071219 A1 | 5/2014 |
| WO | WO 2014093595 | 6/2014 |
| WO | WO 2014093622 | 6/2014 |
| WO | WO 2014093635 | 6/2014 |
| WO | WO 2014093655 | 6/2014 |
| WO | WO 2014093661 | 6/2014 |
| WO | WO 2014093694 | 6/2014 |
| WO | WO 2014093701 | 6/2014 |
| WO | WO 2014093709 | 6/2014 |
| WO | WO 2014093712 | 6/2014 |
| WO | WO 2014093718 | 6/2014 |
| WO | WO 2014172458 | 10/2014 |
| WO | WO 2014204723 | 12/2014 |
| WO | WO 2014204724 | 12/2014 |
| WO | WO 2014204725 | 12/2014 |
| WO | WO 2014204726 | 12/2014 |
| WO | WO 2014204727 | 12/2014 |
| WO | WO 2014204728 | 12/2014 |
| WO | WO 2014204729 | 12/2014 |
| WO | 2015058067 A1 | 4/2015 |
| WO | WO 2015048557 | 4/2015 |
| WO | WO 2015048577 | 4/2015 |
| WO | WO 2016028682 | 2/2016 |
| WO | 2016081923 A2 | 5/2016 |

OTHER PUBLICATIONS

Peng et al., "Potential pitfalls of CRISPR/Cas9-mediated genome editing", FEBS J., 283(7): 1218-31 (2016).

Robert et al., "Pharmacological inhibition of DNA-PK stimulates Cas9-mediated genome editing", Genome Med., 7 (93): 1-11 (2015).

Ahmad, I., and Allen, T.M., "Antibody-Mediated Specific Binding and Cytotoxicity of Liposome-Entrapped Doxorubicin to Lung Cancer Cells in Vitro," Cancer Research, pp. 4817-4820, Sep. 1, 1992, vol. 52, No. 17, American Society for Cancer Research, Philadelphia, PA, US.

Bae, S., et al., "Cas-OFFinder: A Fast and Versatile Algorithm That Searches for Potential Off-Target Sites of Cas9 RNA-Guided Endonucleases," Bioinformatics, pp. 1473-1475, Jan. 24, 2014, vol. 30, No. 10, Oxford University Press, Oxford, UK.

Beerli, R.R., and Barbas, C.F. III., "Engineering Polydactyl Zinc-Finger Transcription Factors," Nature Biotechnology, Feb. 2002, pp. 135-141, vol. 20, Nature Portfolio, London, UK.

Behr, J.-P., "Gene Transfer with Synthetic Cationic Amphiphiles: Prospects for Gene Therapy," Bioconjugate Chemistry, Sep. 1, 1994, pp. 382-389, vol. 5, No. 5, American Chemical Society, Washington, DC.

Bell, C.C., et al., "A High-Throughput Screening Strategy for Detecting CRISPR-Cas9 Induced Mutations Using Next-Generation Sequencing," BMC Genomics, 7 pages, Nov. 20, 2014, 15, No. 1, Article No. 1002, Springer Nature, London, UK.

Bennardo, N., et al., "Alternative-NHEJ Is a Mechanistically Distinct Pathway of Mammalian Chromosome Break Repair," PLoS Genetics, 10 pages, Jun. 27, 2008, vol. 4, Issue 6, e1000110, Public Library of Science, San Francisco, CA, US.

Berge, S.M., et al., "Pharmaceutical Salts", Journal of Pharmaceutical Sciences, Jan. 1977, pp. 1-19, vol. 66, No. 1, vol. 66, Elsevier, Amsterdam, NL.

(56) References Cited

OTHER PUBLICATIONS

Bitinaite, J., et al., "FokI Dimerization is Required for DNA Cleavage," Proceedings of the National Academy of Sciences of the United States of America, pp. 10570-10575, Sep. 1998, vol. 95, United States National Academy of Sciences, Washington, DC, US.
Blaese, M., et al., "Vectors in Cancer Therapy: How Will They Deliver?" Cancer Gene Therapy, pp. 291-297, 1995, vol. 2, No. 4, Nature Portfolio, London, UK.
Certo, M.T. et al., "Tracking Genome Engineering Outcome at Individual DNA Breakpoints", Nature Methods, Aug. 2011, pp. 671-676, vol. 8, No. 8, Nature Portfolio, London, UK.
Choo, Y., and Isalan, M., "Advances in Zinc Finger Engineering," Current Opinion in Structural Biology, pp. 411-416, Aug. 1, 2000, vol. 10, Issue 4, Elsevier, Amsterdam, NL.
Crystal, R.G., "Transfer of Genes to Humans: Early Lessons and Obstacles to Success," Science, Sep. 20, 1995, pp. 404-410, vol. 270, American Association for the Advancement of Science, Washington, DC, US.
Fonfara, I., et al., "The CRISPR-associated DNA-cleaving enzyme Cpf1 Also Processes Precursor CRISPR RNA," Nature, pp. 517-521, Apr. 28, 2016, vol. 532, Macmillan Publishers Limited, New York City, NY, US.
Fu, Y. et al., "Improving CRISPR-Cas Nuclease Specificity Using Truncated Guide RNAs," Nature Biotechnology, pp. 279-284, Mar. 2014, vol. 32, No. 3, Nature Portfolio, London, UK.
Gao, F., et al., "DNA-guided Genome Editing Using the Natronobacterium gregoryi Argonaute," Nature Biotechnology, pp. 768-773, May 2016, vol. 34, No. 7, Nature Portfolio, London, UK, with Aug. 1, 2017 Retraction.
Gao, X., and Huang, L., "Cationic Liposome-Mediated Gene Transfer", Gene Therapy, 1995, pp. 710-722, vol. 2, Nature Portfolio, London, UK.
Heigwer et al., Nat Methods, (2014), vol. 11, No. 2, pp. 122-123.
Hermonat; Muzyczka, PNAS, (1984), vol. 81, pp. 6466-6470.
Heyer et al., "Regulation of homologous recombination in eukaryotes." Annual Review of Genetics 44: pp. 113-139 (2010).
Hsu et al., Natbiotechnol, (2013), vol. 31, No. 9, pp. 827-832.
Isalan, Nature Biotechnol., (2001), vol. 19, pp. 656-660.
Kim et al., J. Biol. Chem., (1994), vol. 269, pp. 31,978-31,982.
Kim et al., Proc. Natl. Acad. Sci. USA, (1994), vol. 91, pp. 883-887.
Kotin, Human Gene Therapy, (1994), vol. 5, pp. 793-801.
Li et al., Proc. Natl. Acad. Sci. USA, (1992), vol. 89, pp. 4275-4279.
Li et al., Proc. Natl. Acad. Sci. USA, (1993), vol. 90, pp. 2764-2768.
Lin et al., "Enhanced homology-directed human genome engineering by controlled timing of CRISPR/Cas9 delivery", eLIFE, (2014), vol. 15, p. 1-13.
MacDiarmid et al., Nature Biotechnology, (2009), vol. 27, No. 7, p. 643.
Mali et al., Science, (2013), vol. 339, No. 6121, pp. 823-826.
Miyaoka et al., "Systematic quantification of HDR and NHEJ reveals effectrs of locus, nuclease, and cell type on genomeeditin", Scientific Reports, (2016), vol. 6, pp. 1-12.
Muzyczka, J., Clin. Invest., (1994), vol. 94, p. 1351.
Pabo et al., Ann. Rev. Biochem., (2001), vol. 70, pp. 313-340.
Remy et al., Bioconjugate Chem., (1994), vol. 5, pp. 647-654.
Roberts et al., Nucleic Acids Res., (2003), vol. 31, pp. 418-420.
Rouet et al., "Dexheimer T. DNA repair pathways and mechanisms", DNA repair of cancer stem cells. Dordrecht, Springer, (2013), pp. 19-32.
Sambrook et al., "Chapters 16 and 17", Molecular Cloning: A Laboratory Manual, 2nd ed., Cold Spring Harbor Laboratory Press, (1989).
Samulski et al., J. Virol, (1989), vol. 63, pp. 3822-3828.
Segal et al., Curr. Opin. Biotechnol., (2001), vol. 12, pp. 632-637.
Swiech et al., "In vivo interrogation of gene function in the mammalian brain using CRISPRCas9", Nat Biotechnol., (2015), vol. 33, No. 1, pp. 102-62014.
Tratschin et al., Mol Cell. Biol., (1984), vol. 4, pp. 2072-2081.
Tratschin et al., Mol. Cell. Biol., (1985), vol. 5, pp. 3251-3260.
West et al., Virology, (1987), vol. 160, pp. 38-47.
Wiedenheft, B., Hsu, P.D. eta. (2014).
Xiao A et al., Bioinformatics, (2014) Pub Med PMID: 24389662.
Zetsche et al., "Cpf1 is a single RNA-guided endonuclease of a class 2 CRISPR-Cas system," Cell, 163 (3), (2015), pp. 759-771.

```
                        SEQUENCE LISTING

<160> NUMBER OF SEQ ID NOS: 8

<210> SEQ ID NO 1
<211> LENGTH: 3531
<212> TYPE: DNA
<213> ORGANISM: Artificial Sequence
<220> FEATURE:
<223> OTHER INFORMATION: Synthetic Polynucleotide

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaaac tagtgcgacg taaacggcca     420
caagttcagc gtgtccggcg agggcgaggg cgatgccacc tacggcaagc tgaccctgaa     480
gttcatctgc accaccggca agctgcccgt gccctggccc accctcgtga ccaccctgac     540
ctacggcgtg cagtgcttca gccgctaccc cgaccacatg aagcagcacg acttcttcaa     600
gtccgccatg cccgaaggct acgtccagga gcgcaccatc ttcttcaagg acgacggcaa     660
ctacaagacc cgcgccgagg tgaagttcga gggcgacacc ctggtgaacc gcatcgagct     720
gaagggcatc gacttcaagg aggacggcaa catcctgggg cacaagctgg agtacaacta     780
caacagccac aacgtctata tcatggccga caagcagaag aacggcatca aggtgaactt     840
caagatccgc cacaacatcg aggacggcag cgtgcagctc gccgaccact accagcagaa     900
cacccccatc ggcgacggcc ccgtgctgct gcccgacaac cactacctga gcacccagtc     960
cgccctgagc aaagacccca acgagaagcg cgatcacatg gtcctgctgg agttcgtgac    1020
cgccgccggg atcactctcg gcatggacgt cgacaccggt gatatcaagc ttggcgtaat    1080
catggtcata gctgtttcct gtgtgaaatt gttatccgct cacaattcca cacaacatac    1140
gagccggaag cataaagtgt aaagcctggg gtgcctaatg agtgagctaa ctcacattaa    1200
```

```
ttgcgttgcg ctcactgccc gctttccagt cgggaaacct gtcgtgccag ctgcattaat    1260
gaatcggcca acgcgcgggg agaggcggtt tgcgtattgg gcgctcttcc gcttcctcgc    1320
tcactgactc gctgcgctcg gtcgttcggc tgcggcgagc ggtatcagct cactcaaagg    1380
cggtaatacg gttatccaca gaatcagggg ataacgcagg aaagaacatg tgagcaaaag    1440
gccagcaaaa ggccaggaac cgtaaaaagg ccgcgttgct ggcgtttttc cataggctcc    1500
gcccccctga cgagcatcac aaaaatcgac gctcaagtca gaggtggcga acccgacag    1560 gactataaag ataccaggcg tttccccctg gaagctccct cgtgcgctct cctgttccga    1620
ccctgccgct taccggatac ctgtccgcct ttctcccttc gggaagcgtg gcgctttctc    1680
atagctcacg ctgtaggtat ctcagttcgg tgtaggtcgt tcgctccaag ctgggctgtg    1740
tgcacgaacc cccgttcag cccgaccgct gcgccttatc cggtaactat cgtcttgagt    1800
ccaacccggt aagacacgac ttatcgccac tggcagcagc cactggtaac aggattagca    1860
gagcgaggta tgtaggcggt gctacagagt tcttgaagtg gtggcctaac tacggctaca    1920
ctagaagaac agtatttggt atctgcgctc tgctgaagcc agttaccttc ggaaaaagag    1980
ttggtagctc ttgatccggc aaacaaacca ccgctggtag cggtggtttt tttgtttgca    2040
agcagcagat tacgcgcaga aaaaaggat ctcaagaaga tcctttgatc ttttctacgg    2100
ggtctgacgc tcagtggaac gaaaactcac gttaagggat tttggtcatg agattatcaa    2160
aaaggatctt cacctagatc cttttgatcc ccgccacggt tgatgagagc tttgttgtag    2220
gtggaccagt tggtgatttt gaacttttgc tttgccacgg aacggtctgc gttgtcggga    2280
agatgcgtga tctgatcctt caactcagca aaagttcgat ttattcaaca aagccgccgt    2340
cccgtcaagt cagcgtaatg ctctgccagt gttacaacca attaaccaat tctgattaga    2400
aaaactcatc gagcatcaaa tgaaactgca atttattcat atcaggatta tcaataccat    2460 attttgaaa aagccgtttc tgtaatgaag gagaaaactc accgaggcag ttccatagga    2520
tggcaagatc ctggtatcgg tctgcgattc cgactcgtcc aacatcaata aacctatta    2580 atttcccctc gtcaaaaata aggttatcaa gtgagaaatc accatgagtg acgactgaat    2640
ccggtgagaa tggcaaaagt ttatgcattt cttttccagac ttgttcaaca ggccagccat    2700
tacgctcgtc atcaaaatca ctcgcatcaa ccaaaccgtt attcattcgt gattgcgcct    2760
gagcgagacg aaatacgcga tcgctgttaa aaggacaatt acaaacagga tcgaatgca    2820 accggcgcag gaacactgcc agcgcatcaa caatattttc acctgaatca ggatattctt    2880
ctaatacctg gaatgctgtt tttccgggga tcgcagtggt gagtaaccat gcatcatcag    2940
gagtacggat aaaatgcttg atggtcggaa gaggcataaa ttccgtcagc cagtttagtc    3000
tgaccatctc atctgtaaca tcattggcaa cgctacctt gccatgtttc agaaacaact    3060
ctggcgcatc gggcttccca tacaatcgat agattgtcgc acctgattgc ccgacattat    3120
cgcgagccca tttataccca tataaatcag catccatgtt ggaatttaat gcggcctcg    3180 agcaagacgt ttcccgttga atatggctca taacacccct tgtattactg tttatgtaag    3240
cagacagttt tattgttcat gatgatatat ttttatcttg tgcaatgtaa catcagagat    3300
tttgagacac aattcatcga tgatggttga gatgtgtata agagacagat tattgaagca    3360
tttatcaggg ttattgtctc atgagcggat acatatttga atgtatttag aaaaataaac    3420
aaataggggt tccgcgcaca tttccccgaa aagtgccacc tgacgtctaa gaaaccatta    3480
ttatcatgac attaacctat aaaaataggc gtatcacgag gccctttcgt c            3531
```

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
gtcccctcca ccccacagtg                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
ggggccacta gggacaggat                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
gcgacgtaaa cggccacaag                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
gtccatgccg agagtgatcc                                          20

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6
acttcttcaa gtccgccatg ccc                                      23

<210> SEQ ID NO 7
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 7
atgttgccgt cctccttgaa gtcg                                     24

<210> SEQ ID NO 8
<211> LENGTH: 250
<212> TYPE: DNA
<213> ORGANISM: Artificial Sequence
<220> FEATURE:
<223> OTHER INFORMATION: Synthetic Oligonucleotide -continued

```
<400> SEQUENCE: 8
tcagccgcta ccccgaccac atgaagcagc acgacttctt caagtccgcc atgcccgaag      60
gctacgtcca ggagcgcacc atcttcttca aggacgacgg caactacaag acctaagtcc     120
cctccacccc acagtggggc cactagggac aggattggtg acagaaaagc gcgccgaggt     180
gaagttcgag ggcgacaccc tggtgaaccg catcgagctg aagggcatcg acttcaagga     240
ggacggcaac                                                            250
```

METHODS, COMPOSITIONS AND KITS FOR INCREASING GENOME EDITING EFFICIENCY

CROSS-REFERENCE TO RELATED APPLICATIONS

This application is a divisional application of U.S. patent application Ser. No. 16/317,314, filed Jan. 11, 2019, which is a 35 U.S.C. § 371 National Stage Application of International Application No. PCT/US17/41979, filed Jul. 13, 2017, which claims benefit of, and priority to, U.S. Provisional Application No. 62/361,781, filed on Jul. 13, 2016, and U.S. Provisional Application No. 62/361,961, filed on Jul. 13, 2016, the contents of each of which is incorporated herein, in their entireties.

INCORPORATION-BY-REFERENCE OF SEQUENCE LISTING

The contents of the file named "VPI_16-114US_ST25.txt", which was created on Jun. 11, 2021 and is 6.64 KB in size, are hereby incorporated by reference in their entirety.

FIELD OF THE INVENTION

This invention relates generally to methods, compositions and kits for increasing genome editing efficiency by administering a DNA protein-kinase (DNAPK) inhibitor and a genome editing system to a cell(s).

BACKGROUND OF THE INVENTION

Precise genome targeting technologies are needed to enable systematic engineering of genetic variations. The use of genome editing systems, specifically CRISPR-endonuclease based genome editing technology has grown exponentially in the past few years. The type II CRISPR-Cas9 bacterial innate immune system has emerged as an effective genome editing tool for targeted modification of the human genome (Wiedenheft, B. 2012; Hsu, P. D. eta. 2014). Recently, CRISPR-Cpf genome editing systems have been described. CRISPR-endonuclease based genome editing is dependent, in part, upon non-homologous end joining (NHEJ) and homology directed repair (HDR) pathways to repair DNA double strand breaks. Cellular repair mechanism favors NHEJ over HDR.

While the achievement of insertion or deletions (indels) from NHEJ is up to 70% effective in some reports, the efficiency of HDR remains challenging, with rates at less than 1%.

Accordingly, a need exists for increasing genome editing efficiency, in particular, HDR efficiency.

SUMMARY OF THE INVENTION

The present invention can improve HDR efficiency by suppressing NHEJ enzymes such as DNAPK using DNAPK inhibitors.

In some embodiments, the disclosure provides a method of editing one or more target genomic regions, the method includes administering to one or more cells that have one or more target genomic regions, a genome editing system and a compound represented by Structural Formula (I) or Structural Formula (I'):

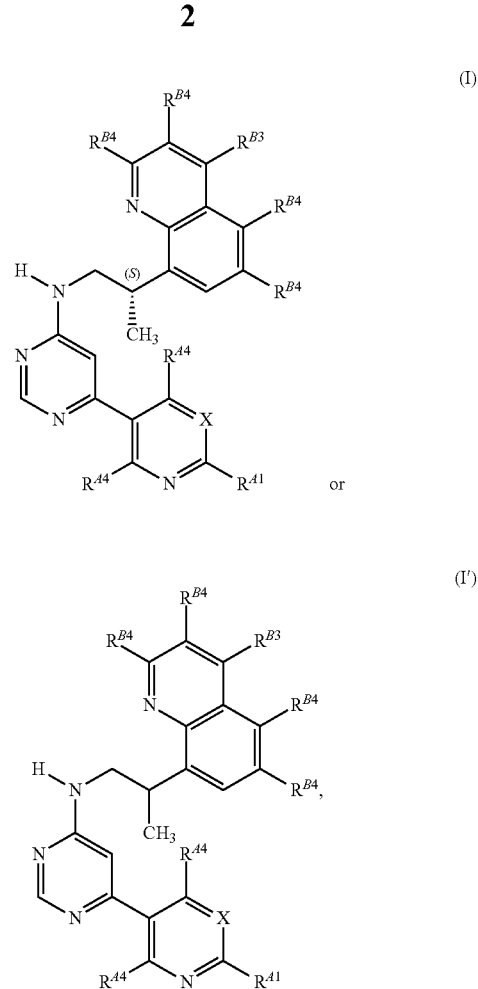

or a pharmaceutically acceptable salt or a co-crystal thereof.

X is N, $CR^{A5}$.

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyranyl, or morpholinyl, and each of said alkyl, cycloalkyl, or heterocyclyl is optionally substituted with up to three F atoms, up to three $^2H$ atoms, up to two non-geminal OH groups, or up to two $OC_{1-2}$alkyl.

Each $R^{A4}$ is, independently, H or $^2H$.

$R^{A5}$ is hydrogen, F, $C_{1-4}$alkyl, or $OC_{1-4}$alkyl, wherein each of said alkyl is optionally substituted with up to three F atoms or up to three $^2H$ atoms.

$R^{B3}$ is $C(O)NHC_{1-4}$ alkyl, wherein said alkyl is optionally substituted with up to three F atoms, up to three $^2H$ atoms, up to two non-geminal OH groups, or up to two $OC_{1-2}$ alkyl.

Each $R^{B4}$ is, independently, hydrogen, deuterium, F, or $C_{1-4}$alkyl.

In some embodiments, the disclosure also provides a method of repairing a DNA break in one or more target genomic regions via a homology directed repair (HDR) pathway, the method includes administering to one or more cells that have one or more target genomic regions, a genome editing system and a compound represented by Structural Formula (I) or Structural Formula (I')

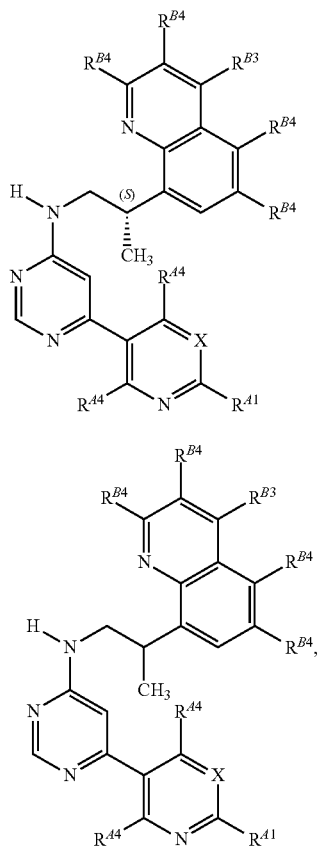

(I)

(I')

or a pharmaceutically acceptable salt or a co-crystal thereof.

X is N, $CR^{A5}$.

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$cycloalkyl, or $C_{0-4}$ alkyl-heterocyclyl, wherein said heterocyclic ring system is selected from oxetanyl, tetrahydrofuranyl, tetrahydropyranyl, or morpholinyl, and each of said alkyl, cycloalkyl, or heterocyclyl is optionally substituted with up to three F atoms, up to three $^2$H atoms, up to two non-geminal OH groups, or up to two $OC_{1-2}$alkyl.

Each $R^{A4}$ is, independently, H or $^2$H.

$R^{A5}$ is hydrogen, F, $C_{1-4}$alkyl, or $OC_{1-4}$alkyl, wherein each of said alkyl is optionally substituted with up to three F atoms or up to three $^2$H atoms.

$R^{B3}$ is $C(O)NHC_{1-4}$alkyl, wherein said alkyl is optionally substituted with up to three F atoms, up to three $^2$H atoms, up to two non-geminal OH groups, or up to two $OC_{1-2}$alkyl.

Each $R^{B4}$ is, independently, hydrogen, deuterium, F, or $C_{1-4}$alkyl.

The genome editing system interacts with a nucleic acid(s) of the target genomic regions, resulting in a DNA break, and wherein the DNA break is repaired at least in part via a HDR pathway.

In some embodiments, the disclosure also provides a method of inhibiting or suppressing repair of a DNA break in one or more target genomic regions via a NHEJ pathway, the method includes administering to one or more cells that have one or more target genomic regions, a genome editing system and a compound represented by Structural Formula (I) or Structural Formula (I'):

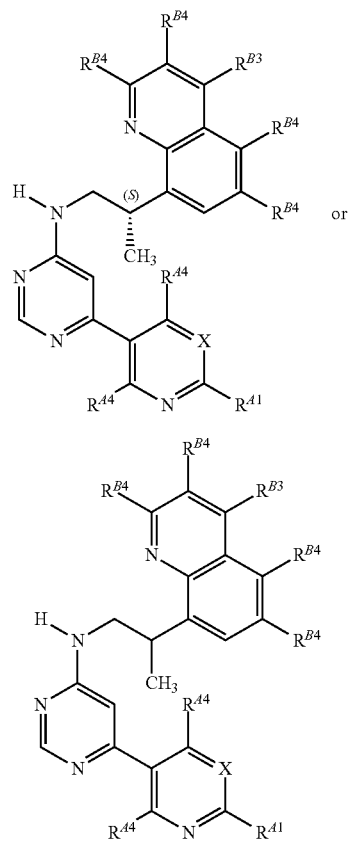

(I)

(I')

or a pharmaceutically acceptable salt or a co-crystal thereof.

X is N, $CR^{A5}$;

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyranyl, or morpholinyl, and each of said alkyl, cycloalkyl, or heterocyclyl is optionally substituted with up to three F atoms, up to three $^2$H atoms, up to two non-geminal OH groups, or up to two $OC_{1-2}$alkyl.

Each $R^{A4}$ is, independently, H or $^2$H;

$R^{A5}$ is hydrogen, F, $C_{1-4}$alkyl, or $OC_{1-4}$alkyl, wherein each of said alkyl is optionally substituted with up to three F atoms or up to three $^2$H atoms.

$R^{B3}$ is $C(O)NHC_{1-4}$ alkyl, wherein said alkyl is optionally substituted with up to three F atoms, up to three $^2$H atoms, up to two non-geminal OH groups, or up to two $OC_{1-2}$ alkyl.

Each $R^{B4}$ is, independently, hydrogen, deuterium, F, or $C_{1-4}$alkyl.

The genome editing system interacts with a nucleic acid(s) of the one or more target genomic regions, resulting in a DNA break, and wherein repair of the DNA break via a NHEJ pathway is inhibited or suppressed.

In some embodiments, the disclosure also provides a method of modifying expression of one or more genes or proteins, the method includes administering to one or more cells that comprise one or more target genomic regions, a genome editing system and a compound represented by Structural Formula (I) or Structural Formula (I'):

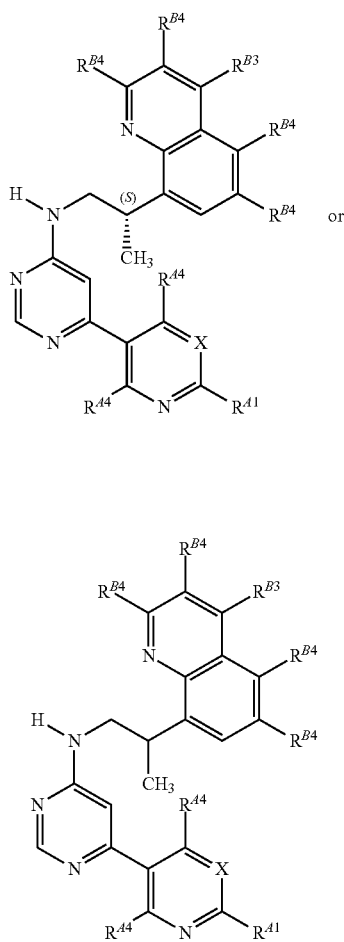

(I)

(I')

or a pharmaceutically acceptable salt or a co-crystal thereof.

X is N, CR$^{A5}$.

R$^{A1}$ is F, C$_{1-4}$alkyl, C$_{3-5}$cycloalkyl, OC$_{1-4}$alkyl, OC$_{1-4}$alkyl-C$_{3-5}$cycloalkyl, NH$_2$, NHC$_{1-4}$alkyl, NHC$_{1-4}$alkyl-C$_{3-5}$cycloalkyl, or C$_{0-4}$alkyl-heterocyclyl, wherein said heterocyclic ring system is selected from oxetanyl, tetrahydrofuranyl, tetrahydropyranyl, or morpholinyl, and each of said alkyl, cycloalkyl, or heterocyclyl is optionally substituted with up to three F atoms, up to three $^2$H atoms, up to two non-geminal OH groups, or up to two OC$_{1-2}$alkyl.

Each R$^{A4}$ is, independently, H or $^2$H.

R$^{A5}$ is hydrogen, F, C$_{1-4}$alkyl, or OC$_{1-4}$alkyl, wherein each of said alkyl is optionally substituted with up to three F atoms or up to three $^2$H atoms.

R$^{B3}$ is C(O)NHC$_{1-4}$ alkyl, wherein said alkyl is optionally substituted with up to three F atoms, up to three $^2$H atoms, up to two non-geminal OH groups, or up to two OC$_{1-2}$alkyl; and each R$^{B4}$ is, independently, hydrogen, deuterium, F, or C$_{1-4}$alkyl.

The genome editing system interacts with a nucleic acid(s) of the one or more target genomic regions of a target gene(s), resulting in editing the one or more target genomic regions and wherein the edit modifies expression of a downstream gene (s) and/or protein(s) associated with the target gene(s).

In some embodiments, the DNA break includes a DNA double strand break (DSB).

In some embodiments, the compound is a co-crystal that includes a compound having a structure of Formula (I) or Formula (I') and a co-crystal former selected from adipic acid, citric acid, fumaric acid, maleic acid, succinic acid, or benzoic acid.

In some embodiments, the compound is represented by Structural Formula (II), Structural Formula (II'), Structural Formula (II''), or Structural Formula (II'''):

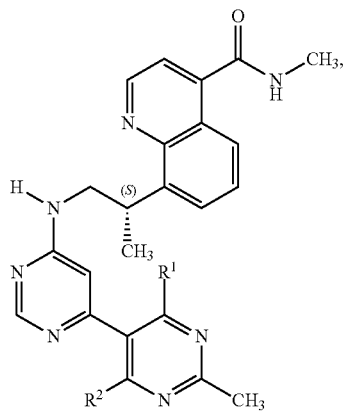

(II)

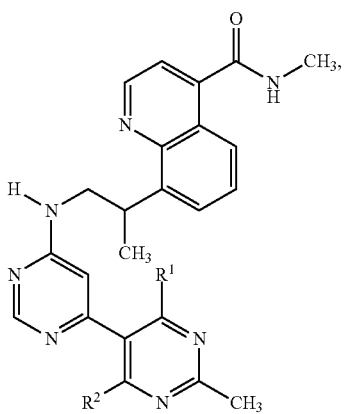

(II')

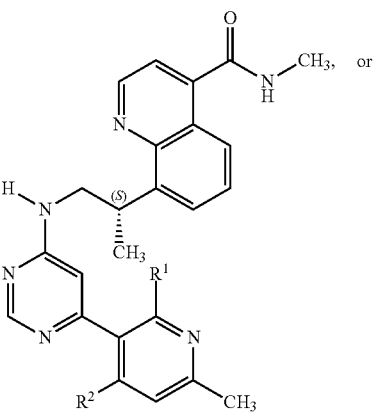

(II''), or

-continued

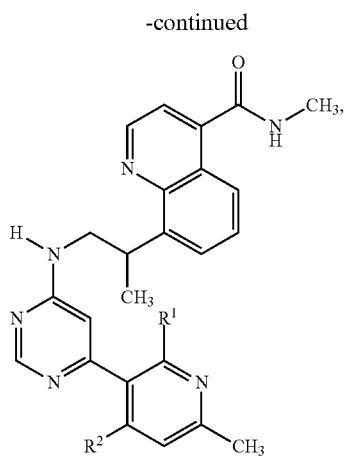

(II''')

or a pharmaceutically acceptable salt thereof or co-crystals thereof, wherein each of $R^1$ and $R^2$ is independently hydrogen or deuterium.

In some embodiments, the compound is a co-crystal that includes a compound having a structure of Formula (II), Formula (II'), Formula (II'') or Formula (II'''); and a co-crystal former selected from adipic acid, citric acid, fumaric acid, maleic acid, succinic acid, or benzoic acid.

In some embodiments, the efficiency of editing the target genomic regions in the one or more cells is increased as compared to that in otherwise identical cell or cells but without the compound.

In some embodiments, the efficiency of the repair of the DNA break at the target genomic regions in the one or more cells via a HDR pathway is increased as compared to that in otherwise identical cell or cells but without the compound.

In some embodiments, the efficiency of inhibiting or suppressing the repair of the DNA break at the target genomic regions in the one or more cells via a NHEJ pathway is increased as compared to that in otherwise identical cell or cells but without the compound.

In some embodiments, the efficiency is increased by at least 2-fold, 3-fold, 4-fold, 5-fold, 10-fold, 15-fold, 20-fold, 25-fold, 30-fold, 40-fold, 50-fold, or 100-fold as compared to that in otherwise identical cell or cells but without compound.

In some embodiments, the efficiency is measured by frequency of targeted polynucleotide integration. In some embodiments, the efficiency is measured by frequency of targeted mutagenesis. In some embodiments, the targeted mutagenesis comprises point mutations, deletions, and/or insertions.

In some embodiments, the expression of a downstream gene (s) and/or protein(s) associated with the target gene(s) is increased as compared to the baseline expression level in the one or more cells prior to the administration. For example, said expression is increased by at least 10%, 20%, 30%, 40%, 50%, 60%, 70%, 80%, 90%, 1-fold, 1.5-fold, 2-fold, 2.5-fold, 3-fold, 3.5-fold, 4-fold, 4.5-fold, 5-fold, or 10-fold as compared to the baseline expression level in the one or more cells prior to the administration.

In some embodiments, the expression of a downstream gene (s) and/or protein(s) associated with the target gene(s) is decreased as compared to the baseline expression level in the one or more cells prior to the administration. For example, the gene expression is decreased by at least 10%, 20%, 30%, 40%, 50%, 60%, 70%, 80%, 90%, 95%, 96%, 97%, 98%, or 99% as compared to the baseline expression level in the one or more cells prior to the administration.

In some embodiments, the expression of a downstream gene (s) and/or protein(s) associated with the target gene(s) is substantially eliminated in the one or more cells.

In some embodiments, the cell is synchronized at the S or the G2 cell cycle phase.

In some embodiments, the one or more cells that are administered or contacted with said compound have increased survival in comparison to one or more cells that have not been administered or contacted with said compound.

In some embodiments, the genome editing system and the compound are administered into the one or more cells simultaneously. In some embodiments, the genome editing system and the compound are administered into the one or more cells sequentially. In some embodiments, the genome editing system is administered into the one or more cells prior to the compound. In some embodiments, the compound is administered into the one or more cells prior to the genome editing system.

In some embodiments, the one or more cells are cultured cells. In some embodiments, the one or more cells are in vivo cells within an organism. In some embodiments, the one or more cells are ex vivo cells from an organism.

In some embodiments, the organism is a mammal. In some embodiments, the organism is a human.

In some embodiments, the genome editing system and the compound are administered via a same route. In some embodiments, the genome editing system and the compound are administered via a different route. In some embodiments, the genome editing system is administered intravenously and the compound is administered orally.

In some embodiments, the genome editing system is selected from a meganuclease based system, a zinc finger nuclease (ZFN) based system, a Transcription Activator-Like Effector-based Nuclease (TALEN) system, a CRISPR-based system, or a NgAgo-based system.

In some embodiments, the genome editing system is a CRISPR-based system. In some embodiments, the CRISPR-based system is a CRISPR-Cas system or a CRISPR-Cpf system.

In some embodiments, the CRISPR-based system is a CRISPR-Cas system and wherein the CRISPR-Cas system includes: (a) at least one guide RNA element that includes: (i) a targeter RNA that includes a nucleotide sequence substantially complementary to a nucleotide sequence at the one or more target genomic regions or a nucleic acid that includes a nucleotide sequence(s) encoding the targeter RNA; (ii) and an activator RNA that includes a nucleotide sequence that is capable of hybridizing with the targeter RNA or a nucleic acid that includes a nucleotide sequence(s) encoding the activator RNA; and (b) a Cas protein element that includes a Cas protein or a nucleic acid that includes a nucleotide sequence(s) encoding the Cas protein.

In some embodiments, the targeter RNA and activator RNA are fused as a single molecule.

In some embodiments, the Cas protein is a Type-II Cas9 protein. In some embodiments, the Cas9 protein is a SaCas9, SpCas9, SpCas9n, Cas9-HF, Cas9-H840A, FokI-dCas9, or D10A nickase, or any combinations thereof.

In some embodiments, the CRISPR-based system is a CRISPR-Cpf system and the CRISPR-Cpf system includes: (a) at least one guide RNA element or a nucleic acid that includes a nucleotide sequence(s) encoding the guide RNA element, the guide RNA that includes a targeter RNA that that includes a nucleotide sequence substantially complementary to a nucleotide sequence at the one or more target genomic regions; and (b) a Cpf protein element that includes a Cpf protein or a nucleic acid comprising a nucleotide sequence encoding the Cpf protein.

In some embodiments, the genome editing system is delivered by one or more vectors.

In some embodiments, the one or more vectors are selected from viral vectors, plasmids, or ssDNAs.

In some embodiments, the viral vectors are selected from retroviral, lentiviral, adenoviral, adeno-associated and herpes simplex viral vectors.

In some embodiments, the genome editing system is delivered by synthetic RNA.

In some embodiments, the genome editing system is delivered by a nano formulation.

In some embodiments, the compound is:

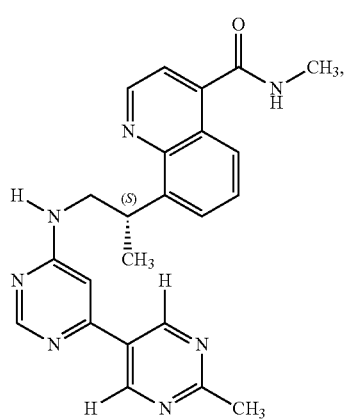

(Compound 1)

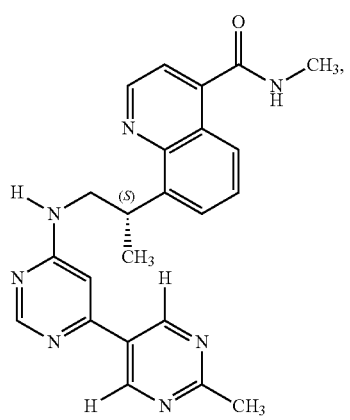

(Compound 2)

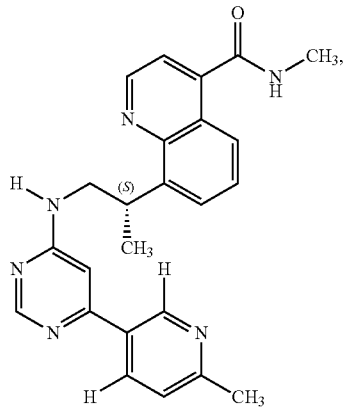

(Compound 3)

or a or pharmaceutically acceptable salt thereof.

In some embodiments, the compound is a co-crystal that includes:

(a) Compound 1 or Compound 2; and (b) adipic acid:

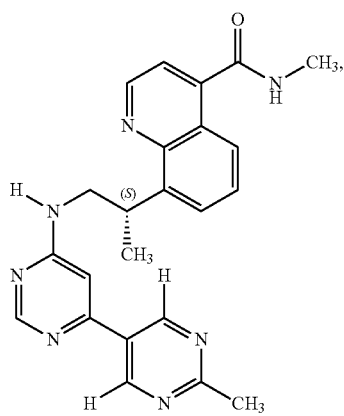

(Compound 1)

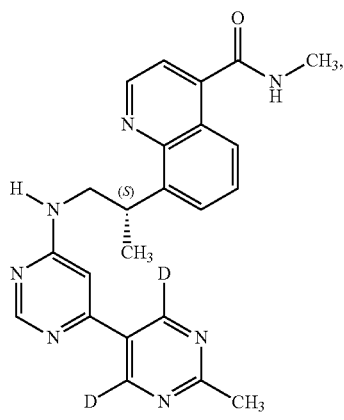

(Compound 2)

In some embodiments, the compound is a co-crystal that includes:

(a) Compound (1); and (b) adipic acid:

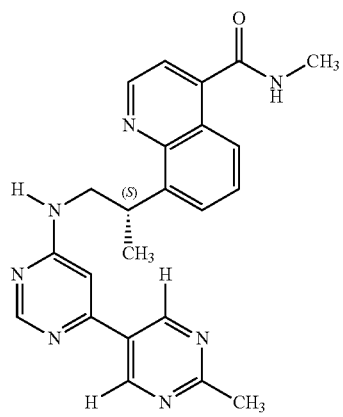

(Compound 1)

wherein the molar ratio of adipic acid to Compound (1) is about Z to 1.

In some embodiments, the compound is a co-crystal that includes:

(a) Compound (2); and (b) adipic acid:

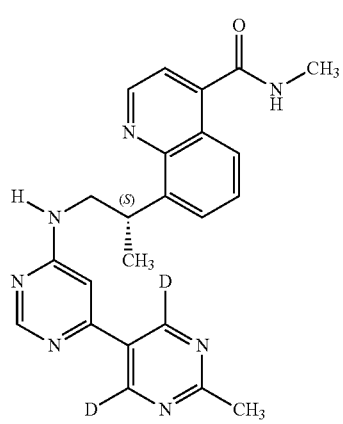

(Compound 2)

Wherein the molar ratio of adipic acid to Compound (2) is about 2 to 1.

In some embodiments, a kit or composition is provided for editing one or more target genomic regions. In some embodiments, the kit or composition includes a genome editing system; and a compound represented by Structural Formula (I) or Structural Formula (I'):

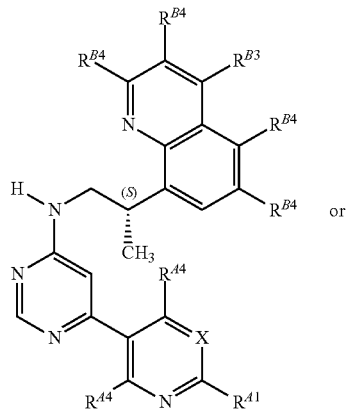

(I)

or

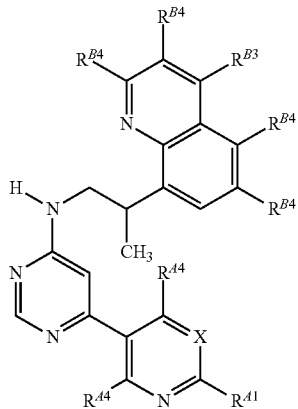

(I')

or a pharmaceutically acceptable salt or a co-crystal thereof.

X is N, $CR^{A5}$.

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, NH2, $NHC_{1-4}$alkyl, $NHC_{1-4}$alkyl-$C_{3-5}$cycloalkyl, or $C_{0-4}$alkyl-heterocyclyl, wherein said heterocyclic ring system is selected from oxetanyl, tetrahydrofuranyl, tetrahydropyranyl, or morpholinyl, and each of said alkyl, cycloalkyl, or heterocyclyl is optionally substituted with up to three F atoms, up to three $^2$H atoms, up to two non-geminal OH groups, or up to two $OC_{1-2}$alkyl.

Each $R^{A4}$ is, independently, H or $^2$H.

$R^{A5}$ is hydrogen, F, $C_{1-4}$alkyl, or $OC_{1-4}$alkyl, wherein each of said alkyl is optionally substituted with up to three F atoms or up to three $^2$H atoms.

$R^{B3}$ is $C(O)NHC_{1-4}$alkyl, wherein said alkyl is optionally substituted with up to three F atoms, up to three $^2$H atoms, up to two non-geminal OH groups, or up to two $OC_{1-2}$alkyl; and each $R^{B4}$ is, independently, hydrogen, deuterium, F, or $C_{1-4}$alkyl.

In some embodiments, the compound of the kit or composition is represented by Structural Formula (II), Structural Formula (II'), Structural Formula (II''), or Structural Formula (II'''):

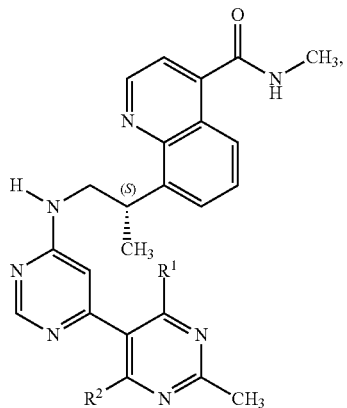
(II)

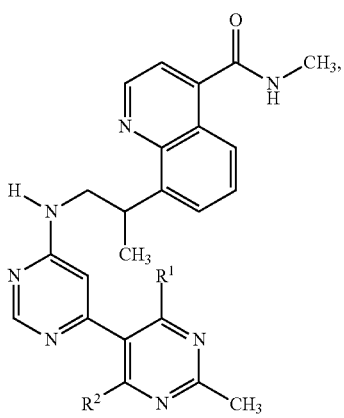
(II')

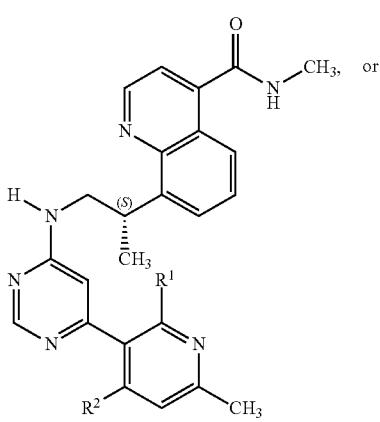
(II'')  or

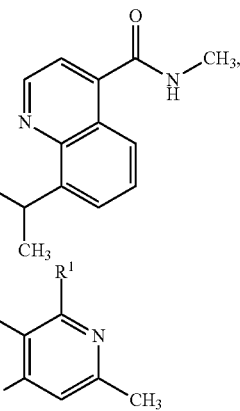
(II''')

or a pharmaceutically acceptable salt thereof or a co-crystal thereof, wherein each of $R^1$ and $R^2$ is hydrogen or deuterium.

In some embodiments, the genome editing system of the kit or composition is a meganuclease based system, a zinc finger nuclease (ZFN) based system, a Transcription Activator-Like Effector-based Nuclease (TALEN) system, a CRISPR-based system, or NgAgo-based system. In some embodiments, the genome editing system of the kit or composition is a CRISPR-based system. In some embodiments, the CRISPR-based system of the kit or composition is a CRISPR-Cas system or a CRISPR-Cpf system.

In some embodiments, the CRISPR-based system of the kit or composition is a CRISPR-Cas system and wherein the CRISPR-Cas system includes: (a) at least one guide RNA element that includes: (i) a targeter RNA that includes a nucleotide sequence substantially complementary to a nucleotide sequence at the one or more target genomic regions or a nucleic acid that includes a nucleotide sequence(s) encoding the targeter RNA; (ii) and an activator RNA that includes a nucleotide sequence that is capable of hybridizing with the targeter RNA, or a nucleic acid that includes a nucleotide sequence(s) encoding the activator RNA; and (b) a Cas protein element that includes a Cas protein or a nucleic acid that includes a nucleotide sequence(s) encoding the Cas protein.

In some embodiments, the Cas protein of the kit or composition is a Type-II Cas9 protein. In some embodiments, the Cas9 protein of the kit or composition is a SaCas9, SpCas9, SpCas9n, Cas9-HF, Cas9-H840A, FokI-dCas9, or D10A nickase, or any combination thereof.

In some embodiments, the CRISPR-based system of the kit or composition is a CRISPR-Cpf system, and wherein the CRISPR-Cpf system includes: (a) a targeter RNA that includes a nucleotide sequence substantially complementary to a nucleotide sequence at the one or more target genomic regions, or a nucleic acid that includes a nucleotide sequence(s) encoding the targeter RNA; and (b) a Cpf protein element that includes a Cpf protein or a nucleic acid that includes a nucleotide sequence(s) encoding the Cpf protein.

In some embodiments, the genome editing system of the kit or composition is included or packaged in one or more vectors. In some embodiments, the one or more vectors are selected from viral vectors, plasmids, or ssDNAs. In some embodiments, the viral vectors are selected from the group consisting of retroviral, lentiviral, adenoviral, adeno-associated and herpes simplex viral vectors.

In some embodiments, the compound of the kit or composition is:

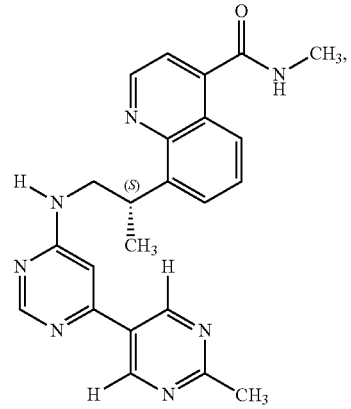
(Compound 1)

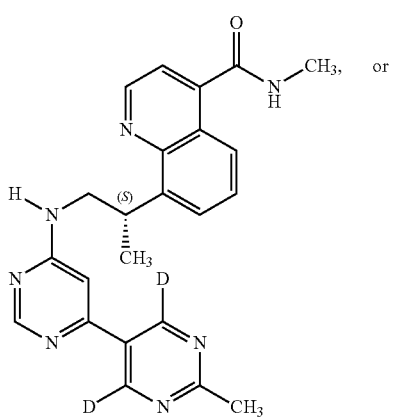
(Compound 2) or

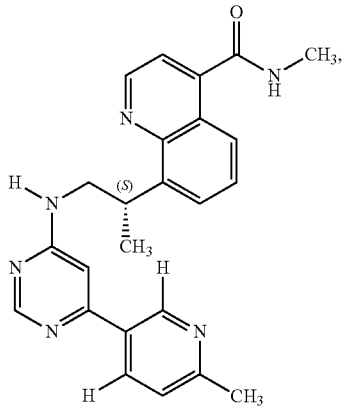
(Compound 3)

or a pharmaceutically acceptable salt thereof.

In some embodiments, the compound of the kit or composition is a co-crystal including a compound having a structure of Formula (I) or Formula (II) and a co-crystal former selected from adipic acid, citric acid, fumaric acid, maleic acid, succinic acid, or benzoic acid.

In some embodiments, the compound of the kit or composition is a co-crystal that includes: (a) Compound 1 or Compound 2; and (b) adipic acid:

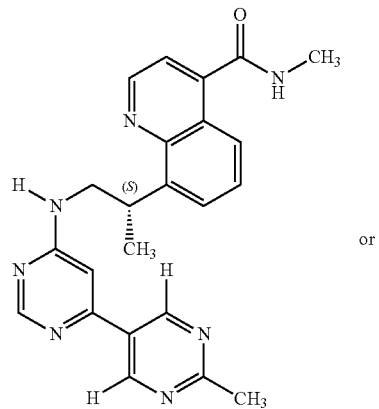
(Compound 1) or

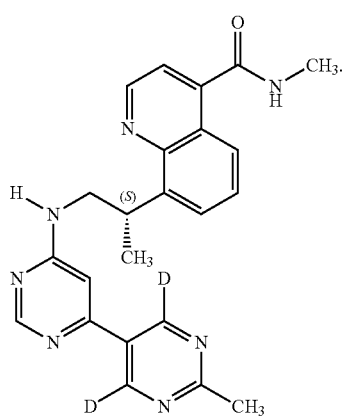
(Compound 2)

In some embodiments, the compound of the kit or composition is a co-crystal that includes: (a) Compound (1); and (b) adipic acid:

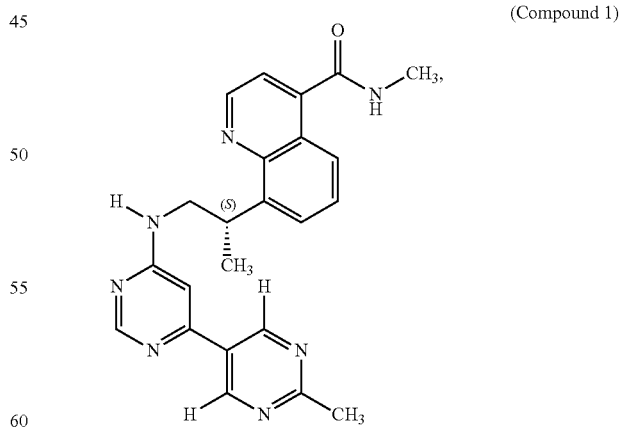
(Compound 1)

wherein the molar ration of adipic acid to Compound (1) is about 2 to 1.

In some embodiments, the compound of the kit or composition is a co-crystal that includes: (a) Compound (2); and (b) adipic acid:

(Compound 2)

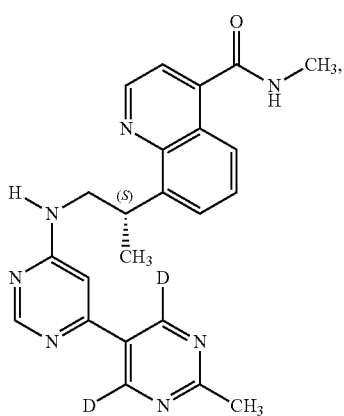

wherein the molar ration of adipic acid to Compound (2) is about 2 to 1.

Other features, objects, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE DRAWINGS

FIG. 1A depicts the design of a bicistronic construct targeting the human AAVS1 locus (SBI).

FIG. 1B depicts the cell line, and the targeted polynucleotide region (SEQ ID NO: 8), used in the traffic light reporter assay for monitoring HDR efficiency.

FIG. 1C is a schematic of the experimental workflow used in the traffic light reporter assay for monitoring HDR efficiency.

FIG. 2A is a series of representative FACS dot plot graphs of HEK293-EGIP after nucleofection. The FACS dot plot graphs depict the following conditions: nucleofection of dual expression gRNA-Cas9 only, nucleofection of dual expression gRNA-Cas9 with donor repair template, nucleofection of dual expression gRNA-Cas9 with donor template and culture with a small molecule DNAPK inhibitor Compound 1, and nucleofection with gRNA-Cas9 with donor repair template and culture of the cells with the putative ligase IV inhibitor Scr7. The data indicated an increase in GFP positive cells from transfection of donor repair template vector and gRNA-Cas9 expression plasmids in the presence of NHEJ inhibitors Compound 1 and Scr7.

FIG. 2B is a bar graph that depicts quantitation of enhancement of HDR following transfection of donor repair template vector and gRNA-Cas9 expression plasmids in the presence of NHEJ inhibitors Compound 1 and Scr7.

FIG. 2C is a bar graph that depicts HDR values showing several fold-increase in HDR enhancement relative to those obtained for transfection with gRNA-Cas9 plus donor template without compound.

DETAILED DESCRIPTION

Figure 1A:
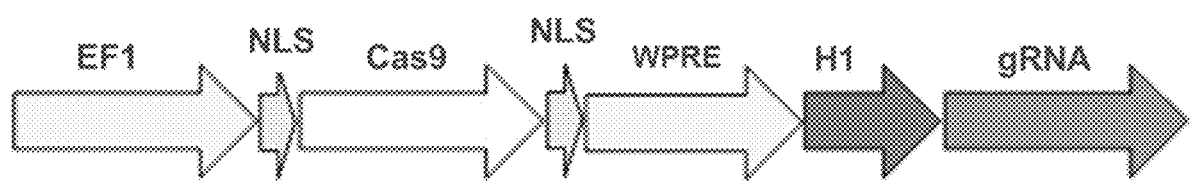
FIGS. 1A-1C are a series of schematics and sequences relating to the use of a traffic light reporter assay used for monitoring HDR efficiency.

Unless otherwise defined, scientific and technical terms used in connection with this disclosure shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout this disclosure. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. Generally, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference. As utilized in accordance with this disclosure, the terms defined in this disclosure, unless otherwise indicated, shall be understood to have the meanings as defined herein.

In some embodiments, this disclosure provides methods, compositions and kits for editing a target genome, e.g., by correcting a mutation. Such methods, compositions and kits can increase genome editing efficiency by the use of a DNAPK inhibitor.

A genomic editing system can stimulate or induce a DNA break(s), such as DSB(s) at the desired locus in the genome (or target genomic region). The creation of DNA cleavage prompts cellular enzymes to repair the site of break through either the error prone NHEJ pathway or through the error-free HDR pathway. In NHEJ, the DNA lesion is repaired by fusing the two ends of the DNA break in a series of enzymatic processes involving Ku70/80 heterodimer and DNA dependent protein kinase (DNAPK) enzymes. The repair mechanism involves tethering and alignment of two DNA ends, resection, elongation and ligation (Rouet et al.; Dexheimer T. DNA repair pathways and mechanisms. In: Mathews L, Cabarcas S, Hurt E, editors. DNA repair of cancer stem cells. Dordrecht: Springer; 2013. p. 19-32) resulting in the formation of small insertion or deletion mutations (indels) at the break site. Indels introduced into the coding sequence of a gene can cause either premature stop codon or frame-shift mutations that lead to the production of nonfunctional, truncated proteins. The mechanism of HDR pathway is less understood and involves a different set of repair proteins such as Rad51 that stimulate strand invasion by a donor repair template for base insertion or gene replacement. Hence, HDR allows introduction of exogenous DNA template to obtain a desired outcome of DNA editing within a genome and can be a powerful strategy for translational disease modeling and therapeutic genome editing to restore gene function.

Of the two DNA repair pathways, NHEJ occurs at a much higher frequency and reports of more than 70% efficiency can be achieved even in neurons (Swiech et al., "In vivo interrogation of gene function in the mammalian brain using CRISPR-Cas9," Nat Biotechnol. 2015 January; 33(1):102-62014). The HDR gene correction however, occurs at very low frequency and during S and G2 phase when DNA replication is completed and sister chromatids are available to serve as repair templates (Heyer et al., Regulation of homologous recombination in eukaryotes. Annual Review of Genetics 44:113-139, 2010). Since NHEJ occurs throughout the cell cycle, in competition and is favored over HDR during the S and G2 phase, targeted insertion through the HDR pathway remains a challenge and a focus of continued studies.

DNA protein-kinase (DNAPK) plays a role in various DNA repair processes. DNAPK participates in DNA double-stranded break repair through activation of the nonhomologous end-joining (NHEJ) pathway. NHEJ is thought to proceed through three steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-dependent protein kinase catalytic subunit (DNAPKcs) to adjacent sides of the DSB; this serves to protect the broken termini until additional processing enzymes are recruited. Recent data supports the hypothesis that DNAPKcs phosphorylates the processing enzyme, Artemis, as well as itself to prepare the DNA ends for additional processing. In some cases DNA polymerase may be required to synthesize new ends prior to the ligation step. The auto-phosphorylation of DNAPKcs is believed to induce a conformational change that opens the central DNA binding cavity, releases DNAPKcs from DNA, and facilitates the ultimate re-ligation of the DNA ends.

In some embodiments, this disclosure provides methods, compositions, and kits to enhance gene editing, in particular increasing the efficiency of repair of DNA break(s) via a HDR pathway, or the efficiency of inhibiting or suppressing repair of DNA break(s) via a NHEJ pathway, in genome editing systems, including CRISPR-based HDR repair in cells. While not being bound by a particular theory, it is believed that a genome editing system administered to a cell(s) interacts with a nucleic acid(s) of the target gene, resulting in or causing a DNA break; such DNA break is repaired by several repair pathways, e.g., HDR, and a DNAPK inhibitor administered to a cell(s) inhibits, blocks, or suppresses a NHEJ repair pathway, and the frequency or efficiency of HDR DNA repair pathway can be increased or promoted.

The interaction between a genome editing system with a nucleic acid(s) of the target gene can be hybridization of at least part of the genome editing system with the nucleic acid(s) of the target gene, or any other recognition of the nucleic acid(s) of the target gene by the genome editing system. In some embodiments, such interaction is a protein-DNA interactions or hybridization between base pairs.

In some embodiments, this disclosure provides methods of editing one or more target genomic regions in a cell(s) by administering to the cell(s) a genome editing system and a DNAPK inhibitor. The editing can occur simultaneously or sequentially. Editing of the one or more target genomic regions includes any kind of genetic manipulations or engineering of a cell's genome. In some embodiments, the editing of the one or more target genomic regions can include insertions, deletions, or replacements of genomic regions in a cell(s). Genomic regions comprise the genetic material in a cell(s), such as DNA, RNA, polynucleotides, and oligonucleotides. Genomic regions in a cell(s) also comprise the genomes of the mitochondria or chloroplasts contained in a cell(s).

In some embodiments, the insertions, deletions or replacements can be either in a coding or a non-coding genomic region, in intronic or exonic regions, or any combinations thereof including overlapping or non-overlapping segments thereof. As used herein, a "non-coding region" refers to genomic regions that do not encode an amino acid sequence. For example, non-coding regions include introns. Coding regions refer to genomic regions that code for an amino acid sequence. For example, coding regions include exons.

In some embodiments, the editing of one or more target genomic regions can occur in any one or more target regions in a genome of a cell(s). In some embodiments, the editing of one or more target genomic regions can occur, for example, in an exon, an intron, a transcription start site, in a promoter region, an enhancer region, a silencer region, an insulator region, an antirepressor, a post translational regulatory element, a polyadenylation signal (e.g. minimal poly A), a conserved region, a transcription factor binding site, or any combinations thereof.

In some embodiments, administration to a cell(s) with a DNAPK inhibitor and a genomic editing system results in increased targeted genome editing efficiency as compared to conditions in which a DNAPK inhibitor and a genomic editing system is not administered to a cell(s). In some embodiments, the increased editing efficiency is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNAPK inhibitor and a genome editing system is not administered to a cell(s), or compared to a condition in which only a genome editing system and not a DNAPK inhibitor is administered to a cell(s). The efficiency of genomic editing can be measured by any method known in the art, for example, by any method that ascertains the frequency of targeted polynucleotide integration or by measuring the frequency of targeted mutagenesis. Targeted polynucleotide integrations can also result in alteration or replacement of a sequence in a genome, chromosome or a region of interest in cellular chromatin. Targeted polynucleotide integrations can result in targeted mutations including, but not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

In some embodiments, the methods of editing one or more target genomic regions in a cell(s) involve administering to the cell(s) a genome editing system and a DNAPK inhibitor. In some embodiments, the cell(s) is synchronized at the S or the G2 cell cycle phase. Synchronization of the cell(s) at the S or G2 cell cycle phase can be achieved by any method known in the art. As a non-limiting example, agents that can be used to synchronize a cell(s) at the S or G2 cell cycle phase include aphidicolin, dyroxyurea, lovastatin, mimosine, nocodazole, thymidine, or any combinations thereof. (See, Lin et al. "Enhanced homology-directed human genome engineering by controlled timing of CRISPR/Cas9 delivery," *Elife*. 2014 Dec. 15; 3). In some embodiments, the agents for cell synchronization can be administered at any time during the gene-editing process. In some embodiments, a cell(s) can be synchronized at the S or the G2 phase of the cell cycle before, during, or after administering to a cell(s) a genome editing system and/or a DNAPK inhibitor.

In some embodiments, the methods of editing one or more target genomic regions in a cell(s) by administering to the cell(s) a genome editing system and a DNAPK inhibitor results in increased cell survival in comparison to conditions in which a genome editing system and a DNAPK inhibitor were not administered to a cell(s), or in comparison to conditions in which only a gene editing system is contacted or administered into a cell(s) and not a DNAPK inhibitor.

In some embodiments, provided herein are methods of repairing a DNA break in one or more target genomic regions via an HDR pathway. The administering to a cell(s) a genome editing system and a DNAPK inhibitor results in a DNA break of a targeted region of the genome, and the DNA break is subsequently repaired, at least in part, by a HDR pathway. These methods result in increased amounts of HDR-mediated repair (e.g. HDR pathway) in the one or more target genomic regions resulting in greater efficiency of HDR-mediated repair as compared to conditions in which a DNAPK inhibitor and a genomic editing system is not administered to a cell(s). In some embodiments, the efficiency of HDR pathway mediated repair of the DNA break is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNAPK inhibitor and a genome editing system is not administered to a cell(s), or compared to a condition in which only a genome editing system and not a DNAPK inhibitor is administered to a cell(s). The efficiency of HDR pathway mediated repair can be measured by any method known in the art, for example, by ascertaining the frequency of targeted polynucleotide integration or by measuring the frequency of targeted mutagenesis.

In some embodiments, the methods herein provide for repairing the DNA break by increasing the efficiency of the HDR pathway.

The HDR pathway can be "canonical" or "alternative." "HDR" (homology directed repair) refers to a specialized form of DNA repair that takes place, for example, during repair of double-strand breaks or a DNA nick in a cell(s). HDR of double stranded breaks is generally based on nucleotide sequence homology, uses a "donor" molecule to template repair of a "target" molecule (e.g., the one that experienced the double-strand break), and can lead to the transfer of genetic information from the donor to the target. Canonical HDR of double stranded breaks is generally based on BRCA2 and RAD51 and typically employs a dsDNA donor molecule. Non-canonical, or "alternative," HDR is an HDR mechanism that is suppressed by BRCA2, RAD51, and/or functionally-related genes. Alternative HDR may use a ssDNA or nicked dsDNA donor molecule. See, for example, WO 2014172458.

In some embodiments, the methods of repairing a DNA break in one or more target genomic regions via an HDR pathway by administering to the cell(s) a genome editing system and a DNAPK inhibitor result in increased cell survival in comparison to conditions in which a genome editing system and a DNAPK inhibitor are not administered to a cell(s), or in comparison to conditions in which only a gene editing system is administered to a cell(s) and not a DNAPK inhibitor.

In some embodiments, provided herein are methods of inhibiting or suppressing NHEJ-mediated repair of a DNA break in one or more target genomic regions in a cell(s). In some embodiments, the inhibiting or suppressing of NHEJ-mediated repair of a DNA break is performed by inhibiting or suppressing the NHEJ pathway. The NHEJ pathway can be either classical ("canonical") or an alternative NHEJ pathway (alt-NHEJ, or microhomology-mediated end joining (MMEJ)). The NHEJ pathway or alt-NHEJ pathway is suppressed in a cell(s) by administering to a cell(s) a genome editing system and a DNAPK inhibitor.

The classical NHEJ repair pathway is a DNA double stranded break repair pathway in which the ends of the double stranded break are ligated without extensive homology. Classical NHEJ repair uses several factors, including KU70/80 heterodimer (KU), XRCC4, Ligase IV, and DNA protein kinases catalytic subunit (DNAPKcs). Alt-NHEJ is another pathway for repairing double strand breaks. Alt-NHEJ uses a 5-25 base pair microhomologous sequence during alignment of broken ends before joining the broken ends. Alt-NHEJ is largely independent of KU70/80 heterodimer (KU), XRCC4, Ligase IV, DNA protein kinases catalytic subunit (DNAPKcs), RAD52, and ERCC1. See, Bennardo et al., "Alternative-NHEJ is a Mechanistically Distinct Pathway of Mammalian Chromosome Break Repair," *PLOS Genetics*, Jun. 27, 2008.

In some embodiments, the methods of inhibiting or suppressing NHEJ-mediated repair of a DNA break via the NHEJ pathway in one or more target genomic regions in a cell(s) by inhibiting or suppressing the NHEJ pathway though the administering to a cell(s) a genomic editing system and a DNAPK inhibitor result in increased efficiency of inhibiting or suppressing the NHEJ-mediated repair of the DNA break in comparison to a cell(s) that have not received a genomic editing system and a DNAPK inhibitor, or in comparison to a condition in which a cell(s) receives a genomic editing system and not a DNAPK inhibitor. In some embodiments, the increased efficiency of inhibiting or suppressing repair of a DNA break via the NHEJ pathway by contacting a cell(s) with a DNAPK inhibitor and a genome editing system is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNAPK inhibitor and a genome editing system is not administered to a cell(s), or compared to a condition in which only a genome editing system and not a DNAPK inhibitor is administered to a cell(s). The efficiency inhibiting or suppressing repair of a DNA break via the NHEJ pathway can be measured by any method known in the art, for example, by ascertaining the frequency of targeted polynucleotide integration or by measuring the frequency of targeted mutagenesis.

In some embodiments, the methods of inhibiting or suppressing NHEJ-mediated repair of a DNA break in one or more target genomic regions in a cell(s) by inhibiting or suppressing the NHEJ pathway though the administering to a cell(s) a genomic editing system and a DNAPK inhibitor result in increased cell survival in comparison to conditions in which a genome editing system and a DNAPK inhibitor were not contacted or administered to a cell(s), or in comparison to conditions in which only a gene editing system is contacted or administered into a cell(s) and not a DNAPK inhibitor.

The DNA break can be a double stranded break (DSB) or two single stranded breaks (e.g. two DNA nicks). The DSB can be blunt ended or have either a 5' or 3' overhang, if the strands are each cleaved too far apart, the overhangs will continue to anneal to each other and exist as two nicks, not one DSB.

In some embodiments, provided herein are methods of modifying expression of one or more genes (a target gene(s)), and/or corresponding or downstream proteins, by administering to a cell(s) a genome editing system and a DNAPK inhibitor. In some embodiments, the genome editing system can create, for example, insertions, deletions, replacements, modification or disruption in a target genomic region(s) of a target gene(s) of the cell(s), resulting in modified expression of the target gene(s). In some embodiments, the insertion, deletions, replacement, modification or disruption can result in targeted expression of a specific protein, or group of proteins, or of downstream proteins. In some embodiments, the genome editing system can create insertions, deletions or replacements in non-coding regions or coding regions. In some embodiments, the genome editing system can create insertions, deletions, replacements, modification or disruption in a promoter region, enhancer region, and/or any other gene regulatory element, including an exon, an intron, a transcription start site, a silencer region, an insulator region, an antirepressor, a post translational regulatory element, a polyadenylation signal (e.g. minimal poly A), a conserved region, a transcription factor binding site, or any combinations thereof. In some embodiments, the genome editing system can create the insertions, deletions, replacements, modification or disruption in more than one target region, simultaneously or sequentially. In some embodiments, administering to a cell(s) with a genome editing system and a DNAPK inhibitor can allow for targeted modified gene expression in the cell(s). Such targeted modified gene expression can lead to expression of specific proteins and downstream proteins thereof.

In some embodiments, the expression of a downstream gene and/or protein is increased by at least 10%, 20%, 30%, 40%, 50%, 60%, 70%, 80%, 90%, 1, 1.5-fold, 2-fold, 2.5-fold, 3-fold, 3.5-fold, 4-fold, 4.5-fold, 5-fold, or 10-fold in comparison to a condition in which a DNAPK inhibitor and a genome editing system is not administered to a cell(s), or compared to a condition in which only a genome editing system and not a DNAPK inhibitor is administered to a cell(s).

In some embodiments, the gene expression of a downstream gene and/or protein is decreased by at least 10%, 20%, 30%, 40%, 50%, 60%, 70%, 80%, 90%, 95%, 96%, 97%, 98%, or 99% in comparison to a condition in which a DNAPK inhibitor and a genome editing system is not administered to a cell(s), or compared to a condition in which only a genome editing system and not a DNAPK inhibitor is administered to a cell(s).

The cell of the methods herein can be any cell. In some embodiments, the cell is a vertebrate cell. In some embodiments, the vertebrate cell is a mammalian cell. In some embodiment, the vertebrate cell is a human cell.

The cell can be any kind of cell at any developmental stage. In some embodiments, the cell can be a differentiated cell, a totipotent stem cell, a pluripotent stem cell, an embryonic stem cell, an embryonic germ cell, an adult stem cell, a precursor cell, an induced pluripotent stem cell, or any combinations thereof. A differentiated cell is a specialized cell that performs a specific function in a tissue. A totipotent stem cell is an undifferentiated cell from an embryo, fetus or adult that can divide for extended periods and has the capability of differentiating into any cell type of any of the three germ layers of an organism. A pluripotent stem cell is an undifferentiated cell from an embryo, fetus or adult that can divide for extended periods and has the capability of differentiating into any cell type of an organism except extraembryonic tissue or the placenta. An embryonic stem cell is an undifferentiated stem cell that is found in the inner cell mass of an embryo and has the capability to differentiate into any type of cell of any of the three germ layers. An embryonic germ cell is an embryonic cell that can give rise to reproductive cells, such as sperm cells or egg cells. An adult stem cell is an undifferentiated cell that is found in differentiated tissue, is capable of self-renewal and can differentiate into any of the cells of the tissue in which it resides. A precursor or progenitor cell is a partially differentiated cell which typically can only differentiate into one kind of cell (e.g. a unipotent cell). An induced pluripotent stem cell is a kind of pluripotent stem cell that is generated from an adult differentiated or partially differentiated cell. See, for example, WO/2010/017562.

As used herein, the singular form "a", "an" and "the" include plural references unless the context clearly dictates otherwise. For example, the term "a cell" includes a plurality of cells, including mixtures thereof. For example "one or more cells" and "a cell(s)" are interchangeably used herein. Similarly, "one or more target genomic regions" and "a target genomic region(s)" are interchangeably used herein.

The terms, "approximately" and "about" are used interchangeably herein. The term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The terms "polynucleotide", "nucleotide", "nucleotide sequence", "nucleic acid" and "oligonucleotide" are used interchangeably. They refer to a polymeric form of nucleotides of any length, either deoxyribonucleotides (DNA) or ribonucleotides (RNA), or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "ssDNA" means a single stranded DNA molecule. The term "ssODN" means single stranded oligodeoxynucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselerloate, phosphorodiselenoate, phosphoroanilothioate, phoshoranilate, phosphoronmidate, and the like. An oligonucleotide can include a label for detection, if desired.

The term "synthetic RNA" refers to RNA that is engineered or non-naturally occurring.

As used herein the term "wild type" is a term of the art understood by skilled persons and means the typical form of an organism, strain, gene or characteristic as it occurs in nature as distinguished from mutant or variant forms.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The term "agent" is used herein to denote a chemical compound, a small molecule, a mixture of chemical compounds, a biological macromolecule, or an extract made from biological materials.

The terms "subject," "individual," and "patient" are used interchangeably herein to refer to a vertebrate, such as a mammal, or a human. Mammals include, but are not limited to, murines, simians, humans, farm animals, sport animals, and pets.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. These terms also mean the treatment of a disease in a mammal, e.g., in a human, including (a) inhibiting the disease, i.e., arresting or preventing its development; (b) relieving the disease, i.e., causing regression of the disease state; or (c) curing the disease.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "administer" refers to contacting, injecting, dispensing, delivering, or applying a genomic editing system and/or a DNAPK inhibitor to a cell or a subject. In some embodiments, the administration is contacting a genomic editing system and/or a DNAPK inhibitor with a cell(s). In some embodiments, the administration is delivering a genomic editing system and/or a DNAPK inhibitor to a cell(s). In some embodiments, the administration is applying a genomic editing system and/or a DNAPK inhibitor to a cell(s). In some embodiments, the administration is injecting a genomic editing system and/or a DNAPK inhibitor to a cell(s). Administering can occur in vivo, ex vivo, or in vitro. Administering a genomic editing system and a DNAPK inhibitor to a cell(s) can be done simultaneously or sequentially.

The term "acquired" in reference to a condition or disease as used herein means a disorder or medical condition which develops post-fetally; in contrast with a congenital disorder, which is present at birth. A congenital disorder may be antecedent to an acquired disorder.

The terms "congenital" or "inherited" condition or disease is a genetic disorder found in the genome of a subject that is present in a subject at birth. The "genome" as used herein includes all of the genetic material in the nucleus and the cytoplasm, and further includes the mitochondrial genome and ribosomal genome. The congenital or inherited may be expressed at any time during the subject's life, for example at birth or at adulthood.

The term "genetic disorder" or "genetic disease" includes inherited or acquired mutations in the genome of a subject that causes or may cause disease.

The terms "polymorphisms" or "genetic variations" means different forms of a gene at a genetic locus.

A "viral vector" is defined as a recombinantly produced virus or viral particle that comprises a polynucleotide to be delivered into a host cell, either in vivo, ex vivo or in vitro. Examples of viral vectors include retroviral vectors, adenoviral vectors, adeno-associated virus vectors, adenoviral vectors, lentiviral vectors, herpes simplex viral vectors, and chimeric viral vectors and the like. In some embodiments s where gene transfer is mediated by a retroviral vector, a vector construct refers to the polynucleotide comprising the retroviral genome or part thereof.

Some embodiments of the disclosure relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells.

The cells can be primary cells, induced pluripotent stem cells (iPSCs), embryonic stem cells (hESCs), adult stem cells, progenitor cells or cell lines. "Primary cells" are cells taken directly from living tissue and placed in vitro for growth. Primary cells have few population doublings, and have a finite lifespan for population doublings in vitro. "Stem cells," "embryonic stem cells," and "induced pluripotent stem cells," are unspecialized and undifferentiated cells capable of self-renewal and having the potential to differentiate into cells of different types with specialized function. "Cell lines" include cell cultures that are derived from one cell type or a set of cells of the same type which can proliferate indefinitely. Non-limiting examples of mammalian cell lines can include CD34 cells, 293 cells, HEK cells, CHO cells, BHK cells, CV-1 cells, Jurkat cells, HeLa cells, or any variants thereof.

In some embodiments, a vector is capable of driving expression of one or more sequences in mammalian cells using a mammalian expression vector. Examples of mammalian expression vectors include pCDM8 and pMT2PC. When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. Other promoters can include, for example, EF1 promoter, or EF1 alpha promoter. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition). In some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition. In some embodiments, a substantially pure composition will comprise more than about 85%, 90%, 95%, and 99% of all macromolecular species present in the composition. In some embodiments, the object species is purified to essential homogeneity (contaminant species are not detected in the composition by conventional detection methods) wherein the composition consists essentially of a single macromolecular species.

Genome Editing System

Various types of genome engineering systems can be used. The terms "genome editing system," "gene editing system," and the like, are used interchangeably herein, and refer to a system or technology which edits a target gene or the function or expression thereof. A genome editing system comprises: at least one endonuclease component enabling cleavage of a target genomic region(s) (or target sequence(s)); and at least one genome-targeting element which brings or targets the endonuclease component to a target genomic region(s). Examples of genome-targeting element include a DNA-binding domain (e.g., zinc finger DNA-binding protein or a TALE DNA-binding domain), guide RNA elements (e.g., CRISPR guide RNA), and guide DNA elements (e.g., NgAgo guide DNA). Programmable genome-targeting and endonuclease elements enable precise genome editing by introducing DNA breaks, such as double strand breaks (DSBs) at specific genomic loci. DSBs subsequently recruit endogenous repair machinery for either non-homologous end-joining (NHEJ) or homology directed repair (HDR) to the DSB site to mediate genome editing. The "endonuclease component" comprises an endonuclease or a nucleic acid comprising a nucleotide sequence(s) encoding such endonuclease.

The term "endonuclease" refers to any wild-type, mutant, variant, or engineered enzyme capable of catalyzing the hydrolysis (cleavage) of a bond between nucleic acids within a DNA or RNA molecule. Endonucleases can recognize and cleave a DNA or RNA molecule at its target genomic regions. Examples of endonucleases include a homing endonuclease; restriction enzyme such as FokI; a chimeric Zinc-Finger nuclease (ZFN) resulting from the fusion of engineered zinc-finger domains with the catalytic domain of a restriction enzyme such as FokI; Cas enzymes, and Cpf enzymes. Chemical endonucleases in which a chemical or peptidic cleaver is conjugated either to a polymer of nucleic acids or to another DNA recognizing a specific target sequence, thereby targeting the cleavage activity to a specific sequence, are comprised in the term "endonuclease". Examples of chemical endonucleases include synthetic nucleases like conjugates of ortho-phenanthroline, a DNA cleaving molecule, and triplex-forming oligonucleotides (TFOs).

By "variant" it is intended a recombinant protein obtained by replacement of at least one residue in the amino acid sequence of the parent protein with a different amino acid.

In some embodiments, endonucleases such as ZFNs, TALENs and/or meganucleases comprise a cleavage domain and/or cleavage half-domain. The cleavage domain may be homologous or heterologous to the DNA-binding domain. For example, a zinc finger DNA-binding domain and a cleavage domain from a nuclease or a meganuclease DNA-binding domain and cleavage domain from a different nuclease can be used. Heterologous cleavage domains can be obtained from any endonuclease or exonuclease. Exemplary endonucleases from which a cleavage domain can be derived include, but are not limited to, restriction endonucleases and homing endonucleases. See, for example, WO2013/130824. Additional enzymes which cleave DNA are known (e.g., SI Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

A cleavage half-domain can be derived from any nuclease or portion thereof, as set forth above, that requires dimerization for cleavage activity. In some embodiments, two fusion proteins are required for cleavage if the fusion proteins comprise cleavage half-domains. In some embodiments, a single protein comprising two cleavage half-domains can be used. In some embodiments, the two cleavage half-domains can be derived from the same endonuclease (or functional fragments thereof). In some embodiments, each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-50 nucleotides, 5-8 nucleotides or by 15-18 nucleotides. It is noted that any integral number of nucleotides or nucleotide pairs can intervene between two target sites (e.g., from 2 to 50 nucleotide pairs or more). In some embodiments, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.

In some embodiments, the endonuclease component comprises a fusion protein(s) that include a cleavage domain (or cleavage half-domain) from at least one Type IIS restriction enzyme and one or more zinc finger binding domains, which may or may not be engineered. An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. The portion of the Fok I enzyme used in such fusion proteins is considered a cleavage half-domain. Thus, for targeted double-stranded cleavage and/or targeted replacement of cellular sequences using zinc finger- or TALE-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used.

Exemplary Type IIS restriction enzymes are described in International Publication WO 07/014275, incorporated herein in its entirety. Additional restriction enzymes also contain separable binding and cleavage domains, and these are contemplated by the disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and WO 2013/130824. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. See, e.g., U.S. Patent Publication No. 2008/0131962 and 2011/0201055. Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

The term "edit", "edits," "editing," and the like refer to any kind of engineering, altering, modifying or modulating (in each case which includes, but not limited to, by means of gene knockout, gene tagging, gene disruption, gene mutation, gene insertion, gene deletion, gene activation, gene silencing or gene knock-in).

As used herein, "genetic modification," "genome editing," "genome modification," "gene modification," and "gene editing," refer to any gene addition, deletion, knockout, knock-in, tagging, mutation, activation, silencing, modification, and/or disruption to a cell's nucleotides. The cell in this context can be in vitro, in vivo, or ex vivo.

By "target genomic region," "target gene," "DNA target", "DNA target sequence", "target sequence", "target nucleotide sequence", "target-site", "target", "site of interest", "recognition site", "polynucleotide recognition site", "recognition sequence", "cleavage site" is intended a polynucleotide sequence that is recognized and cleaved by a genome editing system. These terms refer to a distinct DNA location, preferably a genomic location, at which a DNA break (cleavage) is to be induced by the genome editing system.

The aforesaid editing, including engineering, altering, modifying and modulating, can occur simultaneously or sequentially. Any genome editing system known in the art can be used. In some embodiments, the genome editing system is a meganuclease based system, a zinc finger nuclease (ZFN) based system, a Transcription Activator-Like Effector-based Nuclease (TALEN) based system, a CRISPR-based system, or NgAgo-based system.

Meganuclease-based, ZFN-based and TALEN-based each comprise at least one DNA-binding domain or a nucleic acid comprising a nucleic acid sequence(s) encoding the DNA-binding domain, and achieve specific targeting or recognition of a target genomic region(s) via protein-DNA interactions. A CRISPR-based system comprises at least one guide RNA element or a nucleic acid comprising a nucleic acid sequence(s) encoding the guide RNA element, and achieves specific targeting or recognition of a target genomic region(s) via base-pairs directly with the DNA of the target genomic region(s). A NgAgo-based system comprises at least one guide DNA element or a nucleic acid comprising a nucleic acid sequence(s) encoding the guide DNA element, and achieves specific targeting or recognition of a target genomic region(s) via base-pairs directly with the DNA of the target genomic region(s).

In some embodiments, the genome editing system is a meganuclease-based system. A meganuclease-based system employs meganucleases which are endonucleases with large (>14 bp) recognition sites, and its DNA binding domains are also responsible for cleavage of target sequences. The DNA-binding domain of meganucleases may have a double-stranded DNA target sequence of 12 to 45 bp. In some embodiments, the meganuclease is either a dimeric enzyme, wherein each meganuclease domain is on a monomer, or a monomeric enzyme comprising the two domains on a single polypeptide. Not only wild-type meganucleases but also various meganuclease variants have been generated by protein engineering to cover a myriad of unique sequence combinations. In some embodiments, chimeric meganucleases with a recognition site composed of a half-site of meganuclease A and a half-site of protein B can also be used. Specific examples of such chimeric meganucleases comprising the protein domains of I-Dmol and I-CreI. Examples of meganucleases include homing endonucleases from the LAGLIDADG family.

The LAGLIDADG meganuclease can be I-SceI, I-ChuI, I-CreI, I-CsmI, PI-SceI, PI-TliI, PI-MtuI, I-CeuI, I-SceII, 1-SceIII, HO, PI-CivI, PI-Ctrl, PI-AaeI, PI-BsuI, PI-DhaI, PI-DraI, PI-MavI, PI-MchI, PI-MfuI, PI-MflI, PI-MgaI, PI-MgoI, PI-MinI, PI-MkaI, PI-MleI, PI-MmaI, PI-MshI, PI-MsmI, PI-MthI, PI-MtuI, PI-MxeI, PI-NpuI, Pl-PfuI, PI-RmaI, PI-SpbI, PI-SspI, PI-FacI, PI-MjaI PI-PhoI, PI-TagI, PI-ThyI, PI-TkoI, PI-TspI, or I-MsoI; or can be a functional mutant or variant thereof, whether homodimeric, heterodimeric or monomeric. In some embodiments, the LAGLIDADG meganuclease is a I-CreI derivative. In some embodiments, the LAGLIDADG meganuclease shares at least 80% similarity with the natural I-CreI LAGLIDADG meganuclease. In some embodiments, the LAGLIDADG meganuclease shares at least 80% similarity with residues 1-152 of the natural I-CreI LAGLIDADG meganuclease. In some embodiments, the LAGLIDADG meganuclease may consists of two monomers sharing at least 80% similarity with residues 1-152 of the natural I-CreI LAGLIDADG meganuclease linked together, with or without a linker peptide.

The "LAGLIDADG meganuclease" refers to a homing endonuclease from the LAGLIDADG family, as defined in Stoddard et al (Stoddard, 2005), or an engineered variant comprising a polypeptide sharing at least 80%, 85%, 90%, 95%, 97.5%, 99% or more identity or similarity with said natural homing endonuclease. Such engineered LAGLIDADG meganucleases can be derived from monomeric or dimeric meganucleases. When derived from dimeric meganucleases, such engineered LAGLIDADG meganucleases can be single-chain or dimeric endonucleases.

By "I-CreI" is intended the natural wild-type I-CreI meganuclease having the sequence of pdb accession code 1g9y.

The DNA recognition and cleavage functions of meganucleases are generally intertwined in a single domain. Unlike meganulceases, the DNA binding domains of ZFN-based and TALEN-based systems are distinct from the endonuclease for cleavage function. The ZFN-based system comprises: at least one zinc finger protein or a variant thereof, or a nucleic acid comprising a nucleotide sequence(s) encoding the zinc finer protein or variant thereof as its DNA-binding domain; and an endonuclease element, such as zinc finger nuclease (ZFN) or FokI cleavage domain. The zinc finder protein (ZFP) is non-naturally occurring in that it is engineered to bind to a target site of choice. See, for example, Beerli et al. (2002) Nature Biotechnol. 20: 135-141; Pabo et al. (2001) Ann. Rev. Biochem. 70:313-340; Isalan ei al. (2001) Nature Biotechnol. 19:656-660; Segal et al. (2001) Curr. Opin. Biotechnol. 12:632-637; Choo et al. (2000) Curr. Opin. Struct Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Various kinds of selection methods can be used with the methods herein. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227. In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Selection of target sites; ZFPs and methods for design and construction of fusion proteins (and polynucleotides encoding same) are known to those of skill in the art and described in detail in U.S. Pat. Nos. 6,140,0815; 789, 538; 6,453,242; 6,534,261; 5,925,523; 6,007,988; 6,013, 453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A Transcription Activator-Like Effector-based Nuclease (TALEN) system refers to a genome editing system that employs one or more Transcription Activator-Like Effector (TALE)-DNA binding domain and an endonuclease element, such as FokI cleavage domain. The TALE-DNA binding domain comprises one or more TALE repeat units, each having 30-38 (such as, 31, 32, 33, 34, 35, or 36) amino acids in length. The TALE-DNA binding domain may employ a full length TALE protein or fragment thereof, or a variant thereof. The TALE-DNA binding domain can be fused or linked to the endonuclease domain by a linker.

The terms "CRISPR-based system," "CRISPR-based gene editing system," "CRISPR-genome editing," "CRISPR-gene editing," "CRISPR-endonuclease based genome editing," and the like are used interchangeably herein, and collectively refer to a genome editing system that comprises one or more guide RNA elements; and one or more RNA-guided endonuclease elements. The guide RNA element comprises a targeter RNA comprising a nucleotide sequence substantially complementary to a nucleotide sequence at the one or more target genomic regions or a nucleic acid comprising a nucleotide sequence(s) encoding the targeter RNA. The RNA-guided endonuclease element comprises an endonuclease that is guided or brought to a target genomic region(s) by a guide RNA element; or a nucleic acid comprising a nucleotide sequence(s) encoding such endonuclease. Examples of such CRISPR-based gene editing system includes CRISPR-based system is a CRISPR-Cas system or a CRISPR-Cpf system.

As used herein, the terms "guide RNA element," "guide RNA", "gRNA," "gRNA molecule," and "synthetic guide RNA" are used interchangeably and refer to the polynucleotide sequence comprising a targeter RNA that hybridizes with a target nucleic sequence or a nucleic acid comprising a nucleotide sequence(s) encoding the targeter RNA. A targeter RNA of gRNA comprises a targeting domain that includes a nucleotide sequence substantially complementary to the nucleotide sequence at a target genomic region. The phrase "substantially complementary" means a degree of complementarity that is at least 60%, 65%, 70%, 75%, 80%, 85%, 90%. 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

A guide RNA element can further comprise an activator RNA that is capable of hybridizing with the targeter RNA, or a nucleic acid comprising a nucleotide sequence(s) encoding the activator RNA. The activator RNA and targeter RNA can be separate or fused as a single nucleic acid via a linker loop sequence to form a single gRNA molecule. A gRNA molecule may comprise a number of domains. For example, such gRNA comprises, for example from 5' to 3': a targeting domain (which is complementary to a target nucleic acid); a first complementarity domain; a linking domain; a second complementarity domain (which is complementary to the first complementarity domain); a proximal domain; and a optionally, a tail domain. See WO2015048557.

A "first complementarity domain" has substantial complementarity with the second complementarity domain, and may form a duplexed region under at least some physiological conditions.

A "linking domain" serves to link the first complementarity domain with the second complementarity domain of a unimolecular gRNA. The linking domain can link the first and the second complementarity domains covalently or non-covalently.

A "proximal domain" can be 3-25 nucleotides in length, or 5-20 nucleotides in length. The proximal domain can share homology with or be derived from a naturally occurring proximal domain.

A "tail domain" can be absent, or be 1, 2, 3, 4, 5, 6, 7, 8, 9, or 10 nucleotides in length. The tail domain may include sequences that are complementary to each other and which, under at least some physiological conditions, form a duplexed region.

The guide RNA element may form a complex with an endonuclease of the RNA-guided endonuclease element, such as Cas endonuclease ("gRNA/nuclease complex"). An example of gRNA/nuclease complex is a CRISPR complex as described below with respect to a CRISPR-based system. In some embodiments, the CRISPR complex comprises an endonuclease of RNA-guided endonuclease system that is complexed with the targeter RNA. In some embodiments, the CRISPR complex comprises an endonuclease of RNA-guided endonuclease system that is complexed with the targeter RNA and the activator RNA.

The targeting domain of targeter RNA promotes specific targeting or homing of a gRNA/nuclease complex to a target nucleotide sequence. In some embodiments, the targeting domain can be 10-30 bp, such as 15-25 bp, 18-22 bp, or 20 bp.

Methods for designing gRNAs are known in the art, including methods for selecting, designing, and validating target domain. See, for example, WO2015048577, Mali et al., 2013 SCIENCE 339(6121): 823-826; Hsu et al., 2013 NATBIOTECHNOL, 31(9): 827-32; Fu et al., 2014 NATB- TOTECHNOL, doi: 10.1038/nbt.2808. PubMed PMID: 24463574; Heigwer et al., 2014 NAT METHODS 11 (2): 122-3. doi: 1 0.1038/nmeth.2812. PubMed PMID: 24481216; Bae et al., 2014 BIOINFORMATICS PubMed PMID: 24463181; Xiao A et al., 2014 BIOINFORMATICS Pub Med PMID: 24389662.

In some embodiments, RNA-guided endonucleases, such as a Cas enzyme or protein (e.g., Type-II Cas9 protein) or Cpf enzyme or protein (e.g., Cpf1 protein) can be used. In some embodiments, a modified version of such Cas or Cpf enzyme or protein can also be used.

In some embodiments, the CRISPR-based system is a CRISPR-Cas system. The CRISPR-Cas system comprises: (a) at least one guide RNA element or a nucleic acid comprising a nucleotide sequence(s) encoding the guide RNA element, the guide RNA element comprising a targeter RNA that includes a nucleotide sequence substantially complementary to a nucleotide sequence at the one or more target genomic regions, and an activator RNA that includes a nucleotide sequence that is capable of hybridizing with the targeter RNA; and (b) a Cas protein element comprising a Cas protein or a nucleic acid comprising a nucleotide sequence encoding the Cas protein. The targeter RNA and activator RNAs can be separate or fused together into a single RNA.

In some embodiments, the CRISPR-based system includes Class 1 CRISPR and/or Class 2 CRISPR systems. Class 1 systems employ several Cas proteins together with a CRISPR RNAs (crRNA) as the targeter RNA to build a functional endonuclease. Class 2 CRISPR systems employ a single Cas protein and a crRNA as the targeter RNA. Class 2 CRISPR systems, including the type II Cas9-based system, comprise a single Cas protein to mediate cleavage rather than the multi-subunit complex employed by Class 1 systems. The CRISPR-based system also includes Class II, Type V CRISPR system employing a Cpf1 protein and a crRNA as the targeter RNA.

The Cas protein is a CRISPR-associated (Cas) double stranded nuclease. In some embodiments, CRISPR-Cas system comprises a Cas9 protein. In some embodiments, the Cas9 protein is SaCas9, SpCas9, SpCas9n, Cas9-HF, Cas9-H840A, FokI-dCas9, or D10A nickase. The term "Cas protein," such as Cas9 protein, include wild-type Cas protein or functional derivatives thereof (such as truncated versions or variants of the wild-type Cas protein with a nuclease activity).

In some embodiments, Cas9 proteins from species other than *S. pyogenes* and *S. thermophiles* can be used. Additional Cas9 protein species may be obtained and used herein include: Acidovorax avenae, Actinobacillus pleuropneumoniae, Actinobacillus succinogenes, Actinobacillus suis, Actinomyces sp., cycliphilus denitrificans, Aminomonas paucivorans, Bacillus cereus; Bacillus smithii, Bacillus thuringiensis, Bacteroides sp., Blastopirellula marina, Bradyrhizobium sp., Brevibacillus laterosporus, Campylobacter coli, Campylobacter jejuni, Campylobacter lari, Candidatus puniceispirillum, Clostridium cellulolyticum, Clostridium perfingens, Corynebacterium accolens, Corynebacterium dolichum, Corynebacterium matruchotii, Dinoroseobacter shibae, Eubacterium dolichum, gamma proteobacterium, Gluconacetobacter diazotrophicus, Haemoplzilus parainfluenzae, Haemophilus sputorum, Helicobacter canadensis, Helicohacter cinaedi, Helicobacter mustelae, Ilyobacter polytropus, Kingella kingae, Lactobacillus crispatus, Listeria ivanovii, Listeria monocytogenes, listeriaceae bacterium, *Methylocystis* sp., *Methylosinus trichosporium*, Mobiluncus mulieris, Neisseria bacilliformis, Neisseria cinerea, *Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutells, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In some embodiments, one or more elements of a CRISPR-based system is derived from a type I, type II, or type III CRISPR system In some embodiments, one or more elements of a CRISPR-based system is derived from a particular organism comprising an endogenous CRISPR system, such as *Streptococcus pyogenes, Staphylococcus aureus, Francisella tularensis, Prevotella* sp., *Acidaminococcus* sp., and *Lachnospiraceae* sp. In general, a CRISPR-based system is characterized by elements that promote the formation of a CRISPR complex at the target genomic regions or the site of a target sequence (also referred to as a protospacer in the context of an endogenous CRISPR system). In the context of formation of a CRISPR complex, "target sequence" refers to a sequence to which a guide sequence is designed to have substantial complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell(s). In some embodiments, the target sequence may be within an organelle of a eukaryotic cell(s), for example, mitochondrion or chloroplast.

A sequence or template that may be used for recombination into the targeted locus comprising the target sequences is referred to as an "editing template" or "editing polynucleotide" or "editing sequence". An exogenous template polynucleotide may be referred to as an editing template or donor template. In some embodiments, the recombination is homologous recombination.

In some embodiments, the CRISPR-based system is a CRISPR-Cas9 system. The targeter RNA of the CRISPR-Cas9 system comprises a CRISPR targeting RNA (crRNA) and the activator RNA of the CRISPR-Cas 9 system comprises a trans-activating CRISPR RNA (tracRNA). The Cas protein element of the CRISPR-Cas9 system employs a Cas9 protein. The crRNA and the tracrRNA can be separate or combined into a single RNA construct via a linker loop sequence. This combined RNA construct is called a single-guide RNA (sgRNA; or guide RNA).

With respect to general information on CRISPR-Cas systems, components thereof, and delivery of such components, including methods, materials, delivery vehicles, vectors, particles, AAV, and making and using thereof, including as to amounts and formulations can be found in: U.S. Pat. Nos. 8,999,641, 8,993,233, 8,945,839, 8,932,814, 8,906, 616, 8,895,308, 8,889,418, 8,889,356, 8,871,445, 8,865,406, 8,795,965, 8,771,945 and 8,697,359; US Patent Publications US 2014-0310830, US 2014-0287938 A1, US 2014-0273234 A1, US2014-0273232 A1, US 2014-0273231, US 2014-0256046 A1, US 2014-0248702 A1, US 2014-0242700 A1, US 2014-0242699 A1, US 2014-0242664 A1, US 2014-0234972 A1, US 2014-0227787 A1, US 2014-0189896 A1, US 2014-0186958, US 2014-0186919 A1, US 2014-0186843 A1, US 2014-0179770 A1 and US 2014-

0179006 A1, US 2014-0170753; European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/ 093661, WO 2014/093694, WO 2014/093595, WO 2014/ 093718, WO 2014/093709, WO 2014/093622, WO 2014/ 093635, WO 2014/093655, WO 2014/093712, WO2014/ 093701, WO2014/018423, WO 2014/204723, WO 2014/ 204724, WO 2014/204725, WO 2014/204726, WO 2014/ 204727, WO 2014/204728, WO 2014/204729, and WO2016/028682.

In some embodiments, the CRISPR-based system is a CRISPR-Cpf system. The "CRISPR-Cpf system" comprises: (a) at least one guide RNA element or a nucleic acid comprising a nucleotide sequence(s) encoding the guide RNA element, the guide RNA comprising a targeter RNA having a nucleotide sequence complementary to a nucleotide sequence at a locus of the target nucleic acid; and (b) a Cpf protein element or a nucleic acid comprising a nucleotide sequence encoding the Cpf protein element.

An example of a Cpf protein element includes a Cpf1 nucleases, such as *Francisella* Cpf1 (FnCpf1) and any variants thereof. See, for example, Zetsche et al., "Cpf1 is a single RNA-guided endonuclease of a class 2 CRISPR-Cas system," *Cell*, 163(3): pages 759-71; and Fonfara et al., "The CRISPR-associated DNA-cleaving enzyme Cpf1 also processes precursor CRISPR RNA," *Nature* 532 (7600): pages, 517-21. Cpf1's preferred PAM is 5'-TTN, differing from that of Cas9 (3'-NGG) in both genomic location and GC-content. The CRISPR-Cpf system may not employ an activator RNA (tracrRNA). Both Cpf1 and its guide RNAs are in general smaller than their SpCas9 counterparts. The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alfa-helical recognition lobe of Cas9. The Cpf1 loci encode Cas1, Cas2 and Cas4 proteins more similar to types I and III than from type II systems. Cpf1-family proteins can be found in many bacterial species.

Without being bound to a particular theory, the CRISPR-Cpf system employs a Cpf1-crRNA complex which cleaves target DNA or RNA by identification of a protospacer adjacent motif 5'-YTN-3 (where "Y" is a pyrimidine and "N" is any nucleobase) or 5'-TTN-3 in contrast to the G-rich PAM targeted by Cas9. After identification of PAM, Cpf1 introduces a sticky-end-like DNA double-stranded break of 4 or 5 nucleotides overhang.

In some embodiments, the genome editing system is a NgAgo-based system. The NgAgo-based system comprises at least one guide DNA element or a nucleic acid comprising a nucleic acid sequence(s) encoding the guide DNA element; and a DNA-guided endonuclease. The NgAgo-based system employs DNA as a guide element. Its working principle is similar to that of CRISPR-Cas9 technology, but its guide element is a segment of guide DNA(dDNA) rather than gRNA in CRISPR-Cas9 technology. An example of DNA-guided endonuclease is an Argonaute endonuclease (NgAgo) from *Natronobacterium gregoryi*. See, for example, Feng Gao et al. "DNA-guided genome editing using the *Natronobacterium gregoryi* Argonaute," *Nature Biotechnology*, (2016): doi:10.1038/nbt.3547.

By "linker," "peptide linker", "peptidic linker" or "peptide spacer" it is intended to mean a peptide sequence that allows the connection of different monomers in a fusion protein and the adoption of the correct conformation for said fusion protein activity and which does not alter the activity of either of the monomers. Peptide linkers can be of various sizes from 1, 2, 3, 4, 5, 10, 15, 20, 30, 40 to 50 amino acids as a non limiting indicative range or any intermediate value within this range.

DNAPK Inhibitors

In some embodiments, a compound represented by Structural Formula (I):

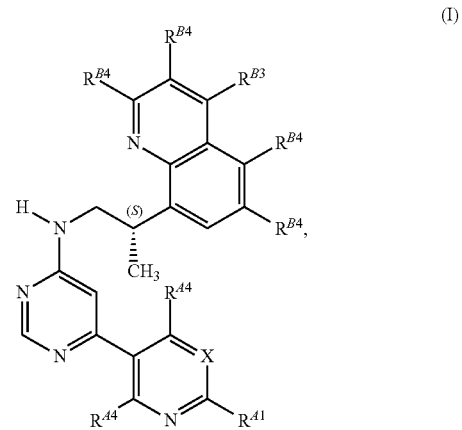

(I)

or a pharmaceutically acceptable salt or a co-crystal thereof is employed.

X is N or $CR^{A5}$.

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$cycloalkyl, or $C_{0-4}$alkyl-heterocyclyl. In embodiments, a heterocyclyl is selected from oxetanyl, tetrahydrofuranyl, tetrahydropyranyl, or morpholinyl. An alkyl, a cycloalkyl, or a heterocyclyl is unsubstituted or substituted (e.g., in embodiments, an alkyl, a cycloalkyl, or a heterocyclyl is optionally substituted with up to three F atoms, up to three $^2$H atoms, up to two non-geminal OH groups, or up to two $OC_{1-2}$alkyl).

Each $R^{A4}$ is, independently, H or $^2$H (D or deuterium). As used herein, the term "deuterium," "$^2$H" and "D" are interchangeably used.

$R^{A5}$ is hydrogen, F, $C_{1-4}$alkyl, or $OC_{1-4}$alkyl. An alkyl group is substituted or unsubstituted (e.g., in embodiments, an alkyl is optionally substituted with up to three F atoms or up to three $^2$H atoms).

$R^{B3}$ is $C(O)NHC_{1-4}$ alkyl. An alkyl is substituted or unsubstituted (e.g., an alkyl is optionally substituted with up to three F atoms, up to three $^2$H atoms, up to two non-geminal OH groups, or up to two $OC_{1-2}$alkyl).

Each $R^{B4}$ is, independently, hydrogen, deuterium, F, or $C_{1-4}$alkyl. An alkyl is substituted or unsubstituted.

In embodiments, X is N. In embodiments, X is $CR^{A5}$ (e.g., CH).

In embodiments, $R^{A1}$ is $C_{1-4}$alkyl. In embodiments, $R^{A1}$ is substituted $C_{1-4}$alkyl. In embodiments, $R^{A1}$ is unsubstituted $C_{1-4}$alkyl (e.g., methyl, ethyl, n-propyl, isopropyl, n-butyl, isobutyl, or sec-butyl).

In embodiments, one $R^{A4}$ is H, and the other $R^{A4}$ is $^2$H. In embodiments, both $R^{A4}$ are H. In embodiments, both $R^{A4}$ are $^2$H.

In embodiments, each $R^{B4}$ is, independently, hydrogen, deuterium, F, or $C_{1-4}$alkyl. In embodiments, each $R^{B4}$ is hydrogen.

In embodiments, $R^{B3}$ is $C(O)NHC_{1-4}$alkyl, wherein said alkyl is optionally substituted. In embodiments, an alkyl is optionally substituted with up to three F atoms, up to three $^2H$ atoms, up to two non-geminal OH groups, or up to two $OC_{1-2}$alkyl.

In embodiments, $R^{B3}$ is $C(O)NHC_{1-4}$alkyl, wherein said alkyl is unsubstituted (e.g., methyl, ethyl, n-propyl, isopropyl, n-butyl, isobutyl, or sec-butyl).

In embodiments, a pharmaceutically acceptable salt of a compound of Structural Formula (I) is employed.

In embodiments, the a co-crystal that includes a compound of Structural Formula (I) is employed.

In embodiments, a co-crystal that includes a compound of Structural Formula (I) and a co-crystal former (CCF) is employed. In embodiments, a CCF is adipic acid, citric acid, fumaric acid, maleic acid, succinic acid, or benzoic acid. In embodiments, a CCF is adipic acid.

In embodiments, the ratio of a co-crystal former (CCF) to a compound of Structural Formula (I) is about 2:1. In embodiments, the ratio of a co-crystal former (CCF) to a compound of Structural Formula (I) is about 1:2. In embodiments, a co-crystal includes a compound of Structural Formula (I) and a CCF in a ratio that is (a compound of Structural Formula (I))n:(CCF)m. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid.

In embodiments, a compound represented by Structural Formula (II),

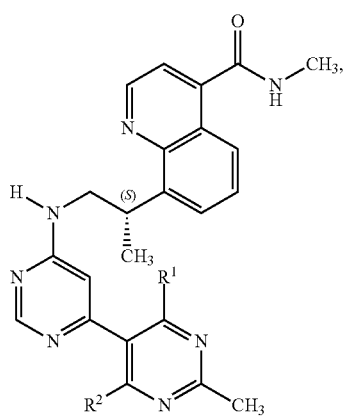

(II)

or a pharmaceutically acceptable salt thereof, or a co-crystal thereof is employed.

Each of $R^1$ and $R^2$ is independently hydrogen or deuterium.

In embodiments, each of $R^1$ and $R^2$ is hydrogen. In embodiments, each of $R^1$ and $R^2$ is deuterium.

In embodiments, a pharmaceutically acceptable salt of a compound of Structural Formula (II) is employed.

In embodiments, a co-crystal that includes a compound of Structural Formula (II) is employed.

In embodiments, a co-crystal that includes a compound of Structural Formula (II) and a co-crystal former (CCF) is employed. In embodiments, a CCF is adipic acid, citric acid, fumaric acid, maleic acid, succinic acid, or benzoic acid. In embodiments, a CCF is adipic acid.

In embodiments, the ratio of a co-crystal former (CCF) to a compound of Structural Formula (II) is about 2:1. In embodiments, the ratio of a co-crystal former (CCF) to a compound of Structural Formula (II) is about 1:2. In embodiments, a co-crystal includes a compound of Structural Formula (II) and a CCF in a ratio that is (a compound of Structural Formula (II))$_n$:(CCF)$_m$. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid.

In embodiments, a compound represented by Structural Formula (II"),

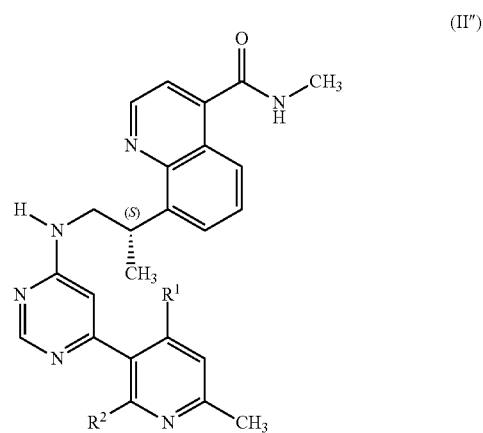

(II")

or a pharmaceutically acceptable salt thereof, or a co-crystal thereof is employed.

Each of $R^1$ and $R^2$ is independently hydrogen or deuterium.

In embodiments, each of $R^1$ and $R^2$ is hydrogen. In embodiments, each of $R^1$ and $R^2$ is deuterium.

In embodiments, a pharmaceutically acceptable salt of a compound of Structural Formula (II") is employed.

In embodiments, a co-crystal that includes a compound of Structural Formula (II") is employed.

In embodiments, a co-crystal that includes a compound of Structural Formula (II") and a co-crystal former (CCF) is employed.

In embodiments, a compound represented by the following structure,

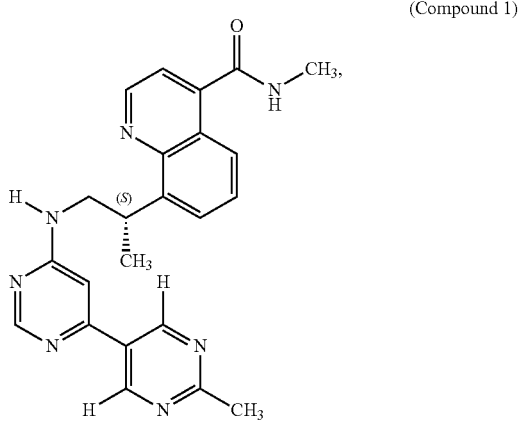

(Compound 1)

or a pharmaceutically acceptable salt thereof, or a co-crystal thereof is employed.

In embodiments, a pharmaceutically acceptable salt of Compound 1 is employed.

In embodiments, a co-crystal that includes Compound 1 is employed.

In embodiments, a co-crystal that includes Compound 1 and a co-crystal former (CCF) is employed. In embodiments, a CCF is adipic acid, citric acid, fumaric acid, maleic acid, succinic acid, or benzoic acid. In embodiments, a CCF is adipic acid.

In embodiments, the ratio of a co-crystal former (CCF) to Compound 1 is about 2:1. In embodiments, the ratio of a co-crystal former (CCF) to Compound 1 is about 1:2. In embodiments, a co-crystal includes Compound 1 and a CCF in a ratio that is (Compound 1)$_n$:(CCF)$_m$. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid.

In embodiments, a compound represented by the following structure,

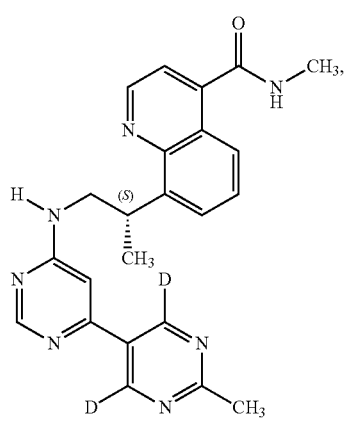

(Compound 2)

or a pharmaceutically acceptable salt thereof, or a co-crystal thereof is employed.

In embodiments, a pharmaceutically acceptable salt of Compound 2 is employed.

In embodiments, a co-crystal that includes Compound 2 is employed.

In embodiments, a co-crystal that includes Compound 2 and a co-crystal former (CCF) is employed. In embodiments, a CCF is adipic acid, citric acid, fumaric acid, maleic acid, succinic acid, or benzoic acid. In embodiments, a CCF is adipic acid.

In embodiments, the ratio of a co-crystal former (CCF) to Compound 2 is about 2:1. In embodiments, the ratio of a co-crystal former (CCF) to Compound 2 is about 1:2. In embodiments, a co-crystal includes Compound 2 and a CCF in a ratio that is (Compound 2)$_n$:(CCF)$_m$. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid.

In some embodiments, a compound represented by the following structure:

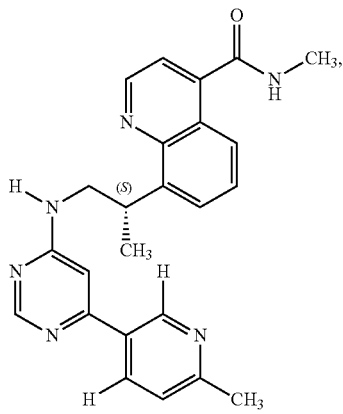

(Compound 3)

or a pharmaceutically acceptable salt thereof, or a co-crystal thereof is employed.

In embodiments, a pharmaceutically acceptable salt of Compound 3 is employed.

In embodiments, a co-crystal that includes Compound 3 is employed.

In embodiments, a co-crystal that includes Compound 3 and a co-crystal former (CCF) is employed.

In embodiments, a composition or a co-crystal that includes a compound as described herein provides the compound in the form of a single enantiomer that is at least about 95%, at least about 97%, or at least about 99% free of the corresponding enantiomer.

In embodiments, a composition or co-crystal that includes a compound as described herein provides the compound in the form of the (+) enantiomer, wherein the composition or co-crystal is at least about 95% free of the corresponding (−) enantiomer.

In embodiments, a composition or co-crystal that includes a compound as described herein provides the compound in the form of the (+) enantiomer, wherein the composition or co-crystal is at least about 97% free of the corresponding (−) enantiomer.

In embodiments, a composition or co-crystal that includes a compound as described herein provides the compound in the form of the (+) enantiomer, wherein the composition or co-crystal is at least about 99% free of the corresponding (−) enantiomer.

In embodiments, a composition or co-crystal that includes a compound as described herein provides the compound in the form of the (−) enantiomer, wherein the composition or co-crystal is at least about 95% free of the corresponding (+) enantiomer.

In embodiments, a composition or co-crystal that includes a compound as described herein provides the compound in the form of the (−) enantiomer, wherein the composition or co-crystal is at least about 97% free of the corresponding (+) enantiomer.

In embodiments, a composition or co-crystal that includes a compound as described herein provides the compound in the form of the (−) enantiomer, wherein the composition or co-crystal is at least about 99% free of the corresponding (+) enantiomer.

In embodiments, a compound represented by Structural Formula (I′),

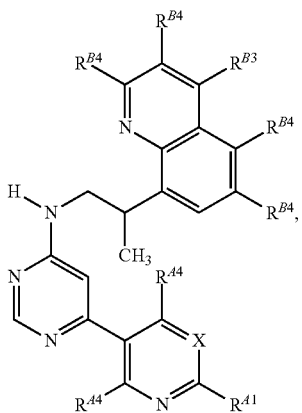

(I')

or a pharmaceutically acceptable salt or a co-crystal thereof is employed. In embodiments, each $R^{41}$, $R^{44}$, $R^{B4}$, $R^{B3}$, X, and $R^{45}$ is independently as described for Structural Formula (I) in any embodiment described herein.

Further, in any embodiments described herein, a compound or pharmaceutically acceptable salt of Structural Formula (I) may be replaced with a compound or pharmaceutically acceptable salt of Structural Formula (I').

In embodiments, a pharmaceutically acceptable salt of a compound of Structural Formula (I') is employed.

In embodiments, a co-crystal that includes a compound of Structural Formula (I') is employed. In embodiments, a co-crystal includes a co-crystal former (CCF). In embodiments, a CCF is adipic acid, citric acid, fumaric acid, maleic acid, succinic acid, or benzoic acid. In embodiments, a CCF is adipic acid.

In embodiments, the ratio of a compound of a co-crystal former (CCF) to a compound of Structural Formula (I') is about 2:1. In embodiments, the ratio of a compound of a co-crystal former (CCF) to a compound of Structural Formula (I') is about 1:2. In embodiments, a co-crystal includes a compound of Structural Formula (I') and a CCF in a ratio that is (a compound of Structural Formula (I'))$_n$:(CCF)$_m$. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid, citric acid, fumaric acid, maleic acid, succinic acid, or benzoic acid. In embodiments, a CCF is adipic acid.

In embodiments, a compound of Structural Formula (I') represented by Structural Formula (II'),

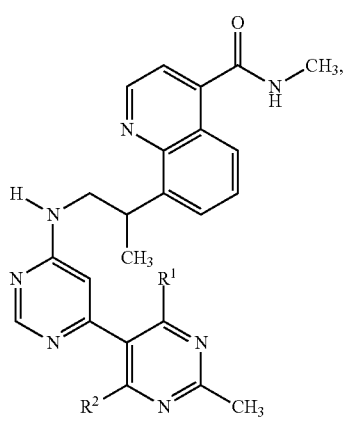

(II')

or a pharmaceutically acceptable salt thereof, or a co-crystal thereof is employed.

In embodiments, each $R^1$ and $R^2$ is independently hydrogen or deuterium.

In embodiments, both $R^1$ and $R^2$ are hydrogen. In embodiments, both $R^1$ and $R^2$ are deuterium.

In embodiments, a compound or pharmaceutically acceptable salt of Structural Formula (II') is employed.

In embodiments, a pharmaceutically acceptable salt of a compound of Structural Formula (II') is employed.

In embodiments, a co-crystal that includes a compound of Structural Formula (II') is employed. In embodiments, a co-crystal includes a co-crystal former (CCF). In embodiments, a CCF is adipic acid, citric acid, fumaric acid, maleic acid, succinic acid, or benzoic acid. In embodiments, a CCF is adipic acid.

In embodiments, the ratio of a compound of a co-crystal former (CCF) to a compound of Structural Formula (II') is about 2:1. In embodiments, the ratio of a compound of a co-crystal former (CCF) to a compound of Structural Formula (II') is about 1:2. In embodiments, a co-crystal includes a compound of Structural Formula (II') and a CCF in a ratio that is (a compound of Structural Formula (II'))$_n$:(CCF)$_m$. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid, citric acid, fumaric acid, maleic acid, succinic acid, or benzoic acid. In embodiments, a CCF is adipic acid.

In embodiments, a compound of Structural Formula (I') represented by Structural Formula (II'''),

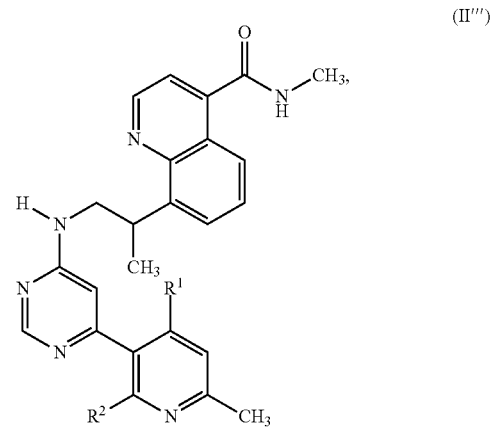

(II''')

or pharmaceutically acceptable salt thereof, or a co-crystal thereof is employed.

In embodiments, each $R^1$ and $R^2$ is independently hydrogen or deuterium.

In embodiments, both $R^1$ and $R^2$ are hydrogen. In embodiments, both $R^1$ and $R^2$ are deuterium.

In embodiments, a compound or pharmaceutically acceptable salt of Structural Formula (II''') is employed.

In embodiments, a pharmaceutically acceptable salt of a compound of Structural Formula (II''') is employed.

In embodiments, a co-crystal that includes a compound of Structural Formula (II''') is employed. In embodiments, a co-crystal includes a co-crystal former (CCF). In embodiments, a CCF is adipic acid, citric acid, fumaric acid, maleic acid, succinic acid, or benzoic acid. In embodiments, a CCF is adipic acid.

In embodiments, a compound represented by a formula selected from the group consisting of:

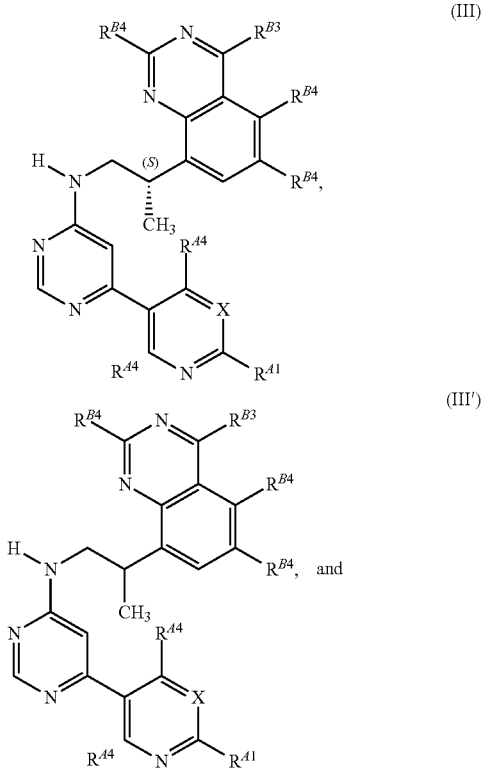

or a pharmaceutically acceptable salt or a co-crystal thereof is employed.

In embodiments, each $R^{A1}$, $R^{A4}$, $R^{B4}$, $R^{B3}$, X, and $R^{A5}$ is independently as described for Structural Formula (I) in any embodiment described herein.

In embodiments, a compound or pharmaceutically acceptable salt of Structural Formula (I) may be replaced with a compound or pharmaceutically acceptable salt of Structural Formula (III) or (III').

In embodiments, a pharmaceutically acceptable salt of a compound of Structural Formula (III) or (III') is employed.

In embodiments, a co-crystal that includes a compound of Structural Formula (III) or (III) is employed. In embodiments, a co-crystal includes a co-crystal former (CCF). In embodiments, a CCF is adipic acid, citric acid, fumaric acid, maleic acid, succinic acid, or benzoic acid. In embodiments, a CCF is adipic acid.

In embodiments, the ratio of a compound of a co-crystal former (CCF) to a compound of Structural Formula (III) or (HI) is about 2:1. In embodiments, the ratio of a compound of a co-crystal former (CCF) to a compound of Structural Formula (III) or (HI) is about 1:2.

In embodiments, a co-crystal includes a compound of Structural Formula (III) and a CCF in a ratio that is (a compound of Structural Formula (III))$_n$:(CCF)$_m$. In embodiments, a co-crystal includes a compound of Structural Formula (III') and a CCF in a ratio that is (a compound of Structural Formula (III'))$_n$:(CCF)$_m$. In embodiments, n is about 1 and m is about 0.4 to about 2.1. In embodiments, n is about 1 and m is about 0.9 to about 3.1. In embodiments, n is about 2 and m is about 1. In embodiments, n is about 1 and m is about 2. In embodiments, a CCF is adipic acid, citric acid, fumaric acid, maleic acid, succinic acid, or benzoic acid. In embodiments, a CCF is adipic acid.

As described herein, compounds disclosed herein may optionally be substituted with one or more substituents, such as are illustrated generally above, or as exemplified by particular classes, subclasses, and species. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

Where chemically feasible or chemically stable, a molecular group described herein is unsubstituted or substituted (i.e., "optionally substituted"). As described herein, when the term "optionally substituted" precedes a list, said term refers to all of the subsequent substitutable groups in that list. For example, if group X is "halogen; optionally substituted alkyl or phenyl;" then X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-4}$ alkyl, or phenyl, wherein X is optionally substituted by $J^x$, then both $C_{1-4}$alkyl and phenyl may be optionally substituted by $J^x$. As is apparent to one having ordinary skill in the art, groups such as H, halogen, $NO_2$, CN, $NH_2$, OH, or $OCF_3$ would not be included because they are not substitutable groups. As is also apparent to a skilled person, a heteroaryl or heterocyclic ring containing an NH group can be optionally substituted by replacing the hydrogen atom with the substituent.

In embodiments, a group (e.g., a $C_{1-4}$alkyl; $C_{3-5}$cycloalkyl; a heterocyclyl such as oxetanyl, tetrahydrofuranyl, tetrahydropyranyl, or morpholinyl; an aryl such as a phenyl; or a heteroaryl) is unsubstituted.

In embodiments, a group (e.g., a $C_{1-4}$alkyl; $C_{3-5}$cycloalkyl; a heterocyclyl such as oxetanyl, tetrahydrofuranyl, tetrahydropyranyl, or morpholinyl; an aryl such as a phenyl; or a heteroaryl) is substituted. In embodiments, a group comprises 1, 2, 3, 4, 5, or 6 substituents as valency and chemical stability permits.

Combinations of substituents envisioned in this disclosure are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In embodiments, a stable compound or chemically feasible compound is one that is not substantially altered when kept at a temperature of 40° C. or less, in the absence of moisture or other chemically reactive conditions, for at least a week.

The term "about" in relation to a numerical value x means, for example, x+/−10%.

The term "alkyl" or "alkyl group," as used herein, means a straight-chain (i.e., unbranched) or branched, substituted or unsubstituted hydrocarbon chain that is completely saturated. Unless otherwise specified, alkyl groups have 1-8 carbon atoms (represented as "$C_{1-8}$ alkyl"). In embodiments, alkyl groups have 1-6 carbon atoms (represented as "$C_{1-6}$ alkyl"). In embodiments, alkyl groups have 1-4 carbon atoms (represented as "$C_{1-4}$ alkyl"). In embodiments, a molecular entity described as a "C$_{0-4}$alkyl" includes a covalent bond (e.g., a "Co alkyl") or a C$_{1-4}$alkyl chain as described herein. Examples of alkyl groups include methyl, ethyl, propyl, butyl, isopropyl, isobutyl, sec-butyl, and tert-butyl.

The term "alkylene," as used herein, represents a saturated divalent straight or branched chain hydrocarbon group and is exemplified by methylene, ethylene, isopropylene and the like.

The term "alkylidene," as used herein, represents a divalent straight chain alkyl linking group.

The term "alkenyl," as used herein, represents monovalent straight or branched chain hydrocarbon group containing one or more carbon-carbon double bonds.

The term "alkynyl," as used herein, represents a monovalent straight or branched chain hydrocarbon group containing one or more carbon-carbon triple bonds.

The term "cycloalkyl" (or "carbocycle"), as used herein, refers to a monocyclic C$_3$-C$_8$ hydrocarbon or bicyclic C$_8$-C$_{12}$ hydrocarbon that is completely saturated and has a single point of attachment to the rest of the molecule, and wherein any individual ring in said bicyclic ring system has 3-7 members. Exemplary cycloalkyl groups include, but are not limited to, cyclopropyl, cyclobutyl, cyclopentyl, cyclohexyl, and cycloheptyl.

The term "heterocycle," "heterocyclyl," "heterocycloalkyl," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloalkyl," or "heterocyclic" group has three to fourteen ring members in which one or more ring members is a heteroatom independently selected from oxygen, sulfur, nitrogen, or phosphorus, and each ring in the system contains 3 to 8 ring members. Examples of heterocyclic rings include, but are not limited to, the following monocycles: 2-tetrahydrofuranyl, 3-tetrahydrofuranyl, 2-tetrahydrothiophenyl, 3 tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4 thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

The term "heteroatom," as used herein, means one or more of oxygen, sulfur, nitrogen, or phosphorus, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy," as used herein, mean alkyl, alkenyl, or alkoxy, as the case may be, substituted with one or more halogen atoms. The term "halogen" means F, Cl, Br, or I.

The term "aryl," as used herein, used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. The term "aryl" may be used interchangeably with the term "aryl ring." Examples of aryl rings include phenyl, naphthyl, and anthracene.

As used herein, the term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 4 to 7 ring members. The term "heteroaryl" may be used interchangeably with the term "heteroaryl ring" or the term "heteroaromatic." Further examples of heteroaryl rings include the following monocycles: 2 furanyl, 3-furanyl, N-imidazolyl, 2-imidazolyl, 4-imidazolyl, 5-imidazolyl, 3-isoxazolyl, 4 isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3 pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1, 2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

Unless otherwise depicted or stated, structures recited herein can include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of this disclosure. Compounds that have been drawn with stereochemical centers defined, usually through the use of a hatched or bolded bond, are stereochemically pure, but with the absolute stereochemistry still undefined. Such compounds can have either the R or S configuration. In those cases where the absolute configuration has been determined, the chiral center(s) are labeled (R) or (S) in the drawing.

Unless otherwise stated, all tautomeric forms of the compounds disclosed herein are within the scope of such disclosure. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this disclosure. Such compounds are useful, for example, as analytical tools, probes in biological assays, or as DNAPK inhibitors with an improved therapeutic profile.

Pharmaceutically Acceptable Salts

It will also be appreciated that certain of the compounds disclosed herein can exist in free form or where appropriate, as a pharmaceutically acceptable derivative thereof. A pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in J. Pharmaceutical Sciences, 66: 1-19, 1977, which is incorporated herein by reference with respect to the pharmaceutically acceptable salts. Pharmaceutically acceptable salts of the compounds disclosed herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include alginate, ascorbate, aspartate, benzenesulfonate, bisulfate, borate, butyrate, camphorate, camphorsulfonate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, sulfate, tartrate, thiocyanate, p-toluenesulfonate, undecanoate, valerate salts, and the like. Still further exemplary salts include adipate, benzoate, citrate, fumarate, maleate, or succinate. Salts derived from appropriate bases include alkali metal, alkaline earth metal, ammonium and N+($C_{1-4}$alkyl)$_4$ salts.

Included in this disclosure also is the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

Co-Crystals

In embodiments, a co-crystal that includes a compound as described herein (e.g., a compound represented by Structural Formula (I), (II), or (II")) and a co-crystal former (CCF) is employed.

In embodiments, a compound represented by Structural Formula (I), (II), or (II") and a CCF are both in the solid state (e.g., crystalline). In embodiments, a compound represented by Structural Formula (I), (II), or (II") and a CCF are bonded non-covalently (e.g., by hydrogen bonding).

In embodiments, a co-crystal of a compound represented by Structural Formula (I) or (II) and a CCF (e.g., adipic acid, citric acid, fumaric acid, maleic acid, succinic acid, or benzoic acid) is a solid at room temperature. In embodiments, a co-crystal of a compound represented by Structural Formula (I) or (II) and a CCF (e.g., adipic acid, citric acid, fumaric acid, maleic acid, succinic acid, or benzoic acid) interact by noncovalent bonds. In embodiments, a noncovalent bond interaction between a compound represented by Structural Formula (I) or (II) and a CCF (e.g., adipic acid, citric acid, fumaric acid, maleic acid, succinic acid, or benzoic acid) includes hydrogen bonding and/or van der Waals interactions.

In embodiments, a co-crystal former (CCF) is adipic acid, citric acid, fumaric acid, maleic acid, succinic acid, or benzoic acid.

In embodiments, a co-crystal is a co-crystal that is described in International Publication No. WO 2015/058067, which is hereby incorporated by reference in its entirety.

In embodiments, a co-crystal includes (5)-N-methyl-8-(1-((2'-methyl-[4,5'-bipyrimidin]-6-yl)amino)propan-2-yl)quinoline-4-carboxamide. In embodiments, the compound is the (+) enantiomer. In embodiments, the compound is the (−) enantiomer.

In embodiments, a co-crystal includes (5)-N-methyl-8-(1-((2'-methyl-4 6'-dideutero-[4,5'-bipyrimidin]-6-yl)amino)propan-2-yl)quinoline-4-carboxamide. In embodiments, the compound is the (+) enantiomer. In embodiments, the compound is the (−) enantiomer.

In embodiments, a co-crystal that includes a compound represented by Structural Formula (I) or (II) (e.g., Compound 1 or Compound 2) and citric acid as a CCF is employed.

In embodiments, the invention features a co-crystal that includes a compound represented by Structural Formula (I) or (II) (e.g., Compound 1 or Compound 2) and fumaric acid as a CCF.

In embodiments, a co-crystal that includes a compound represented by Structural Formula (I) or (II) (e.g., Compound 1 or Compound 2) and maleic acid as a CCF is employed.

In embodiments, a co-crystal that includes a compound represented by Structural Formula (I) or (II) (e.g., Compound 1 or Compound 2) and succinic acid as a CCF is employed.

In embodiments, a co-crystal that includes a compound represented by Structural Formula (I) or (II) (e.g., Compound 1 or Compound 2) and benzoic acid as a CCF is employed.

In embodiments, a co-crystal that includes a compound represented by Structural Formula (I) or (II) (e.g., Compound 1 or Compound 2) and adipic acid as a CCF is employed.

In embodiments, a co-crystal that includes Compound 1 and adipic acid is employed. In embodiments, the molar ratio of Compound 1 to adipic acid is about 2:1. In embodiments, the molar ratio of Compound 1 to adipic acid is about 1:2.

In embodiments, a co-crystal that includes Compound 2 and adipic acid is employed. In embodiments, the molar ratio of Compound 2 to adipic acid is about 2:1. In embodiments, the molar ratio of Compound 2 to adipic acid is about 1:2.

In embodiments, a co-crystal that includes Compound 1 and adipic acid is in polymorphic Form A as described in International Publication No. WO 2015/058067. In embodiments, a co-crystal that includes Compound 1 and adipic acid is in polymorphic Form B as described in International Publication No. WO 2015/058067. In embodiments, a co-crystal that includes Compound 1 and adipic acid is a mixture of polymorphic Forms A and B as described in International Publication No. WO 2015/058067.

In embodiments, a co-crystal that includes Compound 2 and adipic acid is in polymorphic Form A as described in International Publication No. WO 2015/058067. In embodiments, a co-crystal that includes Compound 2 and adipic acid is in polymorphic Form B as described in International Publication No. WO 2015/058067. In embodiments, a co-crystal that includes Compound 2 and adipic acid is a mixture of polymorphic Forms A and B as described in International Publication No. WO 2015/058067.

In some embodiments, a co-crystal is employed wherein such co-crystal includes a compound represented by Structural Formula (I) or (II) (e.g., Compound 1 or Compound 2) and a CCF described above in isolated, pure form, or in a mixture as a solid composition when admixed with other materials, for example, free form of a compound represented by Structural Formula (I) (e.g., Compound 1 or Compound 2) or free CCF.

In some embodiments, pharmaceutically acceptable compositions comprising a co-crystal of a compound represented by Structural Formula (I) (e.g., Compound 1 or Compound 2), a first CCF (e.g., as described herein), and one or more additional free CCF, which may be the same as or different from the first CCF, is employed. In some embodiments, a composition includes a co-crystal of a compound represented by Structural Formula (I) (e.g., Compound 1 or Compound 2), a first CCF that is adipic acid, and additional adipic acid. In some embodiments, the overall molar ratio of a compound represented by Structural Formula (I) (e.g., Compound 1 or Compound 2) to CCF (e.g., total CCF that includes both a first CCF (e.g., as described herein and one or more additional free CCF) in such compositions ranges from about 1:0.55 to about 1:100. In some embodiments, the overall molar ratio of a compound represented by Structural Formula (I) (e.g., Compound 1 or Compound 2) to CCF in such compositions ranges from about 1:0.55 to about 1:50. In some embodiments, the overall molar ratio of the compound of a compound represented by Structural Formula (I) (e.g., Compound 1 or Compound 2) to CCF in such compositions is in a range from about 1:0.55 to about 1:10. In some embodiments, the overall weight ratio of the compound of formula I to CCF in such compositions ranges from about 85 wt %:15 wt % to about 60 wt %:40 wt %. In some embodiments, the overall weight ratio of the compound of a compound represented by Structural Formula (I) (e.g., Compound 1 or Compound 2) to CCF ranges from about 70 wt %:30 wt % to about 60 wt %: 40 wt %. In some embodiments, the overall weight ratio of a compound represented by Structural Formula (I) (e.g., Compound 1 or Compound 2) to CCF is about 65 wt %:35 wt %.

DNAPK Inhibitors for Increasing Genomic Editing Efficiency

Targeted genome editing efficiency can be increased by administering to a cell(s) with one or more compounds (e.g., DNAPK inhibitors) described herein and a genome editing system. Genome editing systems suitable for use include, for example, a meganuclease based system, a zinc finger nuclease (ZFN) based system, a Transcription Activator-Like Effector-based Nuclease (TALEN) system, a CRISPR-based system or NgAgo-based system. The methods, compositions, and kits of the disclosure provide DNAPK inhibitors and/or a genome editing system for increasing genome editing efficiency. In some embodiments, HDR genome editing efficiency is increased following administering to a cell(s) with a DNAPK inhibitor.

In some embodiments, the genome editing system is a CRISPR-based genome editing system. The CRISPR-based genome editing system can be a CRISPR-Cas system or variants thereof. The CRISPR-Cas system can use any Cas endonucleases, such as Cas 9 endonucleases and variants thereof. Examples of Cas 9 endonucleases includes Cas9 endonucleases or variants thereof, such as SaCas9, SpCas9, SpCas9n, Cas9-HF, Cas9-H840A, FokI-dCas9, or CasDIOA nickase. The Cas endonuclease can be wild type, engineered, or a nickase mutant, or any variations thereof.

In some embodiments, the CRISPR-based genome editing system includes a CRISPR sequence, a trans-activating cr (tracr) sequence, a guide sequence and a Cas endonuclease or any combinations thereof.

In some embodiments, the CRISPR-based genome editing system includes a RNA comprising a CRISPR sequence (crRNA), a RNA comprising a trans-activating cr (tracr) sequence (tracrRNA) and a Cas endonuclease or any combinations thereof.

In some embodiments, the CRISPR-based genome editing system includes a CRISPR sequence, a guide sequence, and a Cas endonuclease or a Cpf endonuclease, or any combinations thereof.

In some embodiments, the CRISPR-based genome editing system is a CRISPR-Cpf system. The Cpf nuclease is a Class 2 CRISPR-Cas system endonuclease. Cpf is a single RNA-guided endonuclease. The Cpf nuclease can be wild type, engineered or a nickase mutant, or any variations thereof. See, for example, Zetsche et al., "CPF1 is a single RNA-guided endonuclease of a Class 2 CRISPR-Cas System," *Cell*, 163(3): 759-71. In some embodiments, the Cpf nuclease is a Cpf 1 endonuclease.

In some embodiments, the genome editing system is a meganuclease based system. Meganuclease-based genome editing uses sequence-specific endonucleases that recognize large DNA target sites (e.g. typically about >12 bp). See, for example, U.S. Pat. No. 9,365,964. Meganucleases can cleave unique chromosomal sequences without affecting overall genome integrity. In some embodiments, the meganuclease can be a homing endonuclease. In some embodiments, the meganuclease can be an intron endonuclease or an intein endonuclease. The homing endonucleases can belong to the LAGLIDADG family. The meganucleases can be wild type, engineered or a nickase mutant.

In some embodiments, the gene-editing system is a zinc finger nuclease (ZFN) based system. The ZFN is an artificial restriction enzyme engineered based on the fusion between a zing finger DNA-binding domain and a DNA-cleavage domain. See, for example, U.S. Pat. No. 9,145,565.

In some embodiments, the gene-editing system is a Transcription Activator-Like Effector-based Nuclease (TALEN). TALENs are engineered restriction enzymes that are made by the fusion of a TAL effector DNA-binding domain to a DNA cleavage domain. See, for example, U.S. Pat. No. 9,181,535.

In some embodiments, the gene editing system is an Argonaute based system.

Argonaute based gene editing systems include an Argonaute derived endonuclease and a 5' phosphorylated ssDNA. In some embodiments, the phosphorylated ssDNA can be 10-40 nucleotides, 15-30 nucleotide or 18-30 nucleotides (e.g, about 24 nucleotides) in length. In some embodiments, the Argonaute endonuclease can be any endonuclease. In some embodiments, the Argonaute endonuclease is derived from *Thermus thermophiles* (TtAgo), *Pyrococcus furiosus* (PfAgo), or *Natronobacterium gregoryi* (NgAgo). In some embodiments, the *Natrobacterium gregoryi* (NgAgo) is strain 2 (i.e. *N. gregoryi* SP2). In some embodiments the Argonaute endonuclease is NgAgo. See, for example, Gao et al., "DNA-guided genome editing using the *Natronobacterium gregoryi* Argonaute," *Nature Biotechnology*, May 2016.

The DNAPK inhibitors can be any DNAPK inhibitor. The DNAPK inhibitor can be any compound or substance that causes inhibition of a DNAPK. The DNAPK inhibitor can be a compound, small molecule, antibody, or nucleotide sequence. In some embodiments, the DNAPK inhibitors are compounds represented by Structural Formula I or Structural Formula II. In some embodiments, the DNAPK inhibitors are compounds represented by Structural Formula I' or Structural Formula II'. In some embodiments, the DNAPK inhibitor is Compound 1, Compound 2 or Compound 3. In some embodiments, the DNAPK inhibitor is a co-crystal that includes Compound 1, Compound 2 or Compound 3, and adipic acid. In some embodiments, the ratio of adipic acid to either Compound 1, Compound 2 or Compound 3 is about 5 to 0.5, or any ratios in between. In some embodiments, the ratio of adipic acid to either Compound 1, Compound 2 or Compound 3 is about 4 to 0.5, or any ratios in between. In some embodiments, the ratio of adipic acid to either Compound 1, Compound 2 or Compound 3 is about 3 to 0.5, or any ratios in between. In some embodiments, the ratio of adipic acid to either Compound 1, Compound 2 or Compound 3 is about 2 to 0.5, or any ratios in between. In some embodiments, the ratio of adipic acid to either Compound 1, Compound 2 or Compound 3 is about 2 to 1.0, or any ratios in between.

In some embodiments, the DNAPK inhibitor is Compound 1, Compound 2 or Compound 3, or a combination thereof.

In some embodiments, any NHEJ inhibitor can be used to increase HDR genome editing efficiency. In some embodiments, the NHEJ inhibitor is Compound 1, Compound 2 or Compound 3, or a combination thereof.

In some embodiments, the NHEJ inhibitor can be any compound or substance that causes inhibition of a NHEJ. Examples of NHEJ inhibitor include DNAPK inhibitors. The NHEJ inhibitor can be a compound, small molecule, antibody, or nucleotide sequence. In some embodiments, the NHEJ inhibitors are compounds represented by Structural Formula I, I', II, II', II", II"', III or III'. In some embodiments, the NHEJ inhibitor is Compound 1, Compound 2 or Compound 3, or a combination thereof. In some embodiments, the NHEJ inhibitor is a co-crystal that includes Compound 1, Compound 2, or Compound 3, and adipic acid. In some embodiments, the ratio of adipic acid to any of Compound 1, Compound 2 or Compound 3 is about 5 to 0.5, or any ratios in between. In some embodiments, the ratio of adipic acid to any of Compound 1, Compound 2 or Compound 3 is about 4 to 0.5, or any ratios in between. In some embodiments, the ratio of adipic acid to any of Compound 1, Compound 2 or Compound 3 is about 3 to 0.5, or any ratios in between. In some embodiments, the ratio of adipic acid to any of Compound 1, Compound 2 or Compound 3 is about 2 to 0.5, or any ratios in between. In some embodiments, the ratio of adipic acid to any of Compound 1, Compound 2 or Compound 3 is about 2 to 1.0, or any ratios in between.

In some embodiments, the increased genome editing efficiency is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNAPK inhibitor and a genome editing system is not administered to a cell(s), or compared to a condition in which only a genome editing system and not a DNAPK inhibitor is administered to a cell(s).

Use of DNAPK Inhibitors and Genome Editing System, Kits, and Compositions Thereof Genome editing, in which particular genomic regions are precisely altered, holds great therapeutic potential.

In some embodiments, provided herein are methods for editing one or more target genomic regions, for repairing a DNA break in one or more target genomic regions via a HDR pathway, for inhibiting or suppressing NHEJ-mediated repair of a DNA break in one or more target genomic, and for modifying the expression of one or more genes or proteins via administering to a cell(s) a genome editing system and a DNAPK inhibitor.

In some embodiments, provided herein are methods of modifying expression of one or more genes or proteins comprising administering to one or more cells that comprise one or more target genomic regions, a genome editing system and a DNAPK inhibitor described herein, wherein the genome editing system interacts with a nucleic acid(s) of the one or more target genomic regions of a target gene(s), resulting in editing the one or more target genomic regions and wherein the edit modifies expression of a downstream gene(s) and/or protein(s) associated with the target gene(s).

The genome editing system can be any genome editing system that can edit a target genomic region in a cell(s). Exemplary genome editing systems are described in detail above and can include, for example, a meganuclease based system, a zinc finger nuclease (ZFN) based system, a Transcription Activator-Like Effector-based Nuclease (TALEN) system, a CRISPR-based system, or NgAgo-based system Editing of the one or more target genomic regions includes any kind of genetic manipulations or engineering of a cell's genome. The editing of the one or more target genomic regions can include insertions, deletions, or replacements of genomic regions in a cell(s) performed by one or more endonucleases. Genomic regions comprise the genetic material in a cell(s), such as DNA, RNA, polynucleotides, and oligonucleotides. Genomic regions in a cell(s) also comprise the genomes of the mitochondria or chloroplasts contained in a cell(s).

The DNAPK inhibitor can be any DNAPK inhibitor. The DNAPK inhibitor can be any compound or substance that causes inhibition of a DNAPK. The DNAPK inhibitor can be a compound, small molecule, antibody, or nucleotide sequence. In some embodiments, the DNAPK inhibitors are compounds represented by Structural Formula I, Structural Formula II, or Structural Formula II". In some embodiments, the DNAPK inhibitors are compounds represented by Structural Formula I', Structural Formula II', or Structural Formula IF". In some embodiments, the DNAPK inhibitor is Compound 1, Compound 2 or Compound 3. In some embodiments, the DNAPK inhibitor is a co-crystal that includes Compound 1, Compound 2 or Compound 3, and adipic acid. In some embodiments, the ratio of adipic acid to any of Compound 1, Compound 2 or Compound 3 is about 5 to 0.5, or any ratios in between. In some embodiments, the ratio of adipic acid to any of Compound 1, Compound 2 or Compound 3 is about 4 to 0.5, or any ratios in between. In some embodiments, the ratio of adipic acid to any of Compound 1, Compound 2 or Compound 3 is about 3 to 0.5, or any ratios in between. In some embodiments, the ratio of adipic acid to any of Compound 1, Compound 2 or Compound 3 is about 2 to 0.5, or any ratios in between. In some embodiments, the ratio of adipic acid to any of Compound 1, Compound 2 or Compound 3 is about 2 to 1.0, or any ratios in between. In some embodiments, the NHEJ inhibitors are compounds represented by Structural Formula I, I', II, II', II", II''', III, III', or any combinations thereof.

In some embodiments, provided herein are methods of treating a subject having a disease or condition in need of editing one or more target genomic regions in a cell(s) of the subject, comprising administering to one or more cells a genomic editing system and a DNAPK inhibitor.

In some embodiments, the methods provided herein are used to modify expression of a gene, an RNA molecule, a protein, a group of proteins, or downstream proteins in a pathway. Such modification can be used to treat a disease, a dysfunction, abnormal organismal homeostasis, either acquired or inherited or those due to the aging process. As used herein, the term "modify" or "modifying" includes modulating, enhancing, decreasing, increasing, inserting, deleting, knocking-out, knocking-in, and the like.

One of skill in the art understands that diseases, either acquired or inherited, or otherwise obtained, involve a dysregulation of homeostatic mechanisms including involvement of gene or protein function. To this end, a skilled artisan can use the methods provided herein to modulate, modify, enhance, decrease, or provide an otherwise gene function in a subject.

Modifying expression of gene and consequent protein expression in a cell(s) can be achieved by the methods provided herein, for example, by specific editing (e.g. replacing, inserting or deleting, any combinations thereof) a nucleic acid sequence in any of an exon, an intron, a transcription start site, a promoter region, an enhancer region, a silencer region, an insulator region, an antirepressor, a post translational regulatory element, a polyadenylation signal (e.g. minimal poly A), a conserved region, a transcription factor binding site, or any combinations thereof.

In some embodiments, the methods, kits and compositions provided herein are used to treat a subject that has cancer. The method of treating a subject having a cancer or cancer related condition comprises administering to a cell(s) of the subject a DNAPK inhibitor and a genome editing system. The administration of the DNAPK inhibitor and the genome editing system can be in vivo or ex vivo.

The cancer can be of any kind of cancer. Cancer includes solid tumors such as breast, ovarian, prostate, lung, kidney, gastric, colon, testicular, head and neck, pancreas, brain, melanoma, and other tumors of tissue organs and cancers of the blood cells, such as lymphomas and leukemias, including acute myelogenous leukemia, chronic lymphocytic leukemia, T cell lymphocytic leukemia, and B cell lymphomas. The cancers can include melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum.

In some embodiments, the methods, kits and compositions provided herein are used to treat a subject having any one or more of the following cancers: Acute lymphoblastic leukemia (ALL), Acute myeloid leukemia, Adrenocortical carcinoma, AIDS-related cancers, AIDS-related lymphoma, Anal cancer, Appendix cancer, Astrocytoma, childhood cerebellar or cerebral, Basal-cell carcinoma, Bile duct cancer, extrahepatic (see cholangiocarcinoma), Bladder cancer, Bone tumor, osteosarcoma/malignant fibrous histiocytoma, Brainstem glioma, Brain cancer, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt's lymphoma, Carcinoid tumor, childhood, Carcinoid tumor, gastrointestinal, Carcinoma of unknown primary, Central nervous system lymphoma, primary, Cerebellar astrocytoma, childhood, Cerebral astrocytoma/malignant glioma, childhood, Cervical cancer, Childhood cancers, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, Ependymoma, Epitheliod Hemangioendothelioma (EHE), Esophageal cancer, Ewing's sarcoma in the Ewing family of tumors, Extracranial germ cell tumor, Extragonadal germ cell tumor, Extrahepatic bile duct cancer, Eye cancer, intraocular melanoma, Eye cancer, retinoblastoma, Gallbladder cancer, Gastric (stomach) cancer, Gastrointestinal carcinoid tumor, Gastrointestinal stromal tumor (GIST), Germ cell tumor: extracranial, extragonadal, or ovarian, Gestational trophoblastic tumor, Glioma of the brain stem, Glioma, childhood cerebral astrocytoma, Glioma, childhood visual pathway and hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, childhood, Intraocular melanoma, Islet cell carcinoma (endocrine pancreas), Kaposi sarcoma, Kidney cancer (renal cell cancer), Laryngeal cancer, Leukaemias, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukaemia), Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphomas, AIDS-related Lymphoma, Burkitt Lymphoma, cutaneous T-Cell Lymphoma, Hodgkin Lymphomas, Non-Hodgkin (an old classification of all lymphomas except Hodgkin's) Lymphoma, primary central nervous system Macroglobulinemia, Waldenstrom, Male breast cancer, Malignant fibrous histiocytoma of bone/osteosarcoma, Medulloblastoma, childhood Melanoma, Melanoma, intraocular (eye), Merkel cell cancer, Mesothelioma, adult malignant Mesothelioma, childhood Metastatic squamous neck cancer with occult primary, Mouth cancer, Multiple endocrine neoplasia syndrome Multiple myeloma/plasma cell neoplasm, Mycosis fungoides, Myelodysplastic syndromes, Myelodysplastic/myeloproliferative diseases, Myelogenous leukemia, chronic Myeloid leukemia, adult acute Myeloid leukemia, childhood acute Myeloma, multiple (cancer of the bone-marrow), Myeloproliferative disorders, chronic Myxoma, Nasal cavity and paranasal sinus cancer, Nasopharyngeal carcinoma, Neuroblastoma, Non-Hodgkin lymphoma, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter caner, transitional cell cancer, Retinoblastoma, Rhabdomyosarcoma, Salivary gland cancer, Sarcoma, Ewing family of tumors, Kaposi Sarcoma, soft tissue Sarcoma, uterine sarcoma, Sézary syndrome, Skin cancer (non-melanoma), Skin cancer (melanoma), Skin carcinoma, Merkel cell, Small cell lung cancer, Small intestine cancer, Soft tissue sarcoma, Squamous cell carcinoma—see skin cancer (non-melanoma), Squamous neck cancer with occult primary, metastatic, Stomach cancer, Supratentorial primitive neuroectodermal tumor, T-Cell lymphoma, cutaneous (Mycosis Fungoides and Sézary syndrome), Testicular cancer, Throat cancer, Thymoma, Thymoma and thymic carcinoma, Thyroid cancer, Thyroid cancer, Transitional cell cancer of the renal pelvis and ureter, Gestational Trophoblastic tumor, Unknown primary site carcinoma of adult, Unknown primary site cancer of, childhood, Ureter and renal pelvis, transitional cell cancer, Urethral cancer, Uterine cancer, endometrial cancer, Uterine sarcoma, Vaginal cancer, Visual pathway and hypothalamic glioma, Vulvar cancer, Waldenstrom macroglobulinemia, or Wilms tumor (kidney cancer).

In some embodiments, exemplary target genes associated with cancer include ABL1, ABL2, ACSL3, AF15Q14, AF1Q, AF3p21, AF5q31, AKAP9, A Tl, AKT2, ALDH2, AL, AL017, APC, ARHGEF12, ARHH, ARID1A, ARID2, ARNT, ASPSCR1, ASXL1, ATF1, ATIC, ATM, ATRX, AXIN1, BAP1, BCL10, BCL11A, BCL11B, BCL2, BCL3, BCL5, BCL6, BCL7A, BCL9, BCOR, BCR, BHD, BIRC3, BLM, BMPRIA, BRAF, BRCA1, BRCA2, BRD3, BRD4, BRIPI, BTG1, BUB 1B, C12orf9, C15orf21, C15orf55, C16orf75, C2orf44, CAMTA1, CARD11, CARS, CBFA2T1, CBFA2T3, C.BFB, CBL, CBLB, CBLC, CCDC6, CCNB1IP1, CCND1, CCND2, CCND3, CCNE1, CD273, CD274, CD74, CD79A, CD79B, CDH1, CDH11, CDK12, CDK4, CDK6, CD N2A, CD N2a(p14), CD N2C, CDX2, CEBPA, CEP1, CHCHD7, CHEK2, CHIC2, CHN1, CIC, Cin A, CLTC, CLTCL1, CMKOR1, CNOT3, COL1 A1, COPEB, COX6C, CREB1, CREB3L1, CREB3L2, CREBBP, CRLF2, CRTC3, CTNNB1, CYLD, DIOS 170, DAXX, DDB2, DDIT3, DDX10, DDX5, DDX6, DEK, D10ER1, DNM2, DNMT3A, DUX4, EBFI, ECT2L, EGFR, E1F4A2, ELF4, ELK4, ELKS, ELL, ELN, EML4, EP300, EPS 15, ERBB2, ERCC2, ERCC3, ERCC4, ERCC5, ERG, ETV1, ETV4, ETV5, ETV6, EVI1, EWSR1, EXT1, EXT2, EZH2, EZR, FACL6, FAM22A, FAM22B, FAM46C, 1ANCA, EANCC, FANCD2, FANCE, FANCF, FANCG, FBXO1 1, FBXW7, FCGR2B, FEV, FGFR1, FGFRIOP, FGFR2, FGFR3, FTI, FIIIT, FIP1L1, FLU, F1127352, FLT3, FNBP1, FOXL2, FOXOIA, FOX03A, FOXP1, FSTL3, FUBP1, FUS, FVT1, GAS7, GATA1, GATA2, GATA3, GMPS, GNA11, GNAQ, GNAS, GOLGA5, GOPC, GPC3, GPHN, GRAF, H3F3A, IICMOGT-1, IIEAB, HERPUD1, IIEY1, IIIP1, HIST1IT3B, IIIST1II4I, IILF, HLXB9, HMGA1, HMGA2, HNRNPA2BI, HOOK3, HOXA11, HOXA13, HOXA9, HOXC11, HOXC13, HOXD11, HOXD13, HRAS, IIRPT2, HSPCA, HSPCB, IDH1, IDH2, IGH, IGK, IGL, IKZF1, IL2, TL21R, IL6ST, IL7R, IRF4, IRTA1, ITK, JAK1, JAK2, JAK3, JAZF1, JUN, KCNJS, KDMSA, KDMSC, KDM6A, KDR, KIAA1549, KIFSB, KIT, KLF4, KLK2, KRAS, KTN1, LAF4, LASPI, LCK, LCP1, LCX, LHFP, LIFR, LMO1, LM02, LPP, LRIG3, LYL1, MADH4, MAF, MAFB, MALT1, MAML2, MAP2KL MAP2K2, MAP2K4, MAX, MDM2, MDM4, MDS1, MDS2, MECT1, MED12, MEN1, MET, MITF, MKLI, MLF1, MLII1, MLL, MLL2, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYST4, NACA, NBS1, NCOA1, NCOA2, NCOA4, NDRG1, NF1, NF2, NFE2L2, NFIB, NFKB2, NIN, NKX2-1, NONO, NOTCH I, NOTCH2, NPM1, NR4A3, NRAS, NSD1, NT5C2, NTRK1, NTRK3, NUMA1, NUP214, NUP98, OLIG2, OMD, P2RY8, PAFAH1B2, PALB 2, PAX3, PAX5, PAX7, PAX8, PBRM1, PBX1, PCM1, PCSK7, PDE4DIP, PDGFB, PDGFRA, PDGFRB, PERI, PIIF6, PHOX2B, PICALM, PIK3CA, PIK3R1, PIM1, PLAG 1, PML, PMSI, PMS2, PMX1, PNUTL1, POTI, POU2AF1, POU5F1, PPARG, PPP2R1A, PRCC, PRDM1, PRDM16, PRF1, PRKAR1 A, PRO1073, PSIP2, PTCH, PTEN, PTPN11, RAB5EP, RAC1, RAD51L1, RAFI, RALGDS, RANBP17, RAPIGDSI, RARA, RBI, RBM15, RECQL4, REL, RET, RNF43, ROSI, RPL10, RPL22, RPL5, RPN1, RUNDC2A, RUNX1, RUNXBP2, SBDS, SDC4, SDH5, SDHB, SDHC, SDHD, SEPT6, SET, SETBP1, SETD2, SF3B1, SFPQ, SFRS3, SH2B3, SH3GL1, SIL, SLC34A2, SLC45A3, SMARCA4, SMARCB1, SMARCE1, SMO, SOCS1, SOX2, SRGAP3, SRSF2, SSI8, SS18L1, SSH3BP1, SSX1, SSX2, SSX4, STAT3, STK11, STL, SUFU, SIJZ12, SYK, TAF15, TALI, TAL2, TCEA1, TCF1, TCF12, TCF3, TCF7L2, TCL1A, TCL6, TERT, TET2, TFE3, TFEB, TFG, TFPT, TFRC, THRAP3, TIF1, TLX1, TLX 3, TMPRSS2, TNFAIP3, TNFRSF14, TNFRSF17, TNFRSF6, TOPI, TP53, TPM3, TPM4, TPR, TRA, TRAF7, TRB, TRD, TRIM27, TRIM33, TRIP11, TSC1, TSC2, TSHR, TTL, U2AF1, USP6, VHL, VTUA, WAS, WHSCI, WHSC1L1, WIF1, WRN, WT1, WTX, WWTR1, XPA, XPC, XPO1, YWHAE, ZNF145, ZNF198, ZNF278, ZNF331, ZNF384, ZNF521, ZNF9, ZRSR2 or any combinations thereof.

In some embodiments, the methods provided herein are used to treat a subject that has an inherited disorder The method of treating a subject having a genetic disease or condition or inherited disorder comprises administering to a cell(s) of the subject a DNAPK inhibitor and a genome editing system. The administration of or the DNAPK inhibitor and the genome editing system can be in vivo or ex vivo.

The inherited disorder can result from mutations or duplications in chromosomal regions (e.g. from point mutations, deletions, insertions, frameshift, chromosomal duplications or deletions). The inherited disorder can be any inherited disorder.

In some embodiments, the inherited disorder is 22q11.2 deletion syndrome, Angelman syndrome, Canavan disease, Charcot-Marie-Tooth disease, Color blindness, Cri du chat, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Spinal muscular atrophy, Spinal muscular atrophy, Tay-Sachs disease, Turner syndrome, a hemoglobinopathy or any combinations thereof.

In some embodiments, the inherited disorder is 1p36 deletion syndrome, 18p deletion syndrome, 21-hydroxylase deficiency, 47 XXX (triple X syndrome), 47 XXY (Klinefelter syndrome), 5-ALA dehydratase-deficient porphyria, ALA dehydratase deficiency, 5-aminolaevulinic dehydratase deficiency porphyria, 5p deletion syndrome, Cri du chat (AKA 5p-syndrome), ataxia telangiectasia (AKA A-T), alpha 1-antitrypsin deficiency (AAT), aceruloplasminemia, achondrogenesis type II (ACG2), achondroplasia (ACH), Acid beta-glucosidase deficiency, Gaucher disease (any type, e.g. type 1, type 2, type 3), Acrocephalosyndactyly (Apert), Apert syndrome, acrocephalosyndactyly (any type, e.g., type 1, type 2, type 3, type 5), Pfeiffer syndrome, Acrocephaly, Acute cerebral Gaucher's disease, acute intermittent porphyria, (AIP) ACY2 deficiency, Alzheimer's disease (AD), Adelaide-type cranio-synostosis, Muenke syndrome, Adenomatous Polyposis Coli, familial adenomatous polyposis, Adenomatous Polyposis of the Colon, familial adenomatous polyposis (ADP), adenylosuccinate lyase deficiency, Adrenal gland disorders, Adrenogenital syndrome, Adrenoleukodystrophy, androgen insensitivity syndrome (AIS), alkaptonuria (AKU), ALA dehydratase porphyria, ALA-D porphyria, ALA dehydratase deficiency, Alagille syndrome, Albinism, Alcaptonuria, alkaptonuria, Alexander disease, alkaptonuria, Alkaptonuric ochronosis, alkaptonuria, alpha-1 proteinase inhibitor disease, alpha-1 related emphysema, Alpha-galactosidase A deficiency, Fabry disease, Alstom syndrome, Alexander disease (ALX), Amelogenesis imperfecta, Amino levulinic acid dehydratase deficiency, Aminoacylase 2 deficiency, Canavan disease, Anderson-Fabry disease, androgen insensitivity syndrome, Anemia, hereditary sideroblastic, X-linked sideroblastic anemiasplenic and/or familial anemia, Angiokeratoma Corporis Diffusum, Angiokeratoma diffuse, Angiomatosis retinae, von Hippel-Lindau disease, APC resistance, Leiden type, factor V Leiden thrombophilia, Apert syndrome, AR deficiency, androgen insensitivity syndrome, Charcot-Marie-Tooth disease (any type, e.g., CMT1, CMTX, CMT2, CMT4, severe early onset CMT), Arachnodactyly, Marfan syndrome, ARNSHL, Nonsyndromic deafness (autosomal recessive, autosomal dominant, x-linked, or mitochondria), Arthro-ophthalmopathy, hereditary progressive, Stickler syndrome (e.g. COL2A1, COL11A1, COL11A2, COL9A1), Arthrochalasis multiplex congenita, Ehlers-Danlos syndrome (e.g. hypermobility type, arthrochalasia type, classical type, vascular type, kyphoscoliosis type, dermatosparaxis type) Asp deficiency, Aspa deficiency, Aspartoacylase deficiency, ataxia telangiectasia, Autism-Dementia-Ataxia-Loss of Purposeful Hand Use syndrome, Rett syndrome, autosomal dominant juvenile ALS, Autosomal dominant opitz G/BBB syndrome, autosomal recessive form of juvenile ALS type 3, Amyotrophic lateral sclerosis (any type; e.g. ALS1, ALS2, ALS3, ALS4, ALS5, ALS5, ALS6, ALS7, ALS5, ALS6, ALS10, ALS11, ALS12, ALS13, ALS14, ALS15, ALS16, ALS17, ALS18, ALS19, ALS20, ALS21, ALS22, FTDALS1, FTDALS2, FTDALS3, FTDALS4, FTDALS4, IBMPFD2), Autosomal recessive nonsyndromic hearing loss, Autosomal Recessive Sensorineural Hearing Impairment and Goiter, Pendred syndrome, Alexander disease (AxD), Ayerza syndrome, familial pulmonary arterial hypertension, B variant of the Hexosaminidase GM2 gangliosidosis, Sandhoff disease, BANF-related disorder, neurofibromatosis (any type, e.g., NF1, NF2, schwannomatosis), Beare-Stevenson cutis gyrata syndrome, Benign paroxysmal peritonitis, Benjamin syndrome, beta-thalassemia, BH4 Deficiency, tetrahydrobiopterin deficiency, Bilateral Acoustic Neurofibromatosis, biotinidase deficiency, bladder cancer, Bleeding disorders, factor V Leiden thrombophilia, Bloch-Sulzberger syndrome, incontinentia pigmenti, Bloom syndrome, Bone diseases, Bourneville disease, tuberous sclerosis, Brain diseases, prion disease, breast cancer, Birt-Hogg-Dubé syndrome, Brittle bone disease, osteogenesis imperfecta, Broad Thumb-Hallux syndrome, Rubinstein-Taybi syndrome, Bronze Diabetes, hemochromatosis, Bronzed cirrhosis, Bulbospinal muscular atrophy, X-linked Spinal and bulbar muscular atrophy, Burger-Grutz syndrome, lipoprotein lipase deficiency, familial CADASIL syndrome, CGD Chronic granulomatous disorder, Campomelic dysplasia, Cancer Family syndrome, hereditary nonpolyposis colorectal cancer, breast cancer, bladder cancer, Carboxylase Deficiency, Multiple Late-Onset biotinidase deficiency, Cat cry syndrome, Caylor cardiofacial syndrome, Ceramide trihexosidase deficiency, Cerebelloretinal Angiomatosis, familial von Hippel-Lindau disease, Cerebral arteriopathy, CADASIL syndrome, Cerebral autosomal dominant ateriopathy, CADASIL syndrome, Cerebroatrophic Hyperammonemia, Rett syndrome, Cerebroside Lipidosis syndrome, Charcot disease, CHARGE syndrome, Chondrodystrophia, Chondrodystrophy syndrome, Chondrodystrophy with sensorineural deafness, otospondylomegaepiphyseal dysplasia, Chondrogenesis imperfecta, Choreoathetosis self-mutilation hyperuricemia syndrome, Lesch-Nyhan syndrome, Classic Galactosemia, galactosemia, Cleft lip and palate, Stickler syndrome, Cloverleaf skull with thanatophoric dwarfism, Thanatophoric dysplasia (e.g. type 1 or type 2), Coffin-Lowry syndrome (CLS), Cockayne syndrome, Coffin-Lowry syndrome, collagenopathy types II and XI, familial Nonpolyposis, hereditary nonpolyposis colorectal cancer, familial Colon cancer, familial adenomatous polyposis, Colorectal cancer, Complete HPRT deficiency, Lesch-Nyhan syndrome, Complete hypoxanthine-guanine phosphoribosyl transferase deficiency, Compression neuropathy, hereditary neuropathy with liability to pressure palsies, Connective tissue disease, Conotruncal anomaly face syndrome, Cooley's Anemia, beta-thalassemia, Copper storage disease, Wilson's disease, Copper transport disease, Menkes disease, Coproporphyria, hereditary coproporphyria, Coproporphyrinogen oxidase deficiency, Cowden syndrome, CPX deficiency, Craniofacial dysarthrosis, Crouzon syndrome, Craniofacial Dysostosis, Crouzon syndrome, Crohn's disease, fibrostenosing, Crouzon syndrome, Crouzon syndrome with acanthosis nigricans, Crouzonodermoskeletal syndrome, Crouzonodermoskeletal syndrome, Cockayne syndrome (CS), Cowden syndrome, Curschmann-Batten-Steinert syndrome, cutis gyrata syndrome of Beare-Stevenson, Beare-Stevenson cutis gyrata syndrome, D-glycerate dehydrogenase deficiency, hyperoxaluria, primary, Dappled metaphysis syndrome, spondyloepimetaphyseal dysplasia, Strudwick type, Dementia Alzheimer's type (DAT), Genetic hypercalciuria, Dent's disease, muscular dystrophy (e.g. Duchenne and Becker types), Deafness with goiter, Pendred syndrome, Deafness-retinitis pigmentosa syndrome, Usher syndrome, Deficiency disease, Phenylalanine Hydroxylase, Degenerative nerve diseases, de Grouchy syndrome 1, De Grouchy syndrome, Dejerine-Sottas syndrome, Delta-aminolevulinate dehydratase deficiency porphyria, Dementia, CADASIL syndrome, demyelinogenic leukodystrophy, Alexander disease, Dermatosparactic type of Ehlers-Danlos syndrome, Dermatosparaxis, inherited developmental disabilities, distal hereditary motor neuropathy (dHMN), distal hereditary motor neuropathy (e.g. DHMN-V), DHTR deficiency, androgen insensitivity syndrome, Diffuse Globoid Body Sclerosis, Krabbe disease, Di George's syndrome, Dihydrotestosterone receptor deficiency, androgen insensitivity syndrome, distal hereditary motor neuropathy, Myotonic dystrophy (type 1 or type 2), distal spinal muscular atrophy (any type, including e.g. type 1, type 2, type 3, type 4, type 5, type 6), Duchenne/Becker muscular dystrophy, Dwarfism (any kind, e.g. achondroplastic, achondroplasia, thanatophoric dysplasia), Dwarfism-retinal atrophy-deafness syndrome, Cockayne syndrome, dysmyelinogenic leukodystrophy, Alexander disease, Dystrophia myotonica, dystrophia retinae pigmentosa-dysostosis syndrome, Usher syndrome, Early-Onset familial alzheimer disease (EO-FAD), Alzheimer disease (including e.g. type 1, type 2, type 3, or type 4) Ekman-Lobstein disease, osteogenesis imperfecta, Entrapment neuropathy, hereditary neuropathy with liability to pressure palsies, erythropoietic protoporphyria (EPP), Erythroblastic anemia, beta-thalassemia, Erythrohepatic protoporphyria, Erythroid 5-aminolevulinate synthetase deficiency, X-linked sideroblastic anemia, Eye cancer, retinoblastoma FA—Friedreich ataxia, Friedreich's ataxia, FA, fanconi anemia, Facial injuries and disorders, factor V Leiden thrombophilia, FALS, amyotrophic lateral sclerosis, familial acoustic neuroma, familial adenomatous polyposis, familial Alzheimer disease (FAD), familial amyotrophic lateral sclerosis, amyotrophic lateral sclerosis, familial dysautonomia, familial fat-induced hypertriglyceridemia, lipoprotein lipase deficiency, familial, familial hemochromatosis, hemochromatosis, familial LPL deficiency, lipoprotein lipase deficiency, familial, familial nonpolyposis colon cancer, hereditary nonpolyposis colorectal cancer, familial paroxysmal polyserositis, familial PCT, porphyria cutanea tarda, familial pressure-sensitive neuropathy, hereditary neuropathy with liability to pressure palsies, familial primary pulmonary hypertension (FPPH), familial vascular leukoencephalopathy, CADASIL syndrome, FAP, familial adenomatous polyposis, FD, familial dysautonomia, Ferrochelatase deficiency, ferroportin disease, Haemochromatosis (any type, e.g., type 1, type 2A, type 2B, type 3, type 4, neonatal haemochromatosis, acaeruloplasminaemia, congenital atransferrinaemia, gracile syndrome), Periodic fever syndrome, Familial Mediterranean fever (FMF), FG syndrome, FGFR3-associated coronal synostosis, Fibrinoid degeneration of astrocytes, Alexander disease, Fibrocystic disease of the pancreas, Folling disease, fra(X) syndrome, fragile X syndrome, Fragilitas ossium, osteogenesis imperfecta, FRAXA syndrome, Friedreich's ataxia (FRDA), G6PD deficiency, Galactokinase deficiency disease, galactosemia, Galactose-1-phosphate uridyl-transferase deficiency disease, galactosemia, Galactosylceramidase deficiency disease, Krabbe disease, Galactosylceramide lipidosis, Krabbe disease, galactosylcerebrosidase deficiency, galactosylsphingosine lipidosis, GALC deficiency, GALT deficiency, galactosemia, Gaucher-like disease, pseudo-Gaucher disease, GBA deficiency, Genetic brain disorders, genetic emphysema, genetic hemochromatosis, hemochromatosis, Giant cell hepatitis, neonatal, Neonatal hemochromatosis, GLA deficiency, Glioblastoma, retinal, retinoblastoma, Glioma, retinal, retinoblastoma, globoid cell leukodystrophy (GCL, GLD), Krabbe disease, globoid cell leukoencephalopathy, Glucocerebrosidase deficiency, Glucocerebrosidosis, Glucosyl cerebroside lipidosis, Glucosylceramidase deficiency, Glucosylceramide beta-glucosidase deficiency, Glucosylceramide lipidosis, Glyceric aciduria, hyperoxaluria, primary, Glycine encephalopathy, Nonketotic hyperglycinemia, Glycolic aciduria, hyperoxaluria, primary, GM2 gangliosidosis, Tay-Sachs disease, Goiter-deafness syndrome, Pendred syndrome, Graefe-Usher syndrome, Usher syndrome, Gronblad-Strandberg syndrome, pseudoxanthoma elasticum, Haemochromatosis, hemochromatosis, Hallgren syndrome, Usher syndrome, Harlequin type ichthyosis, Hb S disease, hypochondroplasia (HCH), hereditary coproporphyria (HCP), Head and brain malformations, Hearing disorders and deafness, Hearing problems in children, HEF2A, HEF2B, Hematoporphyria, porphyria, Heme synthetase deficiency, Hemochromatoses, hemoglobin M disease, methemoglobinemia beta-globin type, Hemoglobin S disease, hemophilia, hepatoerythropoietic porphyria (HEP), hepatic AGT deficiency, hyperoxaluria, primary, Hepatolenticular degeneration syndrome, Wilson disease, Hereditary arthro-ophthalmopathy, Stickler syndrome, Hereditary dystopic lipidosis, Hereditary hemochromatosis (HHC), hemochromatosis, Hereditary hemorrhagic telangiectasia (HHT), Hereditary Inclusion Body Myopathy, skeletal muscle regeneration, Hereditary iron-loading anemia, X-linked sideroblastic anemia, Hereditary motor and sensory neuropathy, Hereditary motor neuronopathy, type V, distal hereditary motor neuropathy, Hereditary multiple exostoses, Hereditary nonpolyposis colorectal cancer, Hereditary periodic fever syndrome, Hereditary Polyposis Coli, familial adenomatous polyposis, Hereditary pulmonary emphysema, Hereditary resistance to activated protein C, factor V Leiden thrombophilia, Hereditary sensory and autonomic neuropathy type III, familial dysautonomia, Hereditary spastic paraplegia, infantile-onset ascending hereditary spastic paralysis, Hereditary spinal ataxia, Friedreich's ataxia, Hereditary spinal sclerosis, Friedreich's ataxia, Herrick's anemia, Heterozygous OSMED, Weissenbacher-Zweymüller syndrome, Heterozygous otospondylomegaepiphyseal dysplasia, Weissenbacher-Zweymüller syndrome, HexA deficiency, Tay-Sachs disease, Hexosaminidase A deficiency, Tay-Sachs disease, Hexosaminidase alpha-subunit deficiency (any variant, e.g. variant A, variant B), Tay-Sachs disease, HFE-associated hemochromatosis, hemochromatosis, HGPS, Progeria, Hippel-Lindau disease, von Hippel-Lindau disease, hemochromatosis (HLAH), distal hereditary motor neuropathy (HMN V), hereditary nonpolyposis colorectal cancer (HNPCC), hereditary neuropathy with liability to pressure palsies (HNPP), homocystinuria, Homogentisic acid oxidase deficiency, alkaptonuria, Homogentisic acidura, alkaptonuria, Homozygous porphyria cutanea tarda, hepatoerythropoietic porphyria, hyperoxaluria, primary (HP1), hyperoxaluria (HP2), hyperphenylalaninemia (HPA), HPRT—Hypoxanthine-guanine phosphoribosyltransferase deficiency, Lesch-Nyhan syndrome, HSAN type III, familial dysautonomia, familial dysautonomia (HSAN3), Hereditary Sensory Neuropathy (any type, e.g. HSN-I, HSN-II, HSN-III), familial dysautonomia, Human dermatosparaxis, Huntington's disease, Hutchinson-Gilford progeria syndrome, progeria, Hyperandrogenism, nonclassic type due to 21-hydroxylase deficiency, Hyperchylomicronemia, familial lipoprotein lipase deficiency, familial, Hyperglycinemia with ketoacidosis and leukopenia, propionic acidemia, Hyperlipoproteinemia type I, lipoprotein lipase deficiency, familial hyperoxaluria, primary hyperphenylalaninaemia, hyperphenylalaninemia, hyperphenylalaninemia, Hypochondrodysplasia, hypochondroplasia, Hypochondrogenesis, Hypochondroplasia, Hypochromic anemia, X-linked sideroblastic anemia, Hypoxanthine phosphoribosyltransferse (HPRT) deficiency, Lesch-Nyhan syndrome, infantile-onset ascending hereditary spastic paralysis (IAHSP), ICF syndrome, Immunodeficiency, centromere instability and facial anomalies syndrome, Idiopathic hemochromatosis, hemochromatosis, type 3, Idiopathic neonatal hemochromatosis, hemochromatosis, neonatal, Idiopathic pulmonary hypertension, Immune system disorders, X-linked severe combined immunodeficiency, Incontinentia pigmenti, Infantile cerebral Gaucher's disease, Infantile Gaucher disease, infantile-onset ascending hereditary spastic paralysis, Infertility, inherited emphysema, inherited tendency to pressure palsies, hereditary neuropathy with liability to pressure palsies, Insley-Astley syndrome, otospondylomegaepiphyseal dysplasia, Intermittent acute porphyria syndrome, acute intermittent porphyria, Intestinal polyposis-cutaneous pigmentation syndrome, Peutz-Jeghers syndrome, incontinentia pigmenti (IP), Iron storage disorder, hemochromatosis, Isodicentric 15, isodicentric 15, Isolated deafness, nonsyndromic deafness, Jackson-Weiss syndrome, Joubert syndrome, Juvenile Primary Lateral Sclerosis (JPLS), juvenile amyotrophic lateral sclerosis, Juvenile gout, choreoathetosis, mental retardation syndrome, Lesch-Nyhan syndrome, juvenile hyperuricemia syndrome, Lesch-Nyhan syndrome, Jackson-Weiss syndrome (JWS), spinal and bulbar muscular atrophy, Kennedy disease, spinal and bulbar muscular atrophy, Kennedy spinal and bulbar muscular atrophy, spinal and bulbar muscular atrophy, Kerasin histiocytosis, Kerasin lipoidosis, Kerasin thesaurismosis, ketotic glycinemia, propionic acidemia, ketotic hyperglycinemia, propionic acidemia, Kidney diseases, hyperoxaluria, primary, Kniest dysplasia, Krabbe disease, Kugelberg-Welander disease, spinal muscular atrophy, Lacunar dementia, CADASIL syndrome, Langer-Saldino achondrogenesis, Langer-Saldino dysplasia, Late-onset Alzheimer disease, late-onset Krabbe disease (LOKD), Krabbe disease, Learning Disorders, Learning disability, Lentiginosis, perioral, Peutz-Jeghers syndrome, Lesch-Nyhan syndrome, Leukodystrophies, leukodystrophy with Rosenthal fibers, Alexander disease, Leukodystrophy, spongiform, Li-Fraumeni syndrome (LFS), Li-Fraumeni syndrome, Lipase D deficiency, lipoprotein lipase deficiency, familial LIPD deficiency, lipoprotein lipase deficiency, familial Lipidosis, cerebroside, Lipidosis, ganglioside, infantile, Tay-Sachs disease, Lipoid histiocytosis (kerasin type), lipoprotein lipase deficiency, familial Liver diseases, galactosemia, Lou Gehrig disease, Louis-Bar syndrome, ataxia telangiectasia, Lynch syndrome, hereditary nonpolyposis colorectal cancer, Lysyl-hydroxylase deficiency, Machado-Joseph disease, Spinocerebellar ataxia (any type, e.g. SCA1, SCA2, SCA3, SCA 18, SCA20, SCA21, SCA23, SCA26, SCA28, SCA29), Male breast cancer, breast cancer, Male genital disorders, Malignant neoplasm of breast, breast cancer, malignant tumor of breast, breast cancer, Malignant tumor of urinary bladder, bladder cancer, Mammary cancer, breast cancer, Marfan syndrome, Marker X syndrome, fragile X syndrome, Martin-Bell syndrome, fragile X syndrome, McCune-Albright syndrome, McLeod syndrome, MEDNIK syndrome, Mediterranean Anemia, beta-thalassemia, Mega-epiphyseal dwarfism, otospondylomegaepiphyseal dysplasia, Menkea syndrome, Menkes disease, Menkes disease, Mental retardation with osteocartilaginous abnormalities, Coffin-Lowry syndrome, Metabolic disorders, Metatropic dwarfism, type II, Kniest dysplasia, Metatropic dysplasia type II, Kniest dysplasia, Methemoglobinemia (any type, e.g. congenital, beta-globin type, congenital methemoglobinemia type II), methylmalonic acidemia, Marfan syndrome (MFS), MHAM, Cowden syndrome, Micro syndrome, Microcephaly, MMA, methylmalonic acidemia, Menkes disease (AKA MK or MNK), Monosomy 1p36 syndrome, Motor neuron disease, amyotrophic lateral sclerosis, amyotrophic lateral sclerosis, Movement disorders, Mowat-Wilson syndrome, Mucopolysaccharidosis (MPS I), Mucoviscidosis, Multi-Infarct dementia, CADASIL syndrome, Multiple carboxylase deficiency, late-onset, biotinidase deficiency, Multiple hamartoma syndrome, Cowden syndrome, Multiple neurofibromatosis, Muscular dystrophy (any type, including, e.g., Duchenne and Becker type), Myotonia atrophica, myotonic dystrophy, Myotonia dystrophica, Nance-Insley syndrome, otospondylomegaepiphyseal dysplasia, Nance-Sweeney chondrodysplasia, otospondylomegaepiphyseal dysplasia, NBIA1, pantothenate kinase-associated neurodegeneration, Neill-Dingwall syndrome, Cockayne syndrome, Neuroblastoma, retinal, retinoblastoma, Neurodegeneration with brain iron accumulation type 1, pantothenate kinase-associated neurodegeneration, Neurologic diseases, Neuromuscular disorders, distal hereditary motor neuronopathy, Niemann-Pick, Niemann-Pick disease, Noack syndrome, Nonketotic hyperglycinemia, Glycine encephalopathy, Non-neuronopathic Gaucher disease, Non-phenylketonuric hyperphenylalaninemia, tetrahydrobiopterin deficiency, nonsyndromic deafness, Noonan syndrome, Norrbottnian Gaucher disease, Ochronosis, alkaptonuria, Ochronotic arthritis, alkaptonuria, Ogden syndrome, osteogenesis imperfecta (OI), Osler-Weber-Rendu disease, Hereditary hemorrhagic telangiectasia, OSMED, otospondylomegaepiphyseal dysplasia, osteogenesis imperfecta, Osteopsathyrosis, osteogenesis imperfecta, Osteosclerosis congenita, Oto-spondylo-megaepiphyseal dysplasia, otospondylomegaepiphyseal dysplasia, otospondylomegaepiphyseal dysplasia, Oxalosis, hyperoxaluria, primary, Oxaluria, primary, hyperoxaluria, primary, pantothenate kinase-associated neurodegeneration, Patau Syndrome (Trisomy 13), PBGD deficiency, acute intermittent porphyria, PCC deficiency, propionic acidemia, porphyria cutanea tarda (PCT), PDM disease, Pendred syndrome, Periodic disease, Mediterranean fever, Familial Periodic peritonitis, Periorificial lentiginosis syndrome, Peutz-Jeghers syndrome, Peripheral nerve disorders, familial dysautonomia, Peripheral neurofibromatosis, Peroneal muscular atrophy, peroxisomal alanine:glyoxylate aminotransferase deficiency, hyperoxaluria, primary Peutz-Jeghers syndrome, Phenylalanine hydroxylase deficiency disease, Pheochromocytoma, von Hippel-Lindau disease, Pierre Robin syndrome with fetal chondrodysplasia, Weissenbacher-Zweymüller syndrome, Pigmentary cirrhosis, hemochromatosis, Peutz-Jeghers syndrome (PJS), pantothenate kinase-associated neurodegeneration (PKAN), PKU, phenylketonuria, Plumboporphyria, ALA deficiency porphyria, PMA, Polycystic kidney disease, polyostotic fibrous dysplasia, McCune-Albright syndrome, familial adenomatous polyposis, hamartomatous intestinal polyposis, polyps-and-spots syndrome, Peutz-Jeghers syndrome, Porphobilinogen synthase deficiency, ALA deficiency porphyria, porphyrin disorder, PPDX deficiency, variegate porphyria, Prader-Labhart-Willi syndrome, Prader-Willi syndrome, presenile and senile dementia, Primary ciliary dyskinesia (PCD), primary hemochromatosis, hemochromatosis, primary hyperuricemia syndrome, Lesch-Nyhan syndrome, primary senile degenerative dementia, procollagen type EDS VII, mutant, progeria, Hutchinson Gilford Progeria Syndrome, Progeria-like syndrome, Cockayne syndrome, progeroid nanism, Cockayne syndrome, progressive chorea, chronic hereditary (Huntington), Huntington's disease, progressively deforming osteogenesis imperfecta with normal sclerae, Osteogenesis imperfecta (any type, e.g. Type I, Type II, Type III-Type IV, Type V, Type VI, Type VII, Type VIII), proximal myotonic dystrophy (PROMM), propionic acidemia, propionyl-CoA carboxylase deficiency, protein C deficiency, protein S deficiency, protoporphyria, protoporphyrinogen oxidase deficiency, variegate porphyria, proximal myotonic dystrophy, Myotonic dystrophytype 2, proximal myotonic myopathy, pseudo-Gaucher disease, pseudoxanthoma elasticum, psychosine lipidosis, Krabbe disease, pulmonary arterial hypertension, pulmonary hypertension, pseudoxanthoma elasticum (PXE), pseudoxanthoma elasticum, retinoblastoma (Rb), Recklinghausen disease, Recurrent polyserositis, Retinal disorders, Retinitis pigmentosa-deafness syndrome, Usher syndrome, Retinoblastoma, Rett syndrome, RFALS type 3, Ricker syndrome, Riley-Day syndrome, familial dysautonomia, Roussy-Levy syndrome, Rubinstein-Taybi syndrome (RSTS), Rett syndrome (RTS), Rubinstein-Taybi syndrome, Rubinstein-Taybi syndrome, Sack-Barabas syndrome, disease, sarcoma family syndrome of Li and Fraumeni, Li-Fraumeni syndrome, SBLA syndrome (sarcoma, breast, leukemia, and adrenal gland syndrome), Li-Fraumeni syndrome, Spinal and bulbar muscular atrophy (SBMA), Schwannoma, acoustic, bilateral, neurofibromatosis type II, Schwartz-Jampel syndrome, X-linked severe combined immunodeficiency (SCIDX1), SED congenita, spondyloepiphyseal dysplasia congenita, SED Strudwick, spondyloepimetaphyseal dysplasia, Strudwick type, spondyloepiphyseal dysplasia congenita (SEDc), Spondyloepimetaphyseal dysplasia (SEMD), Strudwick type SEMD, senile dementia, severe achondroplasia with developmental delay and acanthosis nigricans, SADDAN disease, Shprintzen syndrome, Siderius X-linked mental retardation syndrome caused by mutations in the PHF8 gene, skeleton-skin-brain syndrome, Skin pigmentation disorders, spinal muscular atrophy (SMA), Spondylo-meta-epiphyseal dysplasia (SMED) (any type, e.g. Studwick type, type 1), Smith-Lemli-Opitz syndrome, Smith Magenis Syndrome, South-African genetic porphyria-infantile onset ascending spastic paralysis, infantile-onset ascending hereditary spastic paralysis, Speech and communication disorders, sphingolipidosis, Tay-Sachs, Tay-Sachs disease, spinal and bulbar muscular atrophy, spinal muscular atrophy, spinal muscular atrophy, distal type V, distal hereditary motor neuropathy, spinal muscular atrophy distal with upper limb predominance, distal hereditary motor neuropathy, spinocerebellar ataxia, spondyloepiphyseal dysplasia congenita, spondyloepiphyseal dysplasia, collagenopathy (any type, e.g. types II and XI), spondyloepimetaphyseal dysplasia, spondylometaphyseal dysplasia (SMD), spondyloepimetaphyseal dysplasia, spongy degeneration of central nervous system, spongy degeneration of the brain, spongy degeneration of white matter in infancy, sporadic primary pulmonary hypertension, SSB syndrome, steely hair syndrome, Menkes disease, Steinert disease, myotonic dystrophy, Steinert myotonic dystrophy syndrome, myotonic dystrophy, Stickler syndrome, stroke, CADASIL syndrome, Strudwick syndrome, subacute neuronopathic Gaucher disease, Swedish genetic porphyria, acute intermittent porphyria, acute intermittent porphyria, Swiss cheese cartilage dysplasia, Kniest dysplasia, Tay-Sachs disease, TD—thanatophoric dwarfism, thanatophoric dysplasia, TD with straight femurs and cloverleaf skull, thanatophoric dysplasia Type 2, Telangiectasia, cerebello-oculocutaneous, ataxia telangiectasia, Testicular feminization syndrome, androgen insensitivity syndrome, tetrahydrobiopterin deficiency, testicular feminization syndrome (TFM), androgen insensitivity syndrome, thalassemia intermedia, beta-thalassemia, Thalassemia Major, beta-thalassemia, thanatophoric dysplasia, Thrombophilia due to deficiency of cofactor for activated protein C, Leiden type, factor V Leiden thrombophilia, Thyroid disease, Tomaculous neuropathy, hereditary neuropathy with liability to pressure palsies, Total HPRT deficiency, Lesch-Nyhan syndrome, Total hypoxanthine-guanine phosphoribosyl transferase deficiency, Lesch-Nyhan syndrome, Treacher Collins syndrome, Trias fragilitis ossium, triple X syndrome, Triplo X syndrome, Trisomy 21Trisomy X, Troisier-Hanot-Chauffard syndrome, hemochromatosis, Tay-Sachs disease (TSD), Tuberous Sclerosis Complex (TSC), Tuberous sclerosis, Tumer-like syndrome, Noonan syndrome, UDP-galactose-4-epimerase deficiency disease, galactosemia, UDP glucose 4-epimerase deficiency disease, galactosemia, UDP glucose hexose-1-phosphate uridylyl-transferase deficiency, galactosemia, Undifferentiated deafness, nonsyndromic deafness, UPS deficiency, acute intermittent porphyria, Urinary bladder cancer, bladder cancer, UROD deficiency, Uroporphyrinogen decarboxylase deficiency, Uroporphyrinose synthase deficiency, acute intermittent porphyria, Usher syndrome, UTP hexose-1-phosphate uridylyltransferase deficiency, galactosemia, Van Bogaert-Bertrand syndrome, Van der Hoeve syndrome, Velocardiofacial syndrome, VHL syndrome, von Hippel-Lindau disease, Vision impairment and blindness, Alstrom syndrome, Von Bogaert-Bertrand disease, von Hippel-Lindau disease, Von Recklenhausen-Applebaum disease, hemochromatosis, von Recklinghausen disease, neurofibromatosis type I, Vrolik disease, osteogenesis imperfecta, Waardenburg syndrome, Warburg Sjo Fledelius Syndrome, Micro syndrome, Wilson disease (WD), Weissenbacher-Zweymüller syndrome, Werdnig-Hoffmann disease, spinal muscular atrophy, Williams Syndrome, Wilson disease, Wilson's disease, Wilson disease, Wolf-Hirschhom syndrome, Wolff Periodic disease, Weissenbacher-Zweymüller syndrome (WZS), Xeroderma pigmentosum, X-linked mental retardation and macroorchidism, fragile X syndrome, X-linked primary hyperuricemia, Lesch-Nyhan syndrome, X-linked severe combined immunodeficiency, X-linked sideroblastic anemia, X-linked spinal-bulbar muscle atrophy, spinal and bulbar muscular atrophy, X-linked uric aciduria enzyme defect, Lesch-Nyhan syndrome, X-SCID, X-linked severe combined immunodeficiency, X-linked sideroblastic anemia (XLSA), X-SCID, X-linked severe combined immunodeficiency, X-linked sideroblastic anemia (XLSA), XSCID, X-linked severe combined immunodeficiency, XXX syndrome, triple X syndrome, XXXX syndrome, XXXXX syndrome, XXXXX, XXY syndrome, XXY trisomy, Klinefelter syndrome, XYY syndrome, triplet repeat disorders, or any combinations thereof.

In embodiments, a specific post-transcriptional control modulator is targeted for modulation, modification, enhancement or decrease in activity by administering a DNAPK inhibitor and a genomic editing system. For example, post-transcriptional control modulators can include PARN, PAN, CPSF, CstF, PAP, PABP, PAB2, CFI, CFII, RNA triphosphatase, RNA gluanyltransferase, RNA methyl transferase, SAM synthase, ubiquitin-conjugating enzyme E2R, SR proteins SFRS1 through SFR11, hnRNP proteins (e.g. HNRNPA0, HNRNPA1, HNRNPA1L1, HNRNPA1L2, HNRNPA2, HNRNPA2B1, HNRNPAB, HNRNPB1, HNRNPC, HNRNPCL1, HNRNPD, HNRPDL, HNRNPF, HNRNHP1, HNRNPH2, HNRNPH3, HNRNPK, HNRNPL, HNRNPLL, HNRNPM, HNRNPR, HNRNPU, HNRNPUL1, HNRNPUL2, HNRNPUL3, ADAR, Mex 67, Mtr2, Nab2, Dead-box helicase, eIF4A, eIF4B, eIF4E, eIF4G, GEF, GCN2, PKR, HRI, PERK, eEF1, eEF2, GCN, eRF3, ARE-specific binding proteins, EXRN1, DCP1, DCP2, RCK/p54, CPEB, eIF4E, microRNAS and siRNAs, DICER, Ago proteins, Nonsense-mediated mRNA decay proteins, UPF3A, UPF3BeIF4A3, MLN51, Y14/MAGOH, MG-1, SMG-5, SMG-6, SMG-7 or any combinations thereof.

In some embodiments, genetic pathways associated with the cell cycle are modulated, enhanced or decreased in activity by administering a DNAPK inhibitor and a genomic editing system. Exemplary pathways and genes associated with the cell cycle include ATM, PMS2, FAS-L, MRE11, MLH1, FasR, NBS1, MSH6, Trail-L, RAD50, MSH2, Trail-R, 53BP1, RFC, TNF-Ct, P53, PCNA, TNF-R1, CHKE, MSH3, FADD, E2F1, MutS, homolog, TRADD, PML, MutL, homolog, R1P1, FANCD2, Exonuclease, MyD88, SMC1, DNA, Polymerase, delta, IRAK, BLM1, (POLD1, POLD2, POLD3, NIL, BRCA1, and, POLD4, genes, IKK, H2AX, encoding, subunits), NFKβ, ATR, Topoisomerase, 1, IκβO, RPA, Topoisomerase, 2, IAP, ATRIP, RNAseHl, Caspase, 3, RAD9, Ligase, 1, Caspase, 6, RAD1, DNA, polymerase, 1, Caspase, 7, HUS, DNA, polymerase, 3, Caspase, 8, RAD17, Primase, Caspase, 10, RFC, Helicase, HDAC1, CHK1, Single strand, binding, HDAC2, TLK1, proteins, Cytochrome, C, CDC25, Bxl-xL, STAT3, STAT5, DFF45, Vcl-2, ENDO-G, PI3K, Akt, Calpain, Bad, Bax, Ubiquitin-mediated proteolysis, Hypoxia, Cell Proliferation, HIF-loc, MAPK, E1, HERC1, TRAF6, HIF-Iβ, MAPKK, E2, UBE2Q, MEKK1, Refl, MAPKKK, E3, UBE2R, COP!, HSP90, c-Met, UBLE1A, UBE2S, PIFH2, VEGF, HGF, UBLE1B, UBE2Q, cIAP, PAS, ER, S1/2, UBLEIC, UBE2W, PIAS, ARNT, ATK, UBE2A, UBE2Z, SYVN, VHL, PKCs, UBE2B, AFC, LLC, N, NHLRC1, HLF, Paxilin, UBE2C, UBE1, AIRE, EPF, FAK, UBE2A, E6AP, MGRN1, VDU2, Adducin, UBE2E, UBE3B, BRCA1, SUMORESUME, PYK1, UBE2F, Smurf, FANCL, SENP1, RB, UBE2G1, Itch, MIDI, Calcineurin, A, RBI, UBE2G2, HERC2, Cdc20, RACK1, Raf-1, UBE2I, HERC3, Cdhl, PTB, A-Raf, UBE2J1, HERC4, Apcl, Hur, B-raf, UBE2J2, UBE4A, Apc2, PHD2, MEK1/2, UBE2L3, UBE4B, Apc3, SSAT2, ERK1/2, UBE2L6, CHIP, Apc4, SSAT1, Ets, UBE2M, CYC4, Apc5, GSK3, Elkl, UBE2N, PPR19, Apc6, CBP, SAP1, UBE20, UIP5, Apc7, FOX04, cPLA2, WWPI, Mdm2, Apc8, F1H-1, WWP2, Parkin, Apc9, TRIP, 12, Trim32, Ape, 10, NEED4, Trim37, Ape, 11, ARF-BP1, SIAH-1, Ape, 12, EDD1, PML, Cell, survival, Cell, cycle, arrest, SMADI, P21, SMAD5, BAX, SAMD8, MDR, LEF1, DRAIL, IGFBP3, TCF3, GADD45, TCF4, P300, HAT1, PI3, Akt, GF1, or any combinations thereof.

In some embodiments, genes associated with angiogenesis are modulated, enhanced or decreased in activity by administering a DNAPK inhibitor and a genomic editing system to a cell(s). Exemplary genes and genetic pathways associated with angiogenesis, and angiogenesis-related conditions include VEGF, VEGFR2, SHC, E2F7, VEGFB, VEGFR3, PI3, VEGFC, Nrp 1, PIP3, EGFDIP3, DAG, GRB2, SOS, Akt, PB, PKC, Ras, RAF-I, DAG, eNOS, NO, ERK1, ER2, cPLA2, ME1, MEK2, or any combinations thereof.

In some embodiments, genetic pathways and/or genes associated with mitochondrial function are modulated, enhanced or decreased in activity by administering a DNAPK inhibitor and a genomic editing system to a cell(s). Exemplary genes and genetic pathways associated with mitochondrial function include Malate dehydrogenase Aminotransferase, Hydratase, Deacylase, Dehydrogenase, Carboxylase, Mutase, Fatty acid oxidation Leucine Oxidation Isoleucine disorders (enzyme Pathway oxidation pathway deficiencies) Aminotransferase Aminotransferase, OCTN2 Branched chain Branched chain, FATP1-6 aminotransferase 2, aminotransferase 2, CPT-1 mitochondrial mitochondrial, CACT Isobutytyl-CoA 2-methylbutytyl-CoA, CPT-II dehydrogenase Dehydrogenase, SCAD (Branched Chain (Branched Chain, MCAD Keto Acid Keto Acid, VLCAD Dehydrogase Dehydrogenase, ETF-DH Complex) Complex), Alpha-ETF Hydratase Hydratase, Beta-ETF HMG-CoA lyase 2-methyl-3-OH-SCHAD butyryl-CoA, LCHAD dehydrogenase, MTP 3-Oxothiolase, LKAT, DECR 1, HMGCS2, HMGCL, or any combinations thereof.

In some embodiments, genetic pathways and/or genes associated with DNA damage or genomic instability are modulated, enhanced or decreased in activity. Exemplary genes and genetic pathways associated with pathways and/or genes relating to DNA Damage and genomic instability include 53BP1, BLM, MBD2, DNA, ligase, 4, MDC1, H2AX, XLF, SMC1, 53BP1, Rad50, P53, P53, Artemis, Rad27, TdT, APE1, PMS2, APE2, UvrA, RecA, MLH1, NEIL1, UvrB, SSB, MSH6, NEIL2, UvrC, Mrell, MSH2, NEIL3, XPC, Rad50, RFC, XRCC1, Rad23B, Nbsl, PCNA, PNKP, CEN2, CtIP, MSH3, Tdpl, DDB1, RPA, MutS, APTX, XPE, Rad51, MutL, DNA, polymerase β CSA, Rad52, DNA polymerase β, CSB, Rad54, Topoisomerase, 1, DNA, TFT1H, BRCA1, Topoisomerase, 2, PCNA, XPB, BRCA2, RNAseHl, FEN1, XPD, Exol, Ligase 1, RFC, XPA, BLM, DNA, polymerase, 1, PAR, 1, RPA, ToplIla, DNA, Ligl, XPG, GEN1, Primase, Lig3, ERCC1 Yenl Helicase, UNG, XPF, Slxl, SSBs, MUTY DNA polymerase Δ, Elx4, SMUG DNA polymerase s, Mus8, MBD4, Emel, Dssl, ASH1L, SETD4, DQT1L, SETD5, EHMT1, SETD6, EHMT2, SETD7, EZH1, SETD8, EZH2, SETD9, MLL, SETDB1, MLL2, SETDB2, MLL3, SETMAR, MLL4, SMYD, 1, MLL5, SMYD2, NSD, 1, SMYD3, PRDM2, SMYD4, SET, SMYD5, SETBP1, SUV39H1, SETD 1A, SUV39H2, SETD 1B, SUV420H1, SETD2, SUV420 H2, SETD3 or any combinations thereof.

In some embodiments, genes encoding for mammalian transcription factors are modulated, enhanced, decreased or provided to a cell. Exemplary human transcription factors include AFF4, AFF3, AFF2, AFF1, AR, TFAP2B, TFAP2D, TFAP2C, TFAP2E, TFAP2A, JARID2, KDM5D, ARID4A, ARID4B, KDM5A, ARID3A, KDM5B, KDM5C, ARID5B, ARID3B, ARID2, ARID5A, ARID3C, ARID1A, ARID1B, HIF1A, NPAS1, NPAS3, NPAS4, MLXIPL, ARNTL2, MXD1, AHRR, TFE3, HES2, MNT, TCF3, SREBF1, TFAP4, TCFL5, LYL1, USF2, TFEC, AHR, MLX, MYF6, MYF5, SIM1, TFEB, HAND1, HES1, ID2, MYCL1, ID3, TCF21, MXI1, SOHLH2, MYOG, TWIST1, NEUROG3, BHLHE41, NEUROD4, MXD4, BHLHE23, TCF15, MAX, ID1, MYOD1, ARNTL, BHLHE40, MYCN, CLOCK, HEY2, MYC, ASCL1, TCF12, ARNT, HES6, FERD3L, MSGN1, USF1, TAL1, NEROD1, TCF23, HEYL, HAND2, NEUROD6, HEY1, SOHLH1, MESP1, PTF1A, ATOH8, NPAS2, NEUROD2, NHLH1, ID4, ATOH1, ARNT2, HES3, MLXIP, ASCL3, KIAA2018, OLIG3, NHLH2, NEUROG2, MSC, HEST, ATOH7, BHLHA15, BHLHE22, NEUROG1, FIGLA, ASCL2, OLIG1, TAL2, MITF, SCXB, HELT, ASCL4, MESP2, HES4, SCXA, TCF4, HES5, SREBF2, BHLHA9, OLIG2, MXD3, TWIST2, LOC388553, C13orf38-SOHLH2, CEBPE, XBP1, BATF3, CREB5, CEB PG, ATF3, ATF7, CEBPB, CEBPD, CEB PA, CBFB, CAMTA2, CAMTAI, EBF4, EBF3, EBF1, EBF2, NR2F6, NR2F1, NR2F2, GRHL2, TFCP2L1, GRHL1, TFCP2, UBP1, GRHL3, YBX2, CSDE1, CSDA, YBX1, LIN28A, CARHSP1, CSDC2, LIN28B, NHX, NFIC, NFIB, NBA, CUX2, ONECUT2, CUX1, ONECUT1, SATB1, ONECUT3, SATB2, DMRT3, DMRT1, DMRTC2, DMRTA2, DMRTB1, DMRT2, DMRTA1, E2F2, E2F1, E2F3, TFDP2, E2F8, E2F5, E2F7, E2F6, TFDP3, TFDP1, E2F4, NR1H3, NR1H2, ETV1, ETV7, SPI1, ELF4, ETV2, ERF, ELF2, ELK3, ETV3, ELF1, SPDEF, ELK1, ETS1, EHF, ELF5, ETV6, SPIB, FLI1, GABPA, ERG, ETS2, ELK4, ELF3, FEV, SPIC, ETV4, ETV5, FOXN3, FOXCI, FOXJ2, FOXF1, FOXN1, FOXM1, FOXP1, FOXO3, FOXA2, FOXP2, FOXJ1, FOXP4, FOXF2, FOXN4, FOXK2, FOXO1, FOXH1, FOXQ1, FOXK1, FOXI1, FOXD4, FOXA3, FOXN2, FOXB1, FOXG1, FOXR1, FOXL1, FOXC2, FOXE1, FOXS1, FOXL2, FOXO4, FOXD4L1, FOXD4L4, FOXD2, *FOXI2*, FOXE3, FOXD3, FOXD4L3, FOXR2, FOXJ3, FOXO6, FOXB2, FOXD4L5, FOXD4L6, FOXD4L2, KIAA0415, FOXA1, FOXP3, GCM2, GCM1, NR3C1, GTF2IRD1, GTF2I, GTF2IRD2B, GTF2IRD2, SOX8, SOX30, PMS1, CIC, TCF7, TOX4, SOX10, HMGXB4, HBP1, TFAM, UBTF, WHSCI, SOX6, HMGXB3, BBX, TOX2, SOX4, SOX21, SOX9, SOX15, SOX5, SOX3, LEF1, HMG20A, SOX13, TCF7L2, SSRP1, TCF7L1, SOX17, SOX14, PINX1, SOX7, SOX11, SOX12, SOX2, SOX1, SRY, SOX18, UBTFL1, UBTFL2, TOX, HMGB1, HMGB2, PBRM1, TOX3, SMARCE1, HMG20B, HMGB3, HMGA2, HMGA1, ARX, HOXA11, MEOX1, DLX6, ISL1, HOXC8, BARX2, ALX4, GSC2, DLX3, PITX1, HOXA9, HOXAIO, LHX5, LASS4, ZFHX4, SIX4, VSX1, ADNP, RHOXF1, MEIS3, PBX4, DLX5, HOXA1, HOXA2, HOXA3, HOXA5, HOXA6, HOXA13, EVX1, NOBOX, MEOX2, LHX2, LHX6, LHX3, TLX1, PITX3, HOXB6, HNF1B, DLX4, SEBOX, VTN, PHOX2B, NKX3-2, DBX1, NANOG, IRX4, CDX1, TLX2, DLX2, VAX2, PRRX1, TGIF2, VSX2, NKX2-3, HOXB8, HOXB5, HOXB7, HOXB3, HOXB1, MSX2, LHX4, HOXA7, HOXC13, HOXC11, HOXC12, ESX1, BARHL1, NKX2-4, NKX2-2, SIX1, HOXD1, HOXD3, HOXD9, H1XD10, HOXD11, HOXD13, MNX1, CDX4, BARX1, RHOXF2, LHX1, GSC, MEIS2, RAX, EMX1, NKX2-8, NKX2-1, HLX, LMX1B, SIX3, LBX1, PDX1, LASS5, ZFHX3, BARHL2, LHX9, LASS2, MEIS1, DLX1, HMBOX1, ZEB1, VAX1, NKX6-2, VENTX, HHEX, TGIF2LX, LASS3, ALX3, HOXB13, IRX6, ISL2, PKNOX1, LHX8, LMX1A, EN1, MSX1, NKX6-1, HESX1, PITX2, TLX3, EN2, UNCX, GBX1, NKX6-3, ZHX1, HDX, PHOX2A, PKNOX2, CDX2, DRGX, NKX3-1, PBX3, PRRX2, GBX2, SHOX2, GSX1, HOXD4, HOXD12, EMX2, IRX1, IRX2, SIX2, HOXB9, HOPX, OTP, LASS6, HOXC5, HOXB2, RAX2, EVX2, ZHX3, PROP1, ISX, HOXD8, TGIF2LY, IRX5, SIX5, TGIF1, IRX3, ZHX2, LBX2, NKX2-6, ALX1, GSX2, HOXC9, HOXC10, HOXB4, NKX2-5, SIX6, MIXL1, DBX2, PBX1, SHOX, ARGFX, HMX3, HMX2, BSX, HOXA4, DMBX1, HOXC6, HOXC4, RHOXF2B, PBX2, DUXA, DPRX, LEUTX, NOTO, HOMEZ, HMX1, DUX4L5, DUX4L2, DUX4L3, DUX4L6, NKX1-1, HNF1A, HSF4, HSFY2, HSFX1, HSFX2, HSFY1, HSF1, LCORL, LCOR, IRF6, IRF1, IRF3, IRF5, IRF4, IRF8, IRF2, IRF7, IRF9, MBD3, BAZ2B, MBD4, SETDB2, MBD1, MECP2, SETDB1, MBD2, BAZ2A, SMAD7, SMAD5, SMAD9, SMAD6, SMAD4, SMAD3, SMAD1, SMAD2, ZZZ3, RCOR1, CDC5L, MYBL2, DNAJC2, TADA2A, RCOR3, MYB, TERF2, DMTF1, DNAJC1, NCOR1, TERFI, MIER3, MYSM1, SNAPC4, RCOR2, TADA2B, MYBL1, TERF1P2, NCOR2, CCDC79, SMARCC1, SMARCC2, TTF1, C11orf9, NFYA, NFYC, NFYB, NRF1, NR4A3, NR4A1, NR4A2, ESRI, NR0B2, NR0B1, PREB, EAF2, SPZ1, TP63, TP73, TP53, PAX6, PAX7, PAX2, PAX4, PAX8, PAX1, PAX3, PAX5, PAX9, SUB1, POU2F2, POU1F1, POU4F3, POU6F2, POU2F3, POU2F1, POU4F2, POU4F1, POU6F1, POU3F2, POU3F1, POU3F4, POU3F3, POU5F1, POU5F1B, PPARD, PPARG, PPARA, PGR, PROX1, PROX2, NR2E1, NR5A2, NR2C1, NR5A1, NR6A1, ESRRA, NR2C2, RFX3, RFX2, RFX4, RFX1, RFX5, RFX7, RFX6, RFX8, NFATC3, NFKB2, NFATC4, NFATC2, NFAT5, RELB, NFKB1, NFATC1, REL, RELA, RORA, RORC, NR1D2, RORB, RUNX3, RUNX1, SP1OO, SP140, GMEB2, SP1IO, AIRE, GMEB1, DEAF1, SP140L, LOC729991-MEF2B, MEF2A, SRF, MEF2D, MEF2B, STAT1, STAT5A, STAT4, STAT6, STAT3, STAT2, STAT5B, TBX21, TBX5, TBX15, TBX18, TBX2, TBX4, TBX22, TBX3, TBR1, TBX19, TBX6, EOMES, T, TBX20, TBX10, MGA, TBX1, TEAD3, TEAD2, TEAD1, TEAD4, CREBL2, NFE2L3, CREB3L3, FOSL2, NFE2L1, CREM, DBP, CREB3, HLF, BACH2, ATF2, NFE2L2, ATF6, CREB1, ATF1, NFE2, FOSB, ATF4, NRL, JUND, JDP2, CREB3L4, BATF, BACH1, CREB3L1, NFIL3, TEF, BATF2, ATF5, FOS, JUNB, DDIT3, FOSL1, JUN, MAF, CREB3L2, MAFA, MAFF, MAFG, MAFK, MAFB, ATF6B, CRX, OTX1, OTX2, THAP3, THAP10, THAP1, PRKRIR, THAP8, THAP9, THAP11, THAP2, THAP6, THAP4, THAP5, THAP7, NR1H4, NR2E3, RARB, HNF4A, VDR, ESRRB, THRA, NR1D1, RARA, ESR2, NR1I3, NR1I2, THRB, NR3C2, HNF4G, RARG, RXRA, ESRRG, RXRB, TSC22D1, TSC22D3, TSC22D4, TSC22D2, TULP3, TULP2, TULP1, TULP4, TUB, ZBTB33, ZBTB32, ZBTB11, MYNN, ZBTB25, PATZ1, ZBTB16, ZBTB24, BCL6, ZBTB47, ZBTB17, ZBTB45, GZF1, ZBTB1, ZBTB46, ZBTB8A, ZBTB7B, BCL6B, ZBTB49, ZBTB43, HIC2, ZBTB26, ZNF131, ZNF295, ZBTB4, ZBTB34, ZBTB38, HIC1, ZBTB41, ZBTB7A, ZNF238, ZBTB42, ZBTB2, ZBTB20, ZBTB40, ZBTB7C, ZBTB37, ZBTB3, ZBTB6, ZBTB44, ZFP161, ZBTB12, ZBTB48, ZBTB10, ZBED4, ZBED3, ZBED2, C11orf95, ZBED1, IKZF5, ZNF821, ZNF451, ZNF195, ZFX, ZNF263, ZNF200, HIVEP2, WIZ, ZNF582, SNAI2, ZFP64, IKZF2, ZIC2, ZNF800, PRDM1, PRDM6, ZFP112, ZNF275, ZNF76, ZFAT, KLF6, ZFY, ZXDC, GLI2, ZNF532, ZNF37A, ZNF5IO, ZNF506, ZNF324, ZNF671, ZNF416, ZNF586, ZNF446, ZNF8, ZNF264, REST, MECOM, ZNF213, ZNF343, ZNF302, ZNF268, ZNF10, HIVEP1, ZNF184, MZF1, SALL4, ZNF516, KLF8, KLF5, ZNF629, ZNF423, CTCF, ZNF500, ZNF174, SALL1, MAZ, ZNF419, OVOL3, ZNF175, ZNF14, ZNF574, ZNF85, SP4, ZKSCAN1, GLI3, GLIS3, KLF3, PRDM4, GLU, PRDM13, ZNF142, PRDM2, ZNF684, ZNF541, KLF7, PLAGL1, ZNF430, KLF12, KLF9, ZNF410, BCL11A, EGR1, ZFP3O, TSHZ3, ZNF549, ZSCAN18, ZNF211, ZNF639, ZSCAN20, GTF3A, ZNF205, ZNF644, EGR2, IKZF4, CTCFL, ZNF831, SNAIl, ZNF576, ZNF45, TRERF1, ZNF391, RREB1, ZNF133, OVOL2, ZNF436, PLAGL2, GLIS2, ZNF384, ZNF484, HIVEP3, BCL11B, KLF2, ZNF780B, FEZF1, KLF16, ZSCAN1O, ZNF557, ZNF337, PRDM12, ZNF317, ZNF426, ZNF331, ZNF236, ZNF341, ZNF227, ZNF141, ZNF304, ZSCAN5A, ZNF132, ZNF20, EGR4, ZNF670, VEZF1, KLF4, ZFP37, ZNF189, ZNF193, ZNF280D, PRDM5, ZNF740, ZIC5, ZSCAN29, ZNF710, ZNF434, ZNF287, ZIM3, PRDM15, ZFP14, ZNF787, ZNF473, ZNF614, PRDM16, ZNF697, ZNF687, OSR1, ZNF514, ZNF660, ZNF300, RBAK, ZNF92, ZNF157, ZNF182, ZNF41, ZNF711, PRDM14, ZNF7, ZNF214, ZNF215, SALL3, ZNF827, ZNF547, ZNF773, ZNF776, ZNF256, ZSCAN1, ZNF837, PRDM8, ZNF117, ZIC1, FEZF2, ZNF599, ZNF18, KLF10, ZKSCAN2, ZNF689, ZIC3, ZNF19, ZSCAN12, ZNF276, ZNF283, ZNF221, ZNF225, ZNF230, ZNF222, ZNF234, ZNF233, ZNF235, ZNF362, ZNF208, ZNF714, ZNF394, ZNF333, ZNF382, IKZF3, ZNF577, ZNF653, ZNF75A, GFI1, ZNF281, ZNF496, ZNF2, ZNF513, ZNF148, KLF15, ZNF691, ZNF589, PRDM9, ZNF12, SP8, OSR2, ZNF367, ZNF22, GFI1B, ZNF219, SALL2, ZNF319, ZNF202, ZNF143, ZNF3, ZSCAN21, ZNF606, SP2, ZNF91, ZNF23, ZNF226, ZNF229, ZNF180, ZNF668, ZNF646, ZNF641, ZNF610, ZNF528, ZNF701, ZNF526, ZNF146, ZNF444, ZNF83, ZNF558, ZNF232, E4F1, ZNF597, INSM2, ZNF30, ZNF507, ZNF354A, ZEB2, ZNF32, KLF13, ZFPM2, ZNF764, ZNF768, ZNF35, ZNF778, ZNF212, ZNF282, PRDM10, SP7, SCRT1, ZNF16, ZNF296, ZNF160, ZNF415, ZNF672, ZNF692, ZNF439, ZNF440, ZNF581, ZNF524, ZNF562, ZNF561, ZNF584, ZNF274, ZIK1, ZNF540, ZNF570, KLF17, ZNF217, ZNF57, ZNF556, ZNF554, KLF11, HINFP, ZNF24, ZNF596, OVOL1, SP3, ZNF621, ZNF680, BNC2, ZNF483, ZNF449, INSMI, ZNF417, ZNF791, ZNF80, GLIS1, ZNF497, KLF14, ZNF266, ZIC4, ZNF408, ZNF519, ZNF25, ZNF77, ZNF169, ZNF613, ZNF683, ZNF135, ZSCAN2, ZNF575, ZNF491, ZNF620, ZNF619, ZNF354C, ZNF114, ZNF366, ZNF454, ZNF543, ZNF354B, ZNF223, ZNF713, ZNF852, ZNF552, ZFP42, ZNF664, EGR3, ZFPM1, ZNF784, ZNF648, FIZ1, ZNF771, TSHZ1, ZNF48, ZNF816, ZNF571, ZSCAN4, ZNF594, ZFP3, ZNF443, ZNF792, ZNF572, ZNF707, ZNF746, ZNF322A, ZNF467, ZNF678, ZFP41, HKR1, PLAG1, ZNF329, ZNF101, ZNF716, ZNF708, ZSCAN22, ZNF662, ZNF320, ZNF623, ZNF530, ZNF285, ZFP1, WT1, ZFP90, ZNF479, ZNF445, ZNF74, SP1, SNAI3, ZNF696, IKZF1, ZNF267, ZNF566, ZNF224, ZNF529, ZNF284, ZNF749, ZNF17, ZNF555, ZNF75D, ZNF501, ZNF197, ZNF396, ZFP91, ZNF732, ZNF397, ZSCAN30, ZNF546, ZNF286A, ZKSCAN4, ZNF70, ZNF643, ZNF642, ZSCAN23, ZNF490, ZNF626, ZNF793, ZNF383, ZNF669, ZNF559, ZNF177, ZNF548, MTF1, ZNF322B, ZNF563, ZNF292, ZNF567, SP6, ZNF573, ZNF527, ZNF33A, ZNF600, ZKSCAN3, ZNF676, ZNF699, ZNF250, ZNF79, ZNF681, ZNF766, ZNF107, ZNF471, ZNF836, ZNF493, ZNF167, ZNF565, ZNF34, ZNF781, ZNF140, ZNF774, ZNF658, ZNF765, ZNF124, ZNF569, ZNF777, ZNF775, ZNF799, ZNF782, ZNF846, ZNF136, ZKSCAN5, ZNF502, ZFP62, ZNF33B, ZNF512B, ZNF431, ZNF418, ZNF700, ZNF239, ZSCAN16, ZFP28, ZNF705A, ZNF585A, ZNF138, ZNF429, ZNF470, ZNF100, ZNF398, ZNF498, ZNF441, ZNF420, ZNF763, ZNF679, ZNF682, ZNF772, ZNF257, ZNF785, ZSCAN5B, ZNF165, ZNF655, ZNF98, ZNF786, ZNF517, ZNF675, ZNF860, ZNF628, ZNF665, ZNF624, ZNF841, ZNF615, ZNF350, ZNF432, ZNF433, ZNF460, ZNF81, ZNF780A, ZNF461, ZNF181, LOC100287841, ZNF44, ZNF790, ZNF677, ZNF823, ZNF311, ZNF347, ZNF71, ZNF121, ZNF335, ZNF560, ZNF273, ZNF84, ZNF667, ZNF649, ZNF248, ZNF544, ZNF770, ZNF737, ZNF251, ZNF607, ZNF334, ZXDA, ZNF485, ZIM2, PEG3, ZNF192, ZNF442, ZNF813, ZNF26, ZNF69, ZNF583, ZNF568, ZXDB, ZNF480, ZNF587, ZNF808, ZNF43, ZNF28, ZNF627, ZNF789, ZNF536, ZNF534, ZNF652, ZNF521, ZNF358, ZFP2, SP5, ZNF814, ZNF551, ZNF805, ZSCAN5C, ZNF468, ZNF616, ZFP57, ZNF155, ZNF783, ZNF425, ZNF580, ZNF611, ZNF254, ZNF625, ZNF134, ZNF845, ZNF99, ZNF253, ZNF90, ZNF93, ZNF486, REPIN1, LOC100131539, ZNF705D, LOC100132396, ZNF705G, SCRT2, ZNF407, SP9, ZNF579, ZNF880, ZNF630, ZNF844, ZNF469, ZNF717, ZNF865, ZNF492, ZNF688, YY2, ZNF878, ZNF879, ZNF736, ZNF323, ZNF709, ZNF512, ZNF585B, ZNF154, ZNF324B, ZNF564, ZFP82, GLI4, ZNF674, ZNF345, ZNF550, KLF1, YY1, MYST2, ST18, L3MBTL4, MYT1L, MYT1, L3MBTL1, MTA3, GATA1, TRPS1, GATA3, GATA5, GATA4, GATA6, GATAD2B, GATAD1, GATA2, MTA1, ZGLP1, MTA2, RERE, C16orf5, LITAF, PIAS1, PIAS2, PIAS4, ZMIZ1, ZMIZ2, PIAS3, RNF138, NFX1, NFXL1, or any combinations thereof.

In some embodiments, cells are manipulated (e.g., converted or differentiated) from one cell type to another. In some embodiments, a pancreatic cell is manipulated into a beta islet cell. In some embodiments, a fibroblast is manipulated into an iPS cell. In some embodiments, a preadipocyte is manipulated into a brown fat cell. Other exemplary cells include, e.g., muscle cells, neural cells, leukocytes, and lymphocytes.

In some embodiments, the cell is a diseased or mutant-bearing cell. Such cells can be manipulated to treat the disease, e.g., to correct a mutation, or to alter the phenotype of the cell, e.g., to inhibit the growth of a cancer cell. For example, a cell is associated with one or more diseases or conditions described herein.

In some embodiments, the manipulated cell is a normal cell.

In some embodiments, the manipulated cell is a stem cell or progenitor cell (e.g., iPS, embryonic, hematopoietic, adipose, germline, lung, or neural stem or progenitor cells). In some embodiments, the manipulated cell can be a cell from any of the three germ layers (i.e. mesodermal, endodermal or ectodermal. In some embodiments, the manipulated cell can be from an extraembryonic tissue, for example, from the placenta.

In some embodiments, the cell being manipulated is selected from fibroblasts, monocytic-precursors, B cells, exocrine cells, pancreatic progenitors, endocrine progenitors, hepatoblasts, myoblasts, or preadipocytes. In some embodiments, the cell is manipulated (e.g., converted or differentiated) into muscle cells, erythroid-megakaryocytic cells, eosinophils, iPS cells, macrophages, T cells, islet beta-cells, neurons, cardiomyocytes, blood cells, endocrine progenitors, exocrine progenitors, ductal cells, acinar cells, alpha cells, beta cells, delta cells, PP cells, hepatocytes, cholangiocytes, angioblast, mesoangioblast or brown adipocytes.

In some embodiments, the cell is a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

In some embodiments, the cell is a precursor cell, a pluripotent cell, a totipotent cell, an adult stem cell, an inner cell mass cell, an embryonic stem cell, or an iPS cell.

In some embodiments, the manipulated cell is a cancer cell. In some embodiments, the cancer cell can be a lung cancer cell, a breast cancer cell, a skin cancer cell, a brain cancer cell, a pancreatic cancer cell, a hematopoietic cancer cell, a liver cancer cell, a kidney cancer cell, an ovarian cancer cell, a prostate cancer cell, a skin cancer cell. In some embodiments, the cell is a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

Administration of DNAPK Inhibitors and Gene-Editing System to a Cell(s)

Administering to a cell(s) a genome editing system and a DNAPK inhibitor can be performed by any method known in the art. The administering can be in vitro, ex vivo or in vivo. The administering to a cell(s) a genome editing system and a DNAPK inhibitor can occur simultaneously or sequentially. In some embodiments, the administering results in the DNAPK inhibitor and the genome editing system components to enter the cell membrane. In some embodiments, the administering results in the DNAPK inhibitor and the genome editing system components to enter into the cell nucleus. In some embodiments, the administering includes incubating the cell in the presence of the DNAPK inhibitor and genome editing system.

The gene editing system can be administered to a cell(s) by any method known in the art. For example, any nucleic acid or protein delivery methods known in the art can be used. The gene editing system is administered (e.g., delivered) to a cell by way of a nucleic acid encoding the gene editing system components. The gene editing system can be administered to a cell by either viral vectors or non-viral vectors. In some embodiments, viral vectors are used. The viral vectors can be retroviral (e.g. murine leukemia, HIV, or lentiviral) or DNA viruses (e.g. adenovirus, herpes simplex, and adeno-associated). In some embodiments, transfection methods (e.g. non-viral delivery methods) are used to introduce the genome editing system into a cell. Transfection methods include contacting the cell with DEAE-Dextran, calcium phosphate, liposomes or electroporation of a plasmid into a cell. Additional methods of non-viral delivery include electroporation, lipofection, microinjection, biolistics, virosomes, liposomes, immuno liposomes, polycation or lipid: nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In some embodiments, one or more nucleic acids are delivered as mRNA. In some embodiments, capped mRNAs are used to increase translational efficiency and/or mRNA stability. In some embodiments, ARCA (anti-reverse cap analog) caps or variants thereof are used. See U.S. Pat. Nos. 7,074,596 and 8,153,773.

In embodiments, the endonuclease (e.g. Cas, Cpf1 and the like) and the gRNA, are transcribed from DNA.

In embodiments, the endonuclease (e.g. Cas, Cpf1 and the like) is transcribed from DNA and the gRNA is provided as RNA.

In embodiments, the endonuclease (e.g. Cas, Cp0f1 and the like) and the gRNA are provided as RNA.

In embodiments, the endonuclease (e.g. Cas, Cpf1 and the like) is provided as a protein and the gRNA is provided as DNA.

In embodiments, the endonuclease (e.g. Cas, Cpf1 and the like) is provided as protein and the gRNA is provided as RNA.

Additional nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995);

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) Nature Biotechnology 27(7):643) Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

In some embodiments, the transfection can be transient in which the transfected genome editing system containing plasmid enters the nucleus but does not become incorporated into the genome of the cell during replication. The transfection can be stable in which the transfected plasmid will become integrated into a genomic region of the cell.

In some embodiments in which transient expression is used, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94: 1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol Cell. Biol. 4:2072-2081 (1984); Hermonat & Muzyczka, PNAS 81: 6466-6470 (1984); and Samulski et al., J. Virol 63:03822-3828 (1989).

In some embodiments, the administering to a cell(s) of a DNAPK inhibitor is performed by culturing an isolated cell(s) in the presence of the DNAPK inhibitor and any suitable medium that allows for the DNAPK inhibitor to enter the cell membrane and/or the cell nucleus.

In some embodiments, the DNAPK inhibitors are administered to a cell (s) in vitro, in vivo or ex vivo. In some embodiment, the DNAPK inhibitor is contacted with a cell(s) for about 5 hours, 10 hours, 15 hours, 20 hours, 21 hours, 22 hours, 23 hours, 24 hours, 25 hours, 30 hours, 35 hours, 40 hours, 45 hours, 50 hours, 55 hours, 60 hours, 65 hours, 70 hours, 85 hours, 90 hours, 100 hours, 125 hours, 150 hours, 200 hours, or for any period of time in between. In some embodiments, the DNAPK inhibitor is contacted with a cell(s) for about 1.5 weeks, 2.0 weeks, 2.5 weeks, 3.0 weeks, 3.5 weeks, 4 weeks, or any period of time in between. The DNAPK inhibitor may be re-administered with cell culture medium changes. The DNAPK inhibitor can be contacted with the cell either before, during or after introduction of genome editing system components.

In some embodiments, the DNAPK inhibitor is administered to a cell(s) at a concentration of about 0.1 µM, 0.25 µM, 0.5 µM, 0.75 µM, 1.0 µM, 1.25 µM, 1.50 µM, 1.75 µM, 2.0 µM, 2.5 µM, 3.0 µM, 3.5 µM, 4.0 µM, 4.5 µM, 5.0 µM, 5.5 µM, 6.0 µM, 6.5 µM, 7.0 µM, 7.5 µM, 8.0 µM, 8.5 µM, 9.0 µM, 9.5 µM, 10 µM, 10.5 µM, 11.0 µM, 11.5 µM, 12 µM, or any concentrations in between. The DNAPK inhibitor concentration can be modified during the course of administration.

In some embodiments, the gene-editing components are delivered into a cell(s) by one or more vectors or in the form of RNA, mRNA or in the case of the endonuclease component as purified protein or mRNA (e.g. Cas9 protein). The one or more vectors can include viral vectors, plasmids or ssDNAs. Viral vectors can include retroviral, lentiviral, adenoviral, adeno-associated, and herpes simplex viral vectors, or any combinations thereof. In some embodiments, the gene-editing components are delivered via RNA or synthetic RNA.

In some embodiments, administration of the DNAPK inhibitors to a cell along with a gene-editing system results in increased amounts of homologous directed repair gene-editing outcome in comparison to a baseline condition in which the cell is not administered a DNAPK inhibitor. In some embodiments, administration of the DNAPK inhibitors to a cell(s) along with a gene-editing system results in suppression of indels (from NHEJ) either on-target or off-target. In some embodiments, administration of the DNAPK inhibitors to a cell(s) along with a gene-editing system results in increased or decreased expression of a gene of interest. Administration of the DNAPK inhibitors to a cell(s) along with a gene-editing system can result in the expression of a gene not endogenous to a cell. In some embodiments, administration of the DNAPK inhibitors to a cell(s) along with a gene-editing system results in the complete or partial removal, or a modification of a gene from a cell(s). In some embodiments, administration of the DNAPK inhibitors to a cell(s) along with gene-editing system result(s) in the complete or partial removal, or a modification of an intron and/or an exon in a cell(s). In some embodiments, administration of the DNAPK inhibitors to a cell(s) along with gene-editing system result(s) in the complete or partial removal, or a modification of a non-coding region in a cell(s). In some embodiments, administration of the DNAPK inhibitors to a cell along with gene-editing system result(s) in simultaneous or sequential, complete or partial removal, or a modification of a coding and/or non-coding genetic region in a cell(s). In some embodiments, administration of the DNAPK inhibitors to a cell(s) along with gene-editing system results in simultaneous or sequential, complete or partial removal, or a modification of a coding and/or non-coding genetic region in a cell(s), including extrachromosomal DNA or RNA. The Extrachromosomal DNA can be mitochondrial DNA, chloroplast DNA, extrachromosomal circular DNA, or viral extra chromosomal DNA.

In some embodiments, administration of DNAPK inhibitors to a cell along with genome editing system results in increased expression or decreased expression of a gene of interest. In some embodiments, the increase or decrease in expression of a gene of interest can be about or between, 2.5%, 5%, 10%, 20%, 30%, 40%, 50%, 60%, 70%, 80%, 90% in comparison to a baseline condition in which the cell is not administered a DNAPK inhibitor. In some embodiments, the increase or decrease of a gene of interest can be about or between, 0.5-fold, 1.0-fold, 1.5-fold, 2.0-fold, 2.5-fold, 3.0-fold, 3.5-fold, 4-fold, 4.5-fold, 5-fold or 10-fold in comparison to the baseline expression level in which the cell is not administered a DNAPK inhibitor.

In some embodiments, administration of DNAPK inhibitors to a cell along with a genome editing system results in an increase in genome editing. In some embodiments, the increase in genome editing can be about or between 2.5%, 5%, 10%, 20%, 30%, 40%, 50%, 60%, 70%, 80%, 90% in comparison to a baseline condition in which the cell is not administered a DNAPK inhibitor. In some embodiments, the increase in genome editing can be about or between 0.5-fold, 1.0-fold, 1.5-fold, 2.0-fold, 2.5-fold, 3.0-fold, 3.5-fold, 4-fold, 4.5-fold, 5-fold or 10-fold in comparison to the baseline expression level in which the cell is not administered a DNAPK inhibitor.

In some embodiments, administration of a DNAPK inhibitor and a gene editing system to a cell population results in greater cell survival in comparison to a baseline condition in which a cell population only administered a gene editing system and is not administered a DNAPK inhibitor. In some embodiments, the DNAPK inhibitor that results in greater cell survival is a compound of Structural Formula I, Structural Formula II, or Structural Formula II".

In some embodiments, the cell is synchronized at the S or G2 cell cycle phase, either before, after or during administration of the DNAPK inhibitor. In some embodiments, the cell is synchronized at the S or G2 cell cycle phase, either before, after or during introduction of the gene-editing components. Synchronization of the cell at the S or G2 cell cycle phase can be achieved by any method known in the art. As a non-limiting example, agents that can be used to synchronize a cell at the S or G2 cell cycle phase include aphidicolin, dyroxyurea, lovastatin, mimosine, nocodazole, thymidine, or any combinations thereof. (See, Lin et al. Elife. 2014 Dec. 15; 32014). In some embodiments, the agents for cell synchronization can be administered at any time during the gene-editing process.

In some embodiments, the DNAPK inhibitor and/or the genome editing system can be included in a container, pack, or dispenser together with instructions for use. In some embodiments, the DNAPK inhibitor agent and/or the genome editing system included in a container, pack or dispenser together with instructions for use is a kit.

In some embodiments, the DNAPK inhibitors and/or the genome editing system are included in a kit with instructions for use. The kit can contain any genome editing system, and/or DNAPK inhibitor and instructions for use. In some embodiments the DNAPK inhibitor is any of compounds represented by Structural Formula I, I', II, II', II", II''', III, III', or any combinations thereof. In some embodiments, the genome editing system is a selected from a meganuclease based system, a zinc finger nuclease (ZFN) based system, a Transcription Activator-Like Effector-based Nuclease (TALEN) system, a CRISPR-based system, or a NgAgo-based system. The genome editing system can be provided in the kit in any form, for example as a plasmid, vector, DNA, or RNA construct.

In some embodiments, the DNAPK inhibitor and/or a genome editing system is administered in vivo. The DNAPK inhibitor and the gene-editing system is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

For injectable use, suitable carriers include sterile aqueous solutions (where water soluble) or dispersions and sterile powders for the extemporaneous preparation of sterile injectable solutions or dispersion. For intravenous (IV) administration, suitable carriers include physiological saline, bacteriostatic water, Cremophor EL™ (BASF, Parsippany, N.J.) or phosphate buffered saline (PBS). In such injectable and IV administrations, the composition are sterile and fluid to the extent that easy syringeability exists. They are stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols such as manitol, sorbitol, sodium chloride are included in the composition. Prolonged absorption of the injectable compositions can be brought about by including in the composition an agent which delays absorption, for example, aluminum monostearate and gelatin.

Sterile injectable solutions can be prepared by incorporating the active agent in the required amount in an appropriate solvent with one or a combination of ingredients enumerated above, as required, followed by filtered sterilization. Generally, dispersions are prepared by incorporating the active agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the agents are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The agents can also be prepared in the form of suppositories (e.g., with conventional suppository bases such as cocoa butter and other glycerides) or retention enemas for rectal delivery.

In some embodiments, the agents are prepared with carriers that will protect the compound against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active agents can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the agent, which matrices are in the form of shaped articles, e.g., films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

In some embodiments, the formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the DNAPK inhibitor agent and/or the genome editing system are administered in combination therapy, i.e., combined with other agents, e.g., therapeutic agents, that are useful for treating pathological conditions or disorders, such as various forms of cancer and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

Genome Editing Screening Methods

Any method known in the art can be used to screen cells for genome-editing efficiency, including the efficiency of NHEJ and/or HDR. For example, screening methods can include PCR based amplification of targeted regions followed by sequencing or deep sequencing of the amplified regions to confirm genome editing. PCR genotyping permits the quantification and ranking of compounds in stimulating HDR. Other screening methods can include next-generation sequencing. See, for example Bell et al., "A high-throughput screening strategy for detecting CRISPR-Cas9 induced mutations using next-generation sequencing," BMC Genomics, 15:1002 (2014).

PCR primers can be engineered to selectively amplify both unmodified and modified genetic regions, resulting in amplicons of different lengths depending on the genetic modification status. The amplicons can then be resolved on a gel, and the HDR efficiency estimated by densitometry using a Bio-Imager. Alternatively, a new PCR technology, the rapid digital droplet PCR (DDPCR) can be used to simultaneously measure HDR and NHEJ events in genome-edited samples. See, for example, Miyaoka et al., "Systematic quantification of HDR and NHEJ reveals effectrs of locus, nuclease, and cell type on genome-editin," *Scientific Reports.* 6, 2016. Other methods that can be used for screening cells for genomic modifications including, Sanger sequencing, deep sequencing, and RT-PCR.

In some embodiments, a traffic light reporter (TLR) construct is used for screening cells. TLR screening includes a reporter cell that is engineered to express a fluorescent marker upon targeted genome editing. Following appropriate targeting, the fluorescent marker is expressed by the cell. Quantification of the appropriately targeted cells can be performed by any method known in the art, for example, flow-cytometric analysis. See, for example, Certo et al. 2011, "Tracking genome engineering outcome at individual DNA breakpoints," *Nature Methods,* 8, pages 671-676 (2011).

The relevant portions of all publications and patent documents cited herein are incorporated herein by reference as if each such publication or document is specifically and individually indicated to be incorporated herein by reference. Citation of publications and patent documents is not intended as an admission that any is pertinent prior art, nor does it constitute any admission as to the contents or date of the same. The present disclosure having now been described by way of written description, those of skill in the art will recognize that a variety of embodiments can be practiced and that the foregoing description and examples below are for purposes of illustration and not limitation of the claims that follow.

EXAMPLES

The following examples, including the experiments conducted and results achieved are provided for illustrative purposes only and are not to be construed as limiting upon the present disclosure.

Example 1: Materials and Methods

Traffic light reporter (TLR) assay: The HEK293-EGIP (Enhanced Green Fluorescent inhibited Protein) stable cell line was purchased from System Biosciences (SBI). The HEK293-EGIP cell line harbors a disrupted GPP coding sequence with a stop codon and a 53-bp genomic fragment from the AAVS1 locus. Cells were maintained in DMEM (Life Technologies, cat. no. 10313-039) with high glucose (Life Technologies, cat. no. 10313-039) supplemented with 10% heat-inactivated FBS (Fetal Bovine Serum, Expression Systems Inc.), Glutamax and Penicillin+Streptomycin and cultured at 37° C. and 5% $CO_2$.

Cell transfection and NHEJ inhibitor treatment: The HEK293-EGIP stable cells were transfected with the two-in-one gRNA/CRISPR-Cas9 dual plasmid vector, plasmid repair donor (both plasmids from System Biosciences). Transfection was carried out using the Amaxa nucleofector system (Lonza) following manufacturer's protocol. After 16 hours, cells were treated with Compound 1 and Scr7 (Excess Bioscience; no. M60082-2s) at various concentrations, including 1 µM, 2.5 µM, 5 µM and 10 µM of compound. The structure of Scr7 is shown as follows:

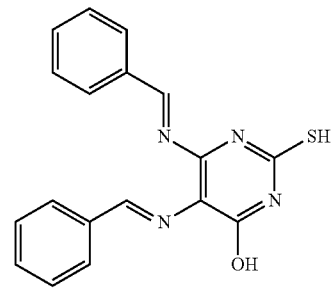 [SMILES: Oc1nc(S)nc(/N=C/c2ccccc2)c1/N=C/c1ccccc1]

The media was changed following an additional 24 hour incubation. FACS analysis was performed 5 days post transfection; cells were then collected for genomic DNA isolation and PCR genotyping.

Cell Sorting and Flow Cytometry: For flow cytometry analysis, HEK293 cells were trypsinized and resuspended in PBS/1% BSA FACS buffer and analyzed with a Fortessa flow cytometer (Becton Dickinson). A portion of cells were centrifuged and used for the isolation of genomic DNA.

Cell viability assay upon compound treatment: To assess potential toxicity of Scr7, cell viability was assessed after exposure to different concentrations of compounds. Cell viability of HEK293-EGIP was determined by CellTiter Glo (Promega) kit. The cells transfected with the plasmid donor were grown in the presence of compound (1 µM, 2.5 µM, 5 µM and 10 µM) for 24, 48 or 72 h, and subjected to the CellTiter Glo assay. Each experiment was repeated three independent times in triplicates. To maintain healthy cells capable of entering S/G2, which is necessary for HDR, cells were treated with compound at a concentration of 2.5 µM.

Genomic DNA isolation, PCR Genotyping, and Gel Quantification: Specially designed PCR primer pairs provided another means to assess HDR-mediated genome editing to obtain functional eGFP positive cells. The genotyping PCR primer pair is shown below, corresponding to SEQ ID NOs: 6 and 7. A 219 bp PCR product corresponds to unmodified cells and a 163 bp nucleotide corresponds to modification through HDR. Intensity of these bands on a >2.5% gel allows for estimation of HDR by densitometry using a Bio-Imager. The technique allows for the relative ranking of improvement of HDR by inhibitors. Intensities measured for each lane were normalized by calculating the ratios of PCR bands corresponding to 'insertions' divided by 'total' (inserted and unmodified). The fold-change was calculated by comparing the ratio of insertions with compound over that without compound.

Example 2: Assay for Monitoring HDR Efficiency

Assays were performed to ascertain HDR efficiency in HEK293-EGIP cells. To this end, a bicistronic construct was used that targets the human AAVS1 locus (FIG. 1A). The bicistronic vector system co-expresses human codon optimized Cas9 driven by the EF1 promoter as well as custom guide RNA (gRNA) consisting of a chimeric crRNA-tracrRNA transcript driven by the H1 promoter. The hspCas9 contains two nuclear localization signals (NLS) at the N-terminus and C-terminus to ensure efficient import of the hspCas9 protein into the nucleus. The hspCas9 open reading frame (ORF) is followed by a regulatory element called WPRE (Woodchuck virus post-transcriptional regulatory element) to boost gene expression and stabilize the mRNA transcript.

The engineered human cell line, EGIP HEK293 was used to monitor HDR efficiency using the bicistronic construct described above and in FIG. 1A. The EGIP HEK293 reporter cell line was purchased from SBI. The HEK293-EGIP cell line harbors a disrupted GFP coding sequence with a stop codon and a 53-bp genomic fragment from the AAVS1 locus. The stable line was generated by lentiviral infection of 293T cells with an EF1alpha promoter to drive the expression of eGFP followed by puromycin selection. The eGFP sequence was modified to insert a 56 nucleotide insert (uppercase) from the human AAVS1 safe harbor site. This sequence contains a stop codon (TAA in red) after amino acid T109 in the eGFP translated sequence. The guide sequences targeted are in bold letters. Upon transfection with the guide and donor, the AAVS1 site within the broken eGFP was cut and the donor construct provided a homologous sequence to repair the eGFP, by removing the stop codon and the AAVS1 insert. Edited cells which had undergone HDR donor repair will generate GFP positive cells. Accordingly, co-transfecting Cas9, gRNA targeting AAVS1 and a AAVS1/EGFP rescue donor restored the sequence by HDR to give GFP+ cells.

Figure 1B:
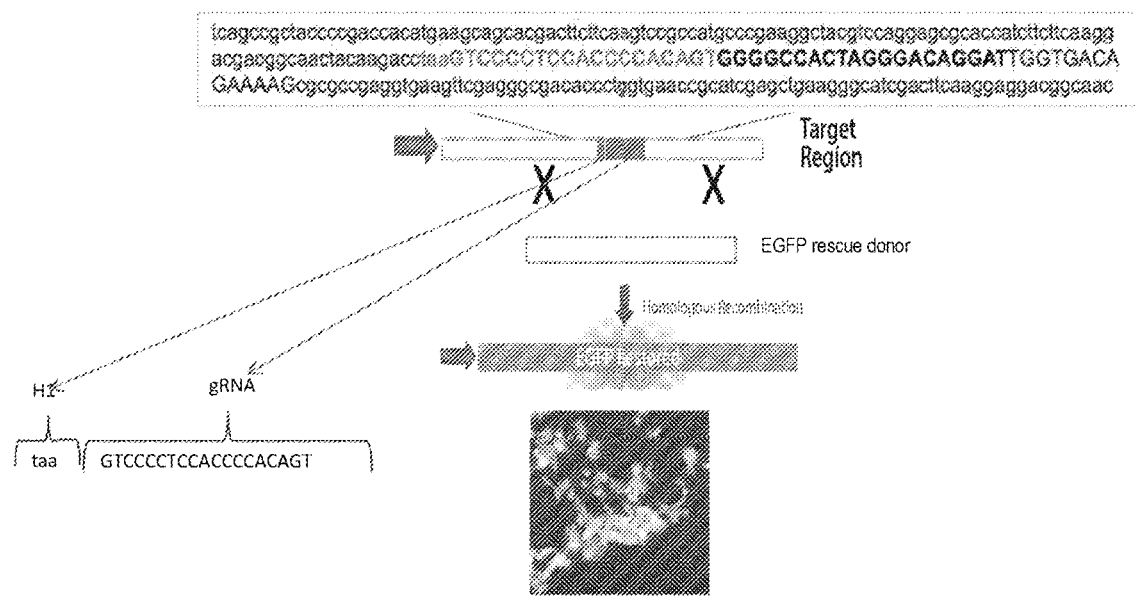

The population of GFP positive cells was directly proportional with the efficiency of the homology directed repair (FIG. 1B).

For these assays, two-in-one Cas9-sgRNAs and eGFP donor template vectors were introduced into the HEK293 EGIP cells by electroporation using the Amaxa nucleofector (Lonza) to drive the synthesis of Cas9-sgRNAs and the eGFP donor template. Compounds were added 16 h post transfection followed by media change 48 hours later. Cells were then allowed to propagate for an additional 72 hours before FACS analysis.

The HDR donor template sequence contained a 266 nucleotide 5' homology arm (in bold, black and underlined) and a 378 nucleotide 3' homology arm (in italics and underlined) (see SEQ ID NO: 1 below). Upon transfection with the guide RNA and donor template, the AAVS1 site within the broken eGFP was cut and the donor construct provided a homologous sequence to repair the eGFP, removing the stop codon and the AAVS1 insert.

The HDR template sequence used in the traffic light reporter assay is shown below (SEQ ID NO: 1):

(SEQ ID NO: 1)
TCGCGCGTTTCGGTGATGACGGTGAAAACCTCTGACACATGCAGCTCCCGG

AGACGGTCACAGCTTGTCTGTAAGCGGATGCCGGGAGCAGACAAGCCCGTC

AGGGCGCGTCAGCGGGTGTTGGCGGGTGTCGGGGCTGGCTTAACTATGCGG

CATCAGAGCAGATTGTACTGAGAGTGCACCATATGCGGTGTGAAATACCGC

ACAGATGCGTAAGGAGAAAATACCGCATCAGGCGCCATTCGCCATTCAGGC

TGCGCAACTGTTGGGAAGGGCGATCGGTGCGGGCCTCTTCGCTATTACGCC

AGCTGGCGAAAGGGGGATGTGCTGCAAGGCGATTAAGTTGGGTAACGCCAG

GGTTTTCCCAGTCACGACGTTGTAAAACGACGGCCAGTGAAACTAGTGCGA

CGTAAACGGCCACAAGTTCAGCGTGTCCGGCGAGGGCGAGGGCGATGCCAC

CTACGGCAAGCTGACCCTGAAGTTCATCTGCACCACCGGCAAGCTGCCCGT

GCCCTGGCCCACCCTCGTGACCACCCTGACCTACGGCGTGCAGTGCTTCAG

CCGCTACCCCGACCACATGAAGCAGCACGACTTCTTCAAGTCCGCCATGCC

CGAAGGCTACGTCCAGGAGCGCACCATCTTCTTCAAGGACGACGGCAACTA

CAAGACC_CGCGCCGAGGTGAAGTTCGAGGGCGACACCCTGGTGAACCGCAT_

_CGAGCTGAAGGGCATCGACTTCAAGGAGGACGGCAACATCCTGGGGCACAA_

_GCTGGAGTACAACTACAACAGCCACAACGTCTATATCATGGCCGACAAGCA_

_GAAGAACGGCATCAAGGTGAACTTCAAGATCCGCCACAACATCGAGGACGG_

_CAGCGTGCAGCTCGCCGACCACTACCAGCAGAACACCCCCATCGGCGACGG_

_CCCCGTGCTGCTGCCCGACAACCACTACCTGAGCACCCAGTCCGCCCTGAG_

_CAAAGACCCCAACGAGAAGCGCGATCACATGGTCCTGCTGGAGTTCGTGAC_

_CGCCGCCGGGATCACTCTCGGCATGGAC_GTCGACACCGGTGATATCAAGCT

TGGCGTAATCATGGTCATAGCTGTTTCCTGTGTGAAATTGTTATCCGCTCA

CAATTCCACACAACATACGAGCCGGAAGCATAAAGTGTAAAGCCTGGGGTG

CCTAATGAGTGAGCTAACTCACATTAATTGCGTTGCGCTCACTGCCCGCTT

TCCAGTCGGGAAACCTGTCGTGCCAGCTGCATTAATGAATCGGCCAACGCG

CGGGGAGAGGCGGTTTGCGTATTGGGCGCTCTTCCGCTTCCTCGCTCACTG

ACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGC

TGGCGTTTTTCCATAGGCTCCGCCCCCCTGACGAGCATCACAAAAATCGAC

GCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCATA

GCTCACGCTGTAGGTATCTCAGTTCGGTGTAGGTCGTTCGCTCCAAGCTGG

GCTGTGTGCACGAACCCCCCGTTCAGCCCGACCGCTGCGCCTTATCCGGTA

ACTATCGTCTTGAGTCCAACCCGGTAAGACACGACTTATCGCCACTGGCAG

CAGCCACTGGTAACAGGATTAGCAGAGCGAGGTATGTAGGCGGTGCTACAG

AGTTCTTGAAGTGGTGGCCTAACTACGGCTACACTAGAAGAACAGTATTTG

GTATCTGCGCTCTGCTGAAGCCAGTTACCTTCGGAAAAAGAGTTGGTAGCT

CTTGATCCGGCAAACAAACCACCGCTGGTAGCGGTGGTTTTTTTGTTTGCA

AGCAGCAGATTACGCGCAGAAAAAAAGGATCTCAAGAAGATCCTTTGATCT

TTTCTACGGGGTCTGACGCTCAGTGGAACGAAAACTCACGTTAAGGGATTT

TGGTCATGAGATTATCAAAAAGGATCTTCACCTAGATCCTTTTGATCCCCG

CCACGGTTGATGAGAGCTTTGTTGTAGGTGGACCAGTTGGTGATTTTGAAC

TTTTGCTTTGCCACGGAACGGTCTGCGTTGTCGGGAAGATGCGTGATCTGA

TCCTTCAACTCAGCAAAAGTTCGATTTATTCAACAAAGCCGCCGTCCCGTC

AAGTCAGCGTAATGCTCTGCCAGTGTTACAACCAATTAACCAATTCTGATT

-continued

```
AGAAAAACTCATCGAGCATCAAATGAAACTGCAATTTATTCATATCAGGAT

TATCAATACCATATTTTTGAAAAAGCCGTTTCTGTAATGAAGGAGAAAACT

CACCGAGGCAGTTCCATAGGATGGCAAGATCCTGGTATCGGTCTGCGATTC

CGACTCGTCCAACATCAATACAACCTATTAATTTCCCCTCGTCAAAAATAA

GGTTATCAAGTGAGAAATCACCATGAGTGACGACTGAATCCGGTGAGAATG

GCAAAGTTTATGCATTTCTTTCCAGACTTGTTCAACAGGCCAGCCATTAC

GCTCGTCATCAAAATCACTCGCATCAACCAAACCGTTATTCATTCGTGATT

GCGCCTGAGCGAGACGAAATACGCGATCGCTGTTAAAAGGACAATTACAAA

CAGGAATCGAATGCAACCGGCGCAGGAACACTGCCAGCGCATCAACAATAT

TTTCACCTGAATCAGGATATTCTTCTAATACCTGGAATGCTGTTTTTCCGG

GGATCGCAGTGGTGAGTAACCATGCATCATCAGGAGTACGGATAAAATGCT

TGATGGTCGGAAGAGGCATAAATTCCGTCAGCCAGTTTAGTCTGACCATCT

CATCTGTAACATCATTGGCAACGCTACCTTTGCCATGTTTCAGAAACAACT

CTGGCGCATCGGGCTTCCCATACAATCGATAGATTGTCGCACCTGATTGCC

CGACATTATCGCGAGCCCATTTATACCCATATAAATCAGCATCCATGTTGG

AATTTAATCGCGGCCTCGAGCAAGACGTTTCCCGTTGAATATGGCTCATAA

CACCCCTTGTATTACTGTTTATGTAAGCAGACAGTTTTATTGTTCATGATG

ATATATTTTTATCTTGTGCAATGTAACATCAGAGATTTTGAGACACAATTC

ATCGATGATGGTTGAGATGTGTATAAGAGACAGATTATTGAAGCATTTATC

AGGGTTATTGTCTCATGAGCGGATACATATTTGAATGTATTTAGAAAAATA

AACAAATAGGGGTTCCGCGCACATTTCCCCGAAAAGTGCCACCTGACGTCT

AAGAAACCATTATTATCATGACATTAACCTATAAAAATAGGCGTATCACGA

GGCCCTTTCGTC
```

The primer sites used for the assay described herein are shown below. These primer sites are located within the donor sequence. PCR reaction on the genomic template generated a 700 nucleotide product with NHEJ expected to produce fragments around 300 nucleotides and 400 nucleotides in length. Following HDR event the expected PCR product using the supplied donor template is 644 nucleotides. The primer sites used for the assay include the following sequences.

```
Guide RNA_1:
                                        (SEQ ID NO: 2)
GTCCCCTCCACCCCACAGTG Guide RNA_2:
                                        (SEQ ID NO: 3)
GGGGCCACTAGGGACAGGAT Forward Surveyor primer:
                                        (SEQ ID NO: 4)
GCGACGTAAACGGCCACAAG Reverse Surveyor primer:
                                        (SEQ ID NO: 5)
GTCCATGCCGAGAGTGATCC HDR primer_1:
                                        (SEQ ID NO: 6)
ACTTCTTCAAGTCCGCCATGCCC HDR primer_2:
                                        (SEQ ID NO: 7)
ATGTTGCCGTCCTCCTTGAAGTCG
```

Example 3: DNAPK Inhibitor Increases CRISPR-Genome Editing HDR Efficacy

HEK293-EGIP cells were nucleofected with the following constructs and cultured as described: dual expression gRNA-Cas9 only, dual expression gRNA-Cas9 with donor repair template, dual expression gRNA-Cas9 with donor template and culture of the cells with 2.5 µM Compound 1, and dual expression gRNA-Cas9 with donor repair template and culture of the cells with 2.5 µM of the putative ligase IV inhibitor Scr7. The cells were contacted with Compound for with Scr7 for 24 hours.

Figure 2A:
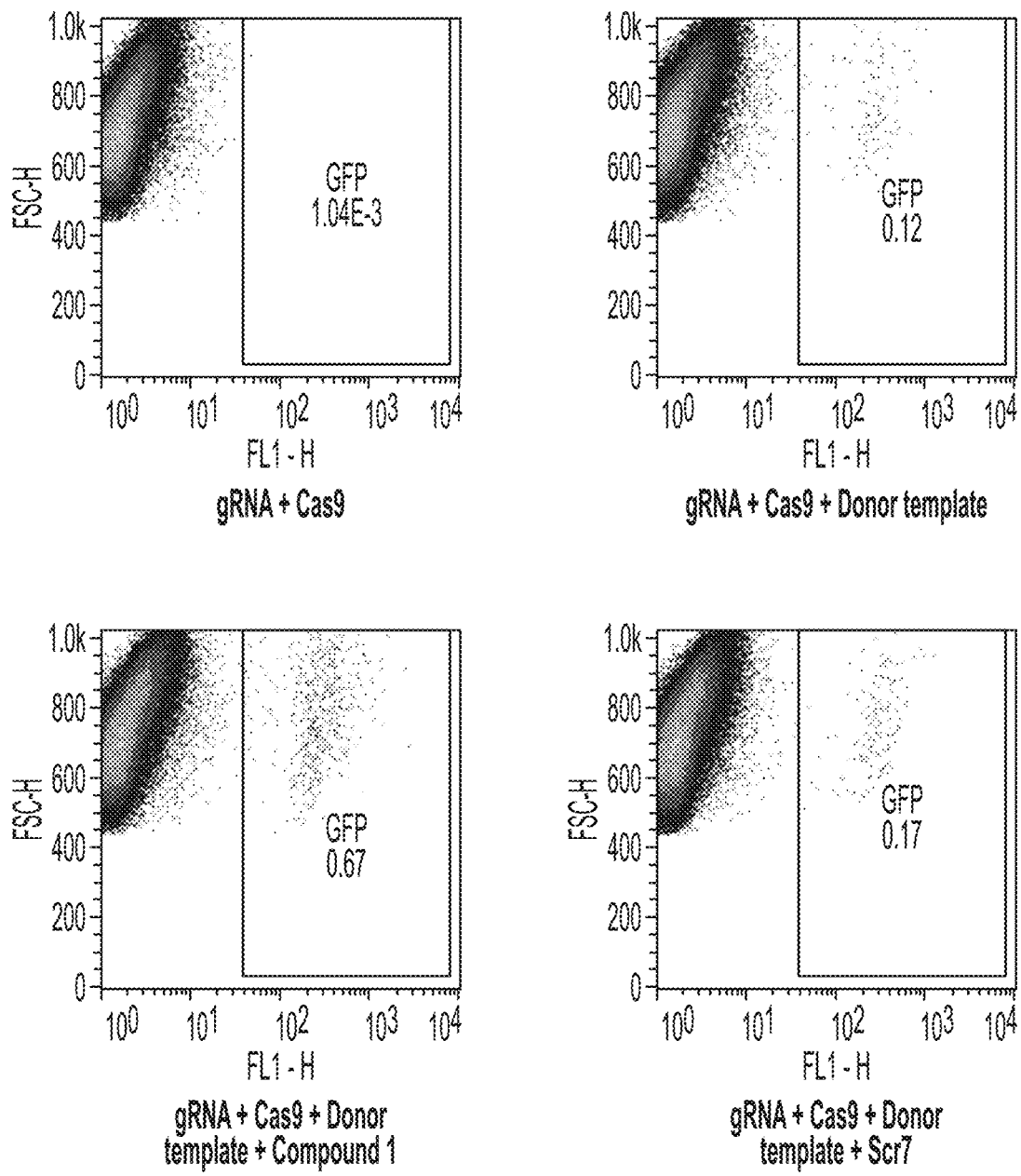
FIGS. 2A-2C are a series of graphs depicting that DNAPK inhibitor Compound 1 enhanced the efficiency of HDR repair pathway in the HEK293-EGIP cell line as quantitated by fluorescence-activated cell sorting flow cytometry (FACS).
Figure 2B:
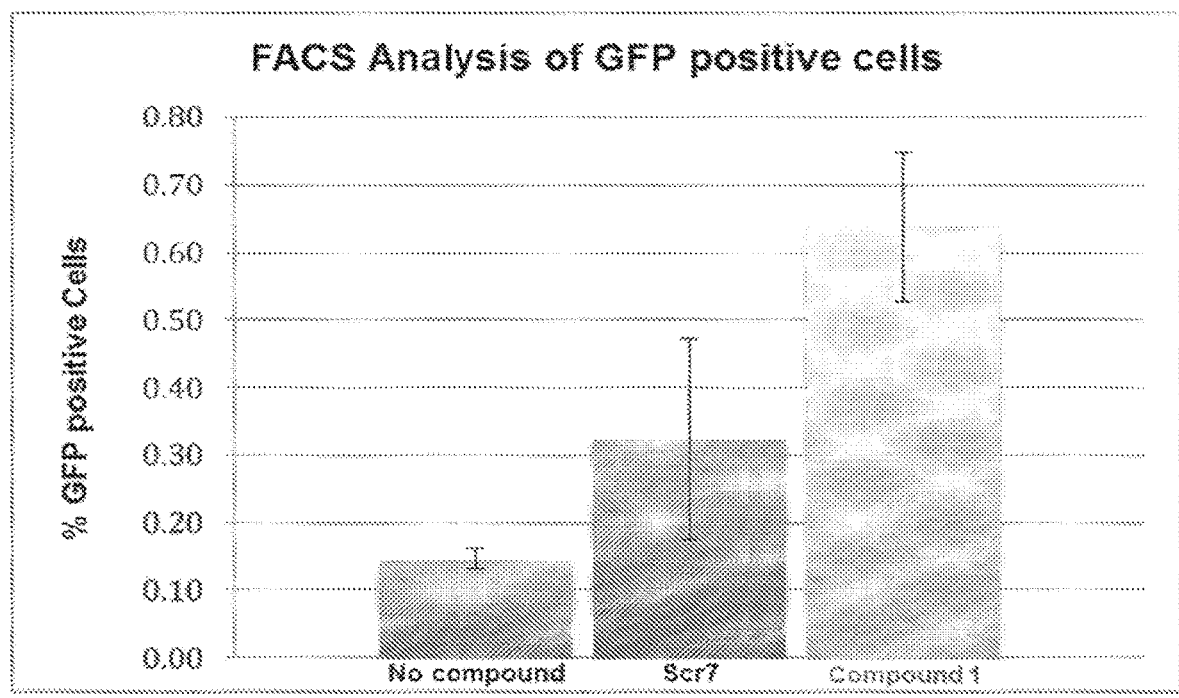
Figure 2C:
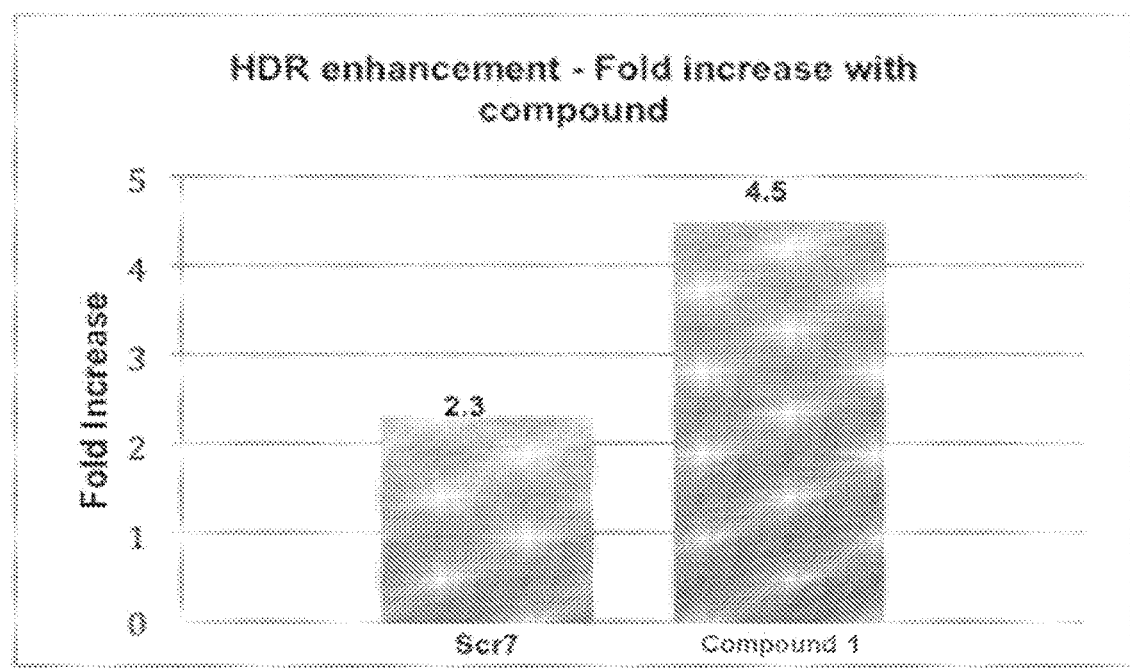

The data from these assays are shown in FIGS. 2A-2C and in Table 1 below. FIG. 2A indicates that the addition of Scr7 to the culture medium increased the amount of CRISPR-genome edited HEK-EGIP cells approximately 30% in comparison to the gRNA-Cas9 and donor template condition only. FIG. 2A further shows that addition of Compound 1 to the culture medium of HEK293-EGIP cells nucleofected with gRNA-Cas9 and donor template resulted in an approximately 83% increase in the amount of CRISPR-genome edited HEK-EGIP cells in comparison to the gRNA-Cas9 and donor template condition only.

Table 1 shows HDR quantification for three technical replicates from one of three independent experiments with similar fold increase in HDR enhancement. The data presented in Table 1 and FIG. 2C show that the addition of Compound 1 to the cell culture medium resulted in an approximate 4.5-fold increase in the amount of CRISPR-genome edited cells, in comparison to the approximate 2.3-fold increase in the amount of CRISPR-genome edited cells in the condition in which the HEK293-EGIP cells were contacted with Scr7.

TABLE 1

FACS Analysis - Percent HDR enhancement (gRNA-Cas9 + donor) with no compound, or with addition of 2.5 uM of Scr7 and 2.5 uM Compound 1

| Expt Replicate | No compound | Scr7 | Compound 1 |
|---|---|---|---|
| 1 | 0.12 | 0.62 | 6.82 |
| 2 | 0.17 | 0.19 | 0.65 |
| 3 | 0.15 | 0.16 | 0.44 |
| Mean | 0.15 | 0.32 | 0.64 |
| Std Dev | 0.03 | 0.26 | 0.19 |
| Std Error | 0.01 | 0.15 | 0.11 |

Collectively, these data show that contacting cells with Compound 1 increased the amounts of CRISPR-based genome editing in comparison to contacting the cells with Scr7, or in comparison to cells that have only been nucleofected with gRNA, Cas9, and donor template.

Figure 1C:
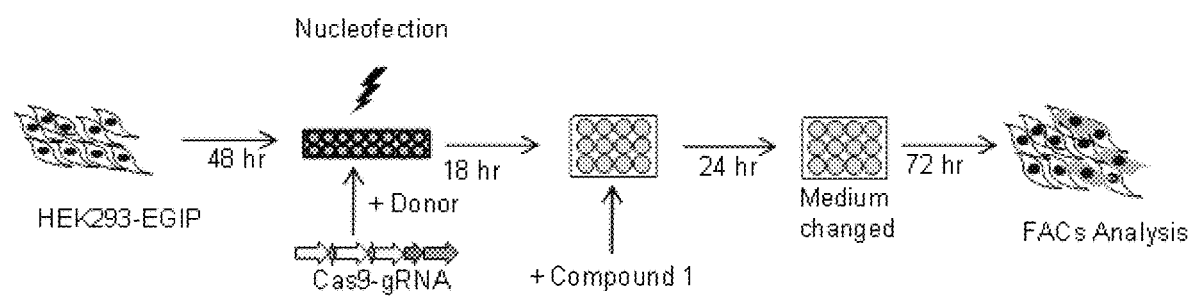

The performance of Compound 3 was also evaluated in using the TLR system and the HEK EGIP cell line was used to monitor HDR efficiency. In addition, the performance of Compound 3 against Scr7 and Nu7026 a putative DNA ligase IV inhibitor and DNAPK inhibitor, respectively, was compared in side-by-side experiments using the robust 'Traffic Light Reporter' (TLR) assay. In the TLR system, the HEK293-EGIP cell line was engineered to stably express non-functional eGFP. The expression of functional eGFP can be restored via the homologous directed repair (HDR) process by transfecting Cas9, gRNA and a DNA repair template. See FIG. 1A-1C. The fold-increase in enhancement of the DNA repair process using the CRISPR-Cas9 system in the presence of a donor repair template was quantitated by Fluorescence Activated Cell Sorter (FACS).

Figure 4:
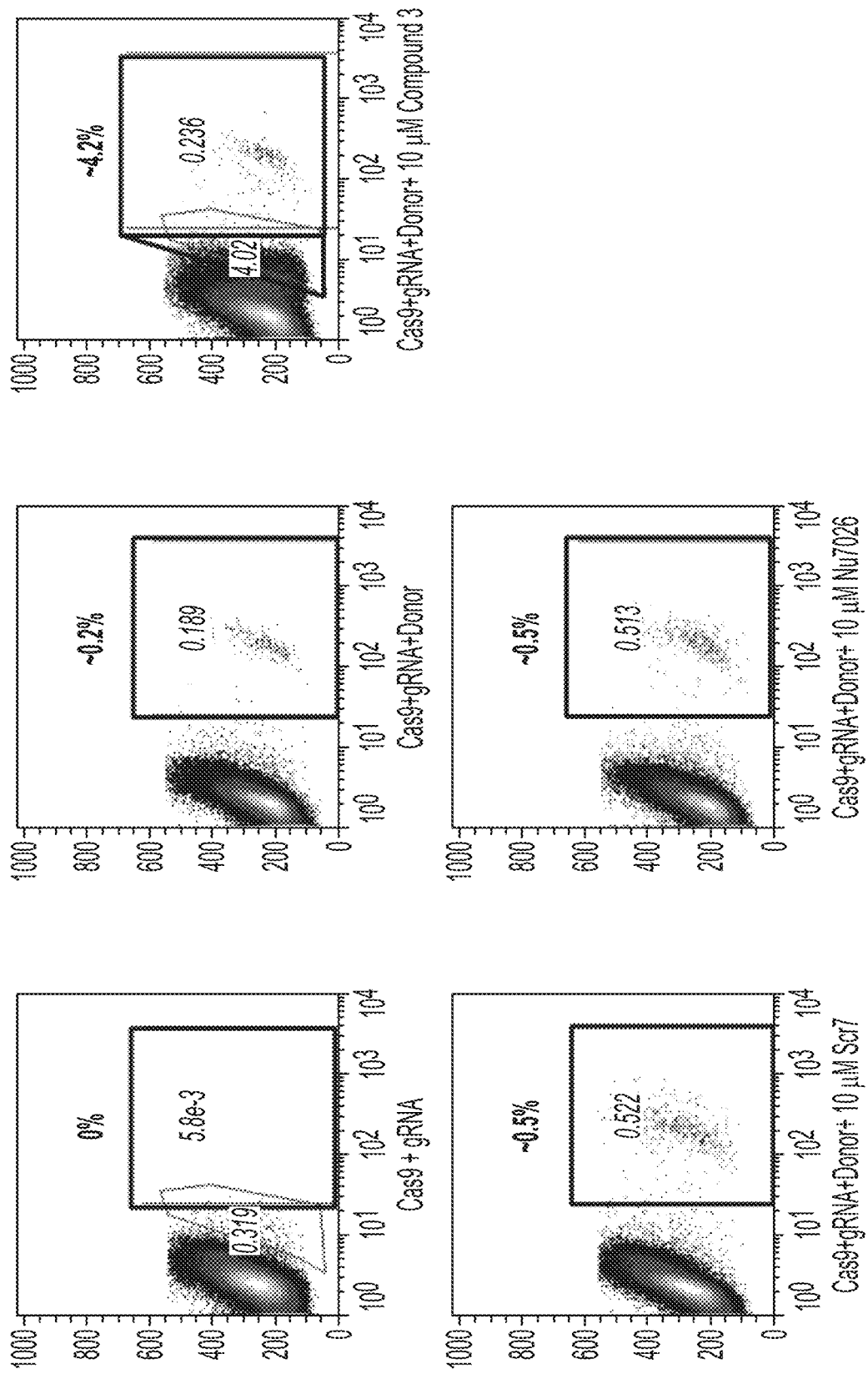
FIG. 4 is a series of flow cytometry dot plots that show HDR efficiency as indicated by GFP+ HEK-EGIP cells following nucleofection of select reagents and specific cell culture conditions. The FACS dot plot graphs depict the following conditions: nucleofection of dual expression gRNA-Cas9 only, nucleofection of dual expression gRNA-Cas9 with donor repair template, nucleofection of dual expression gRNA-Cas9 with donor template and culture with a small molecule DNAPK inhibitor Compound 3, and nucleofection with gRNA-Cas9 with donor repair template and culture of the cells with 10ΣM of Scr7, and nucleofection with gRNA-Cas9 with donor repair template and culture of the cells with 10ΣM Nu7026. The data indicated an approximate 4-fold increase in GFP positive cells from transfection of donor repair template vector and gRNA-Cas9 expression plasmids in the presence of NHEJ inhibitors Compound 3 in comparison to the gRNA-Cas9 only condition.

48 hours post transfection via electroporation, eGFP positive cells began to emerge. Flow cytometry analysis 10 days post transfection yielded 4% GFP positive cells in the presence of 10 μM Compound 3. In contrast, cells without compound yielded about 0.2% eGFP positive cells and those treated with the commercial DNAPK inhibitor SCR7 showed enhancement of about 0.5% (FIG. 4). Data from experiments carried out in triplicates, were consistent with about 8-fold increase in HDR enhancement compared to transfection in the presence the commercial compound SCR7.

Summary

Figure 3:
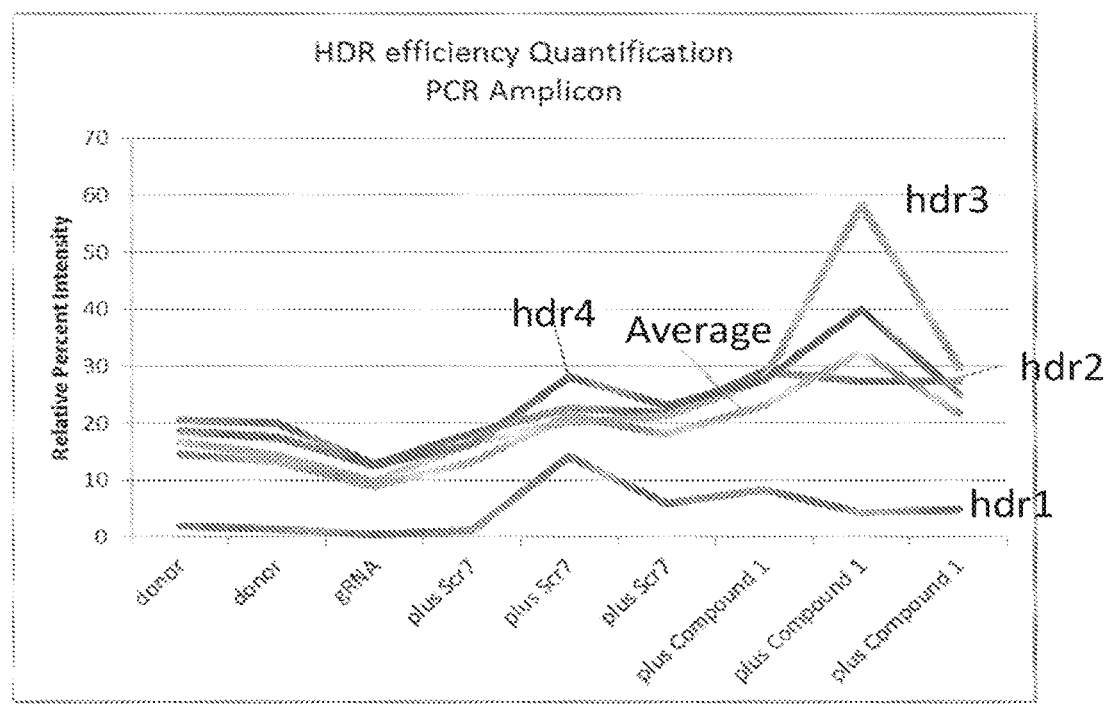
FIG. 3 is a graph that shows PCR-based quantification of HDR efficiency in HEK-293 EGIP cells nucleofected with donor template and Cas9-sgRNA and contacted with either Scr7 or Compound 1.

The performance of DNAPK inhibitor Compound 1 was evaluated with regard to its ability to stimulate CRISPR-based HDR repair process by suppressing the error prone NHEJ DNA repair pathway. Furthermore, the performance of Compound 1 was compared with Scr7 (FIGS. 2A, 2B and 3), a putative DNA ligase IV inhibitor in side-by-side experiments. The robust "Traffic Light Reporter" (TLR) assay was used (FIG. 1B) to quantitate the fold-increase in enhancement of HDR-mediated DNA repair process in the CRISPR-Cas9 system. In the TLR system, the HEK293-EGIP stable cell line expressing the "broken" green fluorescent protein eGFP, relies on HDR-mediated repair to generate functional eGFP in the presence of DNA donor template (see FIGS. 1B and 1C). As shown in the experimental workflow in FIG. 1C, functional GFP positive cells appeared through HDR pathway where the 56 nt insertion was replaced with the correct DNA sequence. Forty-eight hours post transfection through electroporation, GFP positive cells emerged. Flow cytometry analysis displayed that HDR event, as indicated by GFP positive cells, occurred in less than 1% of the cells (FIGS. 2A and 2B) under the experimental conditions. Based on two separate experiments carried out in triplicates, the data showed that addition of Compound 1 provided 4.5-fold increase in HDR enhancement compared to transfection in the absence of compound, and 2-fold better HDR enhancement compared to transfection with Scr7 (FIGS. 2B and 2C).

The assays that evaluated the performance of Compound 3 showed that Compound 3 enhanced HDR gene editing efficiency. The data from these experiments show that there is an approximately 4-fold enhancement of HDR efficiency, as indicated by FACS analysis, in the presence of Compound 3 in comparison to the Cas9+gRNA only condition. See FIG. 4.

Example 4: Comparison of Small Molecule NHEJ Inhibitors for Increasing HDR Genome Editing Further experiments were conducted utilizing the HEK293-EGIP cell line to ascertain HDR efficiency following contact with a DNAPK inhibitor or an NHEJ inhibitor Another series of experiments compared increase in HDR efficiency following contact with either Scr7 or Compound 1, a DNAPK inhibitor. For these experiments, HEK293-EGIP cells were nucleofected with donor template only or donor template and Cas9-sgRNA. To test the ability of Scr7 and Compound 1 to enhance HDR editing, cells that had been nucleofected with either donor template alone, or donor template and Cas9-sgRNA were administered either Scr7 or Compound 1. The data from these experiments are presented in FIG. 3 and Table 2 below.

HDR recombination status was ascertained by traditional "end-point" PCR primer genotyping and quantitation based on agarose band intensities. The primers produced distinct amplicons: a 219 bp nucleotide band corresponded to unmodified cells and a 163 bp nucleotide product for HDR event. Intensity of these bands on a >2.5% gel allows for estimation of HDR by densitometry using a Bio-Imager. The technique allows for the relative ranking of conditions for improvement of HDR by inhibitors of NHEJ. The genotyping PCR primer pairs for these assays is shown below.

```
HDR primer_1
                             (SEQ ID NO: 6)
ACTTCTTCAAGTCCGCCATGCCC HDR primer_2
                             (SEQ ID NO: 7)
ATGTTGCCGTCCTCCTTGAAGTCG
```

The Cas9 protein and sgRNAs can be delivered in the form of synthetic RNAs instead of the vector systems purchased from SBI. In addition to boosting HDR efficiency, our internal genome editing experiments indicated higher cell viability following ribonucleoprotein protein (RNP) transfection compared with DNA transfection. Furthermore cell synchronization of the S/G2 phase can also stimulate HDR (Lin S et al. Elife. 2014 Dec. 15; 3, 2014). These new strategies and robust detection of genome editing such as digital droplet PCR and next-generation sequencing would streamline genome editing for both therapeutic and research purposes.

TABLE 2

HDR Editing Efficiency Following Administration of Either Scr7 or Compound 1to HEK293-EGIP Cells Nucleofected with Donor Template and Cas9-Scr7

|  | replicate 1 hdr 1 | replicate 2 hdr 2 | replicate 3 hdr 3 | replicate 4 hdr 4 | Average |
|---|---|---|---|---|---|
| donor | 2 | 20.5 | 16.7 | 18.7 | 14.475 |
| donor | 1.4 | 20 | 14.4 | 17.4 | 13.3 |
| gRNA | 0.5 | 12.8 | 9.8 | 12.7 | 8.95 |
| plus Scr 7 | 1.3 | 18.2 | 16.6 | 16.4 | 13.125 |
| plus Scr 7 | 14.1 | 22.7 | 20.2 | 28.1 | 21.275 |
| plus Scr 7 | 5.8 | 21.8 | 21.3 | 23 | 17.975 |
| plus Compound 1 | 8.4 | 29 | 27.5 | 27.6 | 23.125 |
| plus Compound 1 | 4.3 | 27.4 | 58.3 | 40 | 32.5 |
| plus Compound 1 | 4.9 | 27.4 | 29.8 | 25.1 | 21.8 |

The Cas9 protein and sgRNAs can be delivered in the form of synthetic RNAs instead of the vector systems purchased from SBI. In addition to boosting HDR efficiency, our internal genome editing experiments indicated higher cell viability following ribonucleoprotein protein (RNP) transfection compared with DNA transfection. Furthermore cell synchronization of the S/G2 phase can also stimulate HDR (Lin S et al. Elife. 2014 Dec. 15; 3, 2014). These new strategies and robust detection of genome editing such as digital droplet PCR and next-generation sequencing would streamline genome editing for both therapeutic and research purposes.

Example 5: Administration of DNAPK Inhibitor Compound 1 Increased Gene Editing Assays were performed to ascertain the ability of a DNAPK inhibitor to allow for the editing of a target gene. For these assays, the editing of the Serpin A1 gene from M to Z form was assessed. To this end, Huh7 hepato cellular carcinoma cells were nucleofected with gRNA and Cas9 protein, with or without a donor repair template in which a KpnI site was introduced. The nucleofected cells were then cultured in the presence of DMSO or 2.5 pM Compound 1 for three days, following which, the genomic DNA was amplified and assessed for the introduction of the Kpn site.

The assay works as follows: when the SerpinA1 gene is edited, Kpn endonuclease is able to digest the gene fragment, resulting in the appearance of a digested band on a gel only when the SerpinA1 gene is edited. Conversely, when the SerpinA1 is not edited, the Kpn endonuclease is not able to cut the gene fragment, and thus there will not be an appearance of a new, digested band on a gel.

Figure 5:
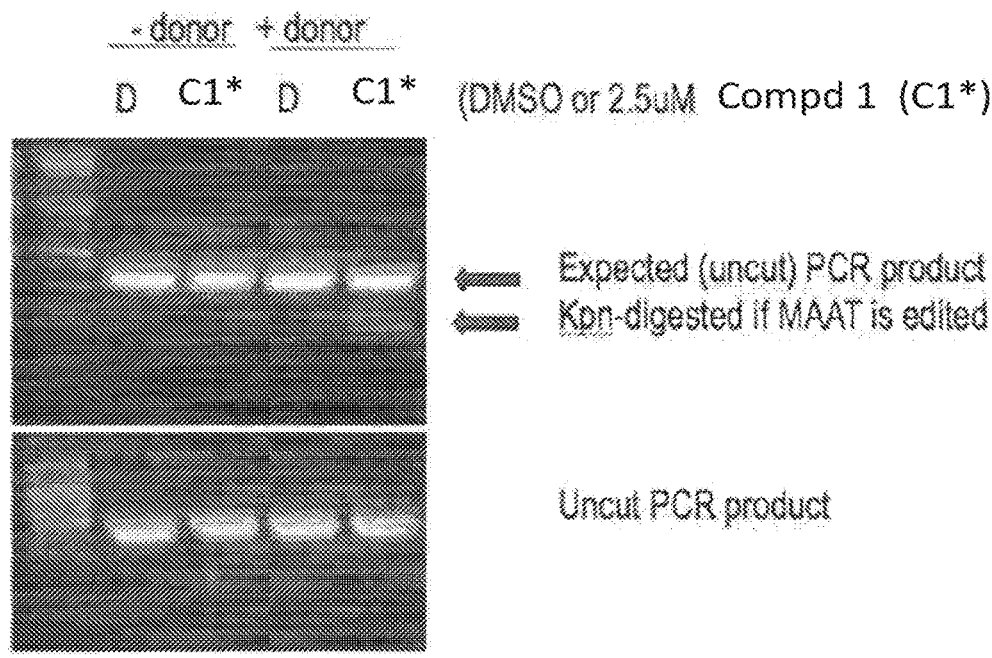
FIG. 5 is a gel from an amplified SerpinA1 gene that was isolated from Huh7 cells that were nucleofected with gRNA with or without donor repair template and Cas9 protein, in which the donor repair template was used to introduce a Kpn endonuclease site. The nucleofected cells were either cultured in the DNAPK inhibitor, Compound 1, or in the presence of DMSO for 3 days prior to genomic DNA PCR followed by digest with Kpn 1. The data show that Compound 1 allowed for gene editing in comparison to the DMSO condition, or the control no donor repair template condition.

The data from these assays indicated that incubation of the nucleofected cells in the presence of Compound 1 resulted in gene editing of the SerpinA1 gene to introduce a DNA fragment of interest, here the Kpnl site (FIG. 5). These data showed that DNAPK inhibitors, such as Compound 1, can be used to allow for, or augment, gene editing capability.

EQUIVALENTS

While this disclosure has been particularly shown and described with references to preferred embodiments thereof, it will be understood by those skilled in the art that various changes in form and details may be made therein without departing from the spirt and scope of the disclosure as defined by the appended claims. Those skilled in the art will recognize or be able to ascertain using no more than routine experimentation, many equivalents to the specific embodiments of the disclosure described specifically herein. Such equivalents are intended to be encompassed in the scope of the claims.

We claim:

1. A kit or composition for editing one or more target genomic regions, comprising:
   a genome editing system; and
   a compound represented by Structural Formula (I) or Structural Formula (I'):

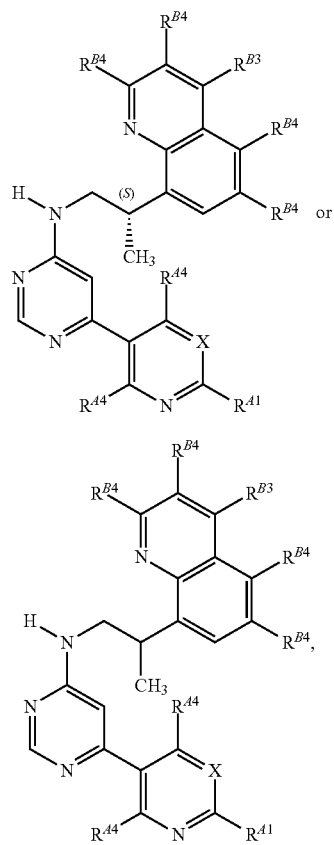

or a pharmaceutically acceptable salt or a co-crystal thereof; wherein

X is N, $CR^{A5}$;

$R^{A1}$ is F, $C_{1-4}$alkyl, $C_{3-5}$cycloalkyl, $OC_{1-4}$alkyl, $OC_{1-4}$alkyl-$C_{3-5}$cycloalkyl, $NH_2$, $NHC_{1-4}$alkyl, $NHC_{1-4}$alkyl-$C_{3-5}$Cycloalkyl, or $C_{0-4}$alkyl-heterocyclyl, wherein said heterocyclyl is selected from oxetanyl, tetrahydrofuranyl, tetrahydropyranyl, or morpholinyl, and each of said alkyl, cycloalkyl, or heterocyclyl is optionally substituted with up to three F atoms, up to three $^2$H atoms, up to two non-geminal OH groups, or up to two $OC_{1-2}$alkyl;

each $R^{A4}$ is, independently, H or $^2$H;

$R^{A5}$ is hydrogen, F, $C_{1-4}$alkyl, or $OC_{1-4}$alkyl, wherein each of said alkyl is optionally substituted with up to three F atoms or up to three $^2$H atoms;

$R^{B3}$ is $C(O)NHC_{1-4}$ alkyl, wherein said alkyl is optionally substituted with up to three F atoms, up to three $^2$H atoms, up to two non-geminal OH groups, or up to two $OC_{1-2}$alkyl; and each $R^{B4}$ is, independently, hydrogen, deuterium, F, or $C_{1-4}$alkyl.

2. The kit or composition of claim 1, wherein the compound is represented by Structural Formula (II), Structural Formula (II'), Structural Formula (II"), or Structural Formula (II'''):

(II)

(II')

-continued

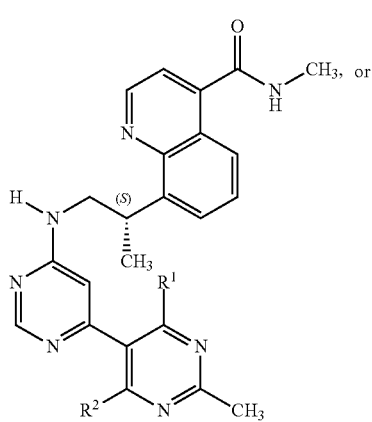

(II″)

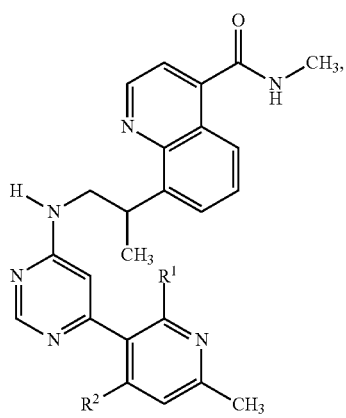

(II‴)

or a pharmaceutically acceptable salt thereof or a co-crystal thereof,
wherein each of R¹ and R² is hydrogen or deuterium.

3. The kit or composition of claim 1 or 2, wherein the genome editing system is a meganuclease based system, a zinc finger nuclease (ZFN) based system, a Transcription Activator-Like Effector-based Nuclease (TALEN) system, a CRISPR-based system, or NgAgo-based system.

4. The kit or composition of claim 3, wherein genome editing system is a CRISPR-based system.

5. The kit or composition of claim 4, wherein the CRISPR-based system is a CRISPR-Cas system or a CRISPR-Cpf system.

6. The kit or composition of claim 5, wherein the CRISPR-based system is a CRISPR-Cas system and wherein the CRISPR-Cas system comprises: (a) at least one guide RNA element comprising: (i) a targeter RNA comprising a nucleotide sequence substantially complementary to a nucleotide sequence at the one or more target genomic regions or a nucleic acid comprising a nucleotide sequence(s) encoding the targeter RNA; (ii) and an activator RNA comprising a nucleotide sequence that is capable of hybridizing with the targeter RNA, or a nucleic acid comprising a nucleotide sequence(s) encoding the activator RNA; and (b) a Cas protein element comprising a Cas protein or a nucleic acid comprising a nucleotide sequence(s) encoding the Cas protein.

7. The kit or composition of claim 6, wherein the Cas protein is a Type-II Cas9 protein.

8. The kit or composition of claim 7, wherein the Cas9 protein is a SaCas9, SpCas9, SpCas9n, Cas9-HF, Cas9-H840A, FokI-dCas9, or D10A nickase, or any combination thereof.

9. The kit or composition of claim 5, wherein the CRISPR-based system is a CRISPR-Cpf system, and wherein the CRISPR-Cpf system comprises: (a) a targeter RNA comprising a nucleotide sequence substantially complementary to a nucleotide sequence at the one or more target genomic regions, or a nucleic acid comprising a nucleotide sequence(s) encoding the targeter RNA; and (b) a Cpf protein element comprising a Cpf protein or a nucleic acid comprising a nucleotide sequence(s) encoding the Cpf protein.

10. The kit or composition of claim 1, wherein the genome editing system is included or packaged in one or more vectors.

11. The kit or composition of claim 10, wherein the one or more vectors are selected from viral vectors, plasmids, or ssDNAs.

12. The kit or composition of claim 11, wherein the viral vectors are selected from the group consisting of retroviral, lentiviral, adenoviral, adeno-associated and herpes simplex viral vectors.

13. The kit or composition of claim 1, wherein the compound is:

(Compound 1)

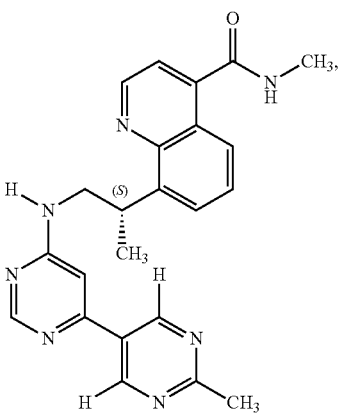

(Compound 2)

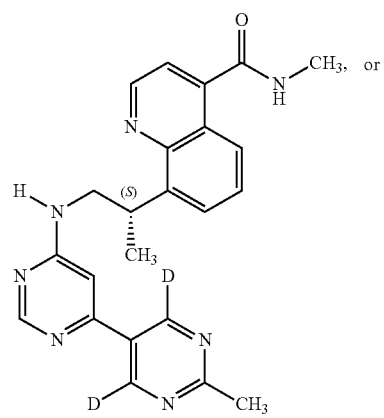

or (Compound 3)

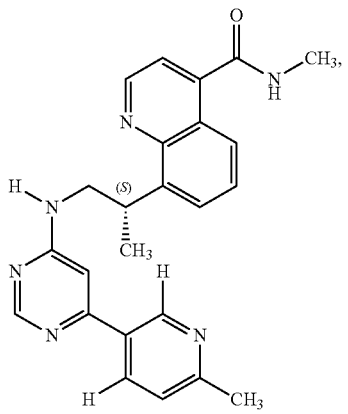

or a pharmaceutically acceptable salt thereof.

14. The kit or composition of claim 1, wherein the compound is a co-crystal comprising a compound having a structure of Formula (I) or Formula (II) and a co-crystal former selected from adipic acid, citric acid, fumaric acid, maleic acid, succinic acid, or benzoic acid.

15. The kit or composition of claim 1, wherein the compound is a co-crystal comprising: (a) Compound 1 or Compound 2; and (b) adipic acid:

(Compound 1)

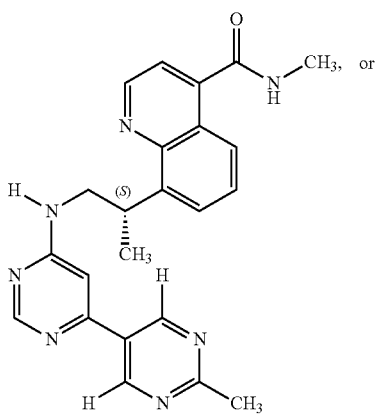

or (Compound 2)

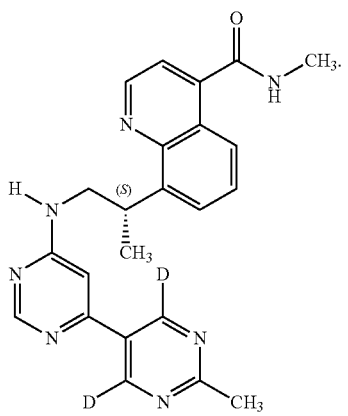

16. The kit or composition of claim 1, wherein the compound is a co-crystal comprising: (a) Compound (1); and (b) adipic acid:

(Compound 1)

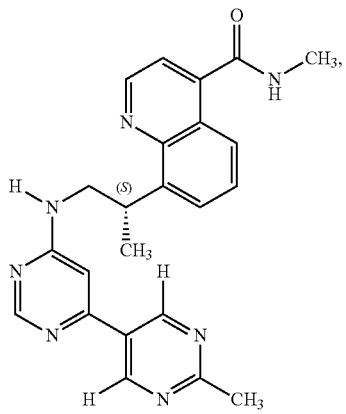

wherein the molar ratio of adipic acid to Compound (1) is about 2 to 1.

17. The kit or composition of claim 1, wherein the compound is a co-crystal comprising: (a) Compound (2); and (b) adipic acid:

(Compound 2)

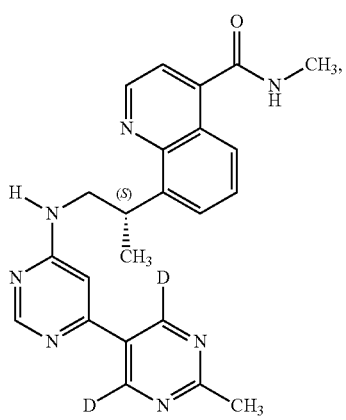

wherein the molar ratio of adipic acid to Compound (2) is about 2 to 1.

18. The kit or composition of claim 1, wherein the compound is Compound 3, (Compound 3)

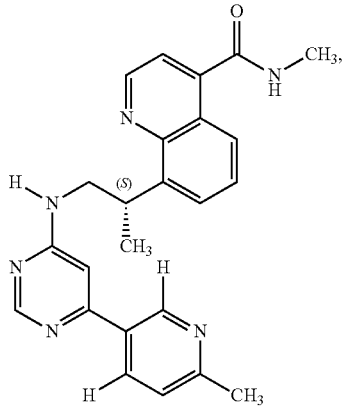

or a pharmaceutically acceptable salt thereof.

* * * * *